United States Patent
Biedermann et al.

(10) Patent No.: US 6,903,118 B1
(45) Date of Patent: Jun. 7, 2005

(54) PIPERAZINYL-SUBSTITUTED PYRIDYLALKANE, ALKENE AND ALKINE CARBOXAMIDES

(75) Inventors: Elfi Biedermann, Vaterstetten (DE); Max Hasmann, Neuried (DE); Roland Löser, Feldafing (DE); Benno Rattel, Munich (DE); Friedemann Reiter, Putzbrunn (DE); Barbara Schein, Neufahrn (DE); Klaus Seibel, Gräfelfing (DE); Klaus Vogt, Munich (DE); Katja Wosikowski, Poing (DE); Isabel Schemainda, Munich (DE)

(73) Assignee: Klinge Pharma GmbH, Munich (DE)

( * ) Notice: Subject to any disclaimer, the term of this patent is extended or adjusted under 35 U.S.C. 154(b) by 0 days.

(21) Appl. No.: 09/596,001

(22) Filed: Jun. 16, 2000

Related U.S. Application Data

(63) Continuation of application No. PCT/EP98/08268, filed on Dec. 16, 1998.

(30) Foreign Application Priority Data

Dec. 17, 1997 (DE) ......................................... 197 56 236

(51) Int. Cl.[7] ...................... A61K 31/445; A61K 31/44; C07D 401/00; C07D 239/72; C07D 251/00
(52) U.S. Cl. ....................... 514/326; 514/252; 514/332; 514/335; 514/354; 514/355; 514/356; 514/357; 514/358; 544/180; 544/283; 544/360
(58) Field of Search ................................. 514/326, 252, 514/332, 335, 354, 355, 356, 357, 358; 544/180, 283, 360

(56) References Cited

U.S. PATENT DOCUMENTS

| | | | |
|---|---|---|---|
| 4,283,541 A | 8/1981 | Shroff et al. ................ | 546/336 |
| 5,169,856 A | 12/1992 | Goto et al. .................. | 514/331 |
| 5,260,323 A | 11/1993 | Baader et al. ............... | 514/356 |
| 5,326,772 A | 7/1994 | Klemm et al. ............... | 514/318 |
| 6,451,816 B1 * | 9/2002 | Biedermann et al. ........ | 514/318 |
| 2004/0029861 A1 * | 2/2004 | Biedemann et al. ... | 514/211.15 |

FOREIGN PATENT DOCUMENTS

| | | |
|---|---|---|
| CA | 2085954 | 6/1993 |
| DE | 4020570 | 1/1992 |
| EP | 048045 | 3/1982 |
| EP | 210782 | 2/1987 |
| EP | 271023 | 6/1988 |
| EP | 330026 | 8/1989 |
| EP | 343307 | 11/1989 |
| EP | 416581 | 3/1991 |
| EP | 471236 | 2/1992 |
| EP | 479601 | 4/1992 |
| EP | 522606 | 1/1993 |
| EP | 530444 | 3/1993 |
| EP | 548883 | 6/1993 |
| EP | 512902 | 4/1994 |
| EP | 428434 | 5/1994 |
| GB | 2304714 | 11/1998 |
| JP | 57136518 | 8/1982 |
| JP | 63179869 | 7/1988 |
| WO | WO89/07443 | 8/1989 |
| WO | WO91/15484 | 10/1991 |
| WO | WO91/15485 | 10/1991 |
| WO | WO93/13083 | 7/1993 |
| WO | WO93/14070 | 7/1993 |
| WO | WO93/14113 | 7/1993 |
| WO | WO94/01402 | 1/1994 |
| WO | WO95/10514 | 4/1995 |
| WO | WO95/10515 | 4/1995 |
| WO | WO95/10516 | 4/1995 |
| WO | WO95/24894 | 9/1995 |
| WO | WO96/31477 | 10/1996 |
| WO | WO96/31478 | 10/1996 |
| WO | WO97/48397 | 12/1997 |
| WO | WO97/48695 | 1/1998 |

OTHER PUBLICATIONS

Chemical Abstracts, vol. 124, No. 13, 1996.

Chemical Abstracts, vol. 115, 1994.

Chemical Abstracts, vol. 114, 1991, Abs # 101646t.

Nishikawa et al., "Acrylamide Derivatives as Antiallergic Agents. 2. Synthesis and Structure–Activity Relationships of N–[4–[4–(Diphenylmethyl)–1–piperazinyl]butyl]–3–(3–pyridyl)acrylamides" Chem. Pharm. Bull. 37(1) 100–105 (1989).

(Continued)

Primary Examiner—Richard L. Raymond
Assistant Examiner—Tamthom N. Troung
(74) Attorney, Agent, or Firm—Fitch, Even, Tabin & Flannery

(57) ABSTRACT

The invention relates to new piperazinyl-substituted pyridylalkane, alkene, and alkine acid amides substituted with saturated or one or several-fold unsaturated hydrocarbon residue in the carboxylic acid group according to the general formula (I) as well as methods for the production of these compounds, medicaments containing these and their production as well as their therapeutic use, especially as cytostatic agents and immunosuppressive agents, for example in the treatment or prevention of various types of tumors and control of immune reactions such as autoimmune diseases.

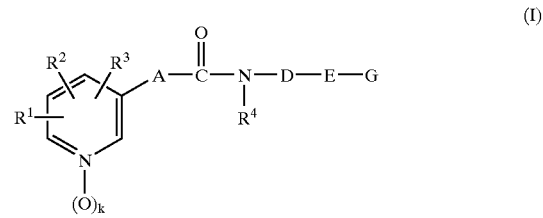

(I)

29 Claims, No Drawings

OTHER PUBLICATIONS

Nishikawa et al., "Acrylamide Derivatives as Antiallergic Agents. 2. Synthesis and Structure–Activity Relationships of N–[4–[4–(Diphenylmethyl)–1–piperazinyl]butyl]–3–(3–pyridyl)acrylamides" J. Med. Chem. 1989, 32, 583–593.

Ishihara et al., "Central Cholinergic Agents. II. Synthesis and Acetylcholinesterase Inhibitory Activities of N–[w–[N–Alkyl–N–(phenylmethyl) amino]alkyl]–3–arylpropenamides" Chem. Pharm. Bull. 39(12) 3236–3234 (1991).

Ross, "The Preparation of Some 4–Substituted Nicotinic Acids and Nicotinamides" J. Chem. Soc. (C), 1966, 1816–1820.

Eder M. et al, "Allgemeine Pathologie unde Pathologische Anatomie", Springer Verlag, Berlin, 33$^{th}$ Ed., 1990, 208–213.

Verlag et. al., ROTE LISTE, 1997, Aulendorj, Germany.

* cited by examiner

PIPERAZINYL-SUBSTITUTED PYRIDYLALKANE, ALKENE AND ALKINE CARBOXAMIDES

This application is a continuation of PCT/EP98/08268 filed Dec. 16, 1998.

The invention relates to new piperazinyl-substituted pyridyl-alkane, alkene and alkine carboxamides with a saturated, one or several-fold unsaturated hydrocarbon residue in the carboxylic acid portion, methods for the synthesis of these compounds, medicaments containing these and their production as well as their therapeutic use especially as cytostatic agents and immunosuppresive agents, for example, in the treatment or prevention of various types of tumors and control of immune reactions, for example of autoimmune diseases.

A pressing need exists for new pharmaceuticals and/or medicaments for cytostatic therapy which not only possess a strong activity, but also exert diminished side effects in comparison to many classical cancerostatic agents, whereby treatment of a broad as possible spectrum of tumors should be made accessible. Furthermore, effective cytostatic agents for an efficient therapy should be made available. Active ingredients of this type should also be exceptionally suitable in the mentioned indications for a combination therapy, be it in connection with other cytostatic agents or with radiation (for example X-rays, radioactive elements, such as cobalt, or linear accelerator, etc.), with operative procedures, heat treatment, etc.

Additionally, from another point of view, there exists a strong need in the field of tumor therapy for new compounds, for example for overcoming or avoiding resistances, which enrich the pallet of cancerostatics based on new modes of action in the ideal case.

This object was successfully solved by the creation of the piperazinyl-substituted pyridylalkane, alkene and alkine carboxamide derivatives as defined in detail in the claims and medicaments containing these as well as the use of these compounds, optionally in combination with other suitable active ingredients and adjuvants, for cytostatic and immunosuppressive therapy or prevention.

It is known that various pyridine compounds or piperazine derivatives substituted in a specific manner have pharmacologically useful properties—however, in contrast to the actions of the compounds according to the invention, these lie in completely different fields of indication.

Thus, ω-pyridyl alkane and/or alkene amides with anti-allergic activity are described in EP 0 210 782 which are referred to as having a 5-lipoxygenase-inhibiting and anti-histamine action, wherein the amide components of these compounds contain a piperizine or homopiperizine ring and the pyridine ring can be linked together in the 2-, 3- or 4-position. However, corresponding overlapping compound groups are excluded from the present claimed scope of protection according to the invention.

JP 63,179,869 describes further pyridyl amides, ω-pyridyl alkane and alkene amides as anti-allergic effective substances containing a substituted piperidine ring in the amine component. Similarly structured compounds with the same properties are mentioned in Chem. Pharm. Bull 37, 100–105 (1989) as well as in J. Med. Chem. 1989, 583–593.

The synthesis and pharmacological evaluation of heterocyclic carboxamides which can be substituted at an end of the molecule by completely different heterocycles such as thiophene, guinoline, indole, benzimidazole or indazole as well as pyridine are described in J. Med. Chem., 1996, pages 4692–4706. As opposed to the compounds according to the invention, those published carboxamides possess an activity directed against psychoses. A few particularly named piperazine-substituted pyridyl carboxamides and/or their formula group therein are not encompassed by the present protective scope of the compounds of the invention according to the meanings given in the present claims because they have a direct bond instead of the structural element A. Based on the completely different therapeutic possibility of the known compounds in the field of psychiatry as compared to the indications according to the invention, it could not be expected that the compounds of the present invention would have the named cancerostatic and immunosuppressive effects.

Pyridyl ureas, pyridyl thioureas and pyridyl carbonamides, wherein the amide portion is bound over an aryl-substituted alkyl chain with a piperidine ring or piperidine ring or piperazine ring, are described for example in EP-A-0 428 434 or in EP-A-0 512 902 as antagonists of the neurokinin receptor and substance P. Furthermore, pyridyl (alkyl)carbonamides, pyridyl(alkyl)sulfonamides and analogous ureas, wherein the amide portion is bound to piperidine ring over an alkyl chain, are disclosed in EP-A-0 479 601 as active ingredients with anti-arrhythmic properties.

Further structurally closely related compounds are represented by the piperidine compounds described in EP-A-0 330 026. However, no 3-pyridyl derivatives were concretely described and no concrete examples were disclosed in this publication, aside from a single compound which is described below. These known compounds are distinguished by an anti-cholinesterase activity, an anti-amnesia activity as well as activities directed against hyperkinesia, senile dementia, mania and Alzheimer's disease.

In WO 91/15 485, the production of pyridine-3,5-dicarboxylic acid esters and amides as well as their use for the treatment of tumor conditions is described. These compounds differ from the compounds according to the invention described below in very important structural features, for example by the dicarboxyl grouping on the pyridine ring or the absence of the hydrocarbon chain between the pyridine ring and the amide grouping. The compounds disclosed in WO 89/07 443 in the form of optically pure R(−)-niguldipin and further analogous dihydropyridines with cytotoxic activity have larger structural differences. However, as compared to these known compounds, the compounds according to the invention unexpectedly possess a better activity and a wider spectrum of action despite the large structural difference.

In the international PCT patent applications WO 95/10516, WO 96/31477, WO 96/31478 or for example in WO 95/10515, tricyclic amide compounds are described which possess an anti-proliferative activity. All of these compounds described therein are distinguished in that they must imperatively possess a tricyclic anellated ring system with at least one nitrogen atom, for example 6,11-dihydro-5H-benzo[5,6]cyclohepta[1,2-b]pyridinyl ring system as a pharmaphoric group, whereby the molecule portion opposite this tricyclic anellated system is uncommonly variable and represents one of many variation possibilities among numerous substitution possibilities of the given pyridyl substitution. A further meaningful difference in the substitution of these molecules in comparison to the compounds according to the invention is to be seen in the lack of the present structural element D, i.e. both heterocycles found in opposition are directly bound over the carboxy group without being bound over an alkaline chain found there.

A further essential difference of the compounds according to the invention in comparison to these tricyclic compounds is to be recognized in the presence of the terminal 3-pyridyl-substitution which must be present. The presence of this heterocyclic ring required according to the invention as well as the particular bond in the 3-position according to the substitution of the invention in comparison to the above mentioned anti-proliferative compounds of the state of the art indicates that this 3-pyridyl group is an important factor for the anti-tumor action.

In fact, the compounds according to the invention cover a different tumor spectrum from those named in the PCT/WO publications with this necessarily present tricyclic anellated ring system. In the mentioned PCT/WO publications of the state of the art, a treatment possibility in tumors is merely mentioned which is made in connection with a potential inhibition of the farnesyl protein transferase, whereby this mechanism relates to the expression of the activated ras-oncogene. In contrast to this, the compounds according to the invention with the 3-pyridyl-substitution required according to the invention are not limited to the therapy of tumor cells of this type with abnormal production of the ras-oncogene; rather, the therapy possibilities with the new compounds according to the invention extend to the combat of numerous other types of tumors with different causal mechanisms as well as immunosuppressive treatment possibilities such as autoimmune diseases.

In view of this art, the finding that the compounds according to the general formula (I) with the particular substitutions defined below have superior pharmacological activities which make them particularly suitable in an excellent manner for the therapy of abnormal cell growth such as tumor illnesses over a broad anti-proliferative spectrum, was completely unexpected. The pharmacological finding that, aside from the cytostatic effectiveness, especially with different tumor spectra, the compounds according to the invention also possess immunosuppressive properties and additionally favorable abortive properties without harmful mutagenic effects is to be considered as equally surprising.

Structurally close pyridyl compounds wherein instead of the piperazine ring, a cyclic non-aromatic heterocyclic ring residue with merely one ring nitrogen atom and optionally an additional ring oxygen atom, preferably a piperidinyl residue, is incorporated as well as their use especially as cytostatic agents are subject matter of the older patent applications, P 196 24 704.7-44, P 196 24 668.7-41 as well as P 196 24 659.8-44 which have not yet been published.

The most important differentiating feature of the new compounds according to the invention with respect to these older, non-prepublished compounds is therefore the structural feature E which in the present application always represents especially piperazine or hexahydro-1,4-diazepine.

These new piperazinyl-substituted pyridyl carboxamides correspond to the following general formula:

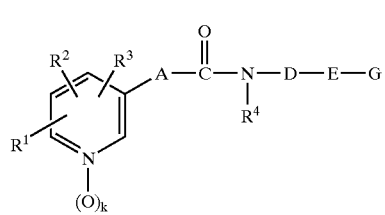

wherein the structural element E has the following meaning:

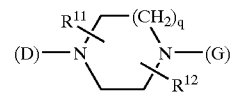

whereby q is 1, 2 or 3 and therewith can represent the N-heterocyclic ring piperazine, hexahydro-1,4-diazepine or octahydro-1,4-azocine.

The meaning of the remaining substituents and the preferred embodiments of the compound groups according to the invention falling under the general formula as well as particularly preferred end products are defined in claims 1 to 7 in detail.

The compounds of Formula (I), which represent the end products can optionally exist as cis- and trans-isomers, E- and Z-isomers, for example when A is a cyclopropane ring or D contains one or more double bonds. Subject matter of the invention is the pure isomers as well as their mixtures. Furthermore, the compounds of Formula (I) can contain one or more asymmetric carbon atoms and, as a result, exist in the form of different optical isomers (enantiomers, diastereomers). The invention includes all optical isomers and their racemic or non-racemic mixtures. Finally, compounds of Formula (I) can exist as endo/exo-isomers in case the ring system E is bicyclic. The pure endo- and exo-isomers as well as their mixtures are also comprised by the invention.

Compounds of Formula (I), in which G is a heterocyclic aromatic ring or contains such in an anellated ring system can optionally be present as tautomers when this heterocyclic ring is substituted by free hydroxy-, mercapto- or amino groups. In this case, the invention includes all tautomeric forms.

Subject matter of the invention are further pharmacologically acceptable acid addition salts of the compounds of Formula (I) with inorganic or organic acids. Preferable examples for addition salts with suitable inorganic acids are hydrochlorides, hydrobromides, hydroiodides, sulfates and phosphates. Addition salts of organic acids are preferably acetates, benzoates, citrates, fumarates, gluconates, malates, maleates, methanesulfonates, lactates, oxalates, succinates, tartrates and tosylates.

Compounds of Formula (I) as well as their acid addition salts can also be optionally present as hydrates or other solvates. The invention includes such hydrates and solvates.

In the compounds of Formula (I), the definitions for the atoms or atomic groups preferably have the following meanings:

Halogen means fluorine, chlorine, bromine or iodine;

Alkyl can be straight chained or branched and preferably signifies a $C_1$–$C_6$-alkyl residue, especially a methyl-, ethyl-, propyl-, isopropyl-, butyl-, isobutyl-, sec-butyl-, tert-butyl-, cyclopropylmethyl-, pentyl-, isopentyl-, tert-pentyl-, neopentyl-, cyclopropylethyl-, cyclobutylmethyl- or hexyl group.

Alkylene signifies for example methylene, ethylene, propylene, tetramethylene, pentamethylene, hexamethylene, heptamethylene, octamethylene, nonamethylene or decamethylene.

Alkenyl preferably signifies $C_3$–$C_6$-alkenyl and can be straight chained or branched and preferably signifies an allyl-, 2-butenyl-, 3-butenyl-, 2-methyl-2-propenyl-, 2-pentenyl-, 4-pentenyl-, 2-methyl-2-butenyl-, 3-methyl-2-butenyl-, 2-hexenyl-, 5-hexenyl-, 4-methyl-3-pentenyl- or 2,2-dimethyl-3-butenyl-group.

Alkenylene signifies for example ethenylene, propenylene, butenylene, pentenylene, hexenylene, hexadienylene, heptenylene, octenylene, nonenylene or decenylene.

Alkinyl preferably signifies $C_2$–$C_6$-alkinyl which can be straight chained or branched and can preferably signify an ethinyl-, propargyl-, 2-butinyl-, 3-butinyl-, 4-pentinyl-, 5-hexinyl- or 4-methyl-2-pentinyl group.

Alkinylene signifies for example propinylene, butinylene, pentinylene, hexinylene, hexeninylene, heptinylene, octinylene, noninylene or decinylene.

Cycloalkyl is preferably a $C_3$–$C_8$-cycloalkyl residue, especially a cyclopropyl-, cyclobutyl-, cyclopentyl-, cyclohexyl-, cycloheptyl- or cyclooctyl group.

Hydroxyalkyl contains a hydroxyl group in one of the above mentioned alkyl residues, especially in a $C_1$–$C_6$-alkyl residue, whereby among the $C_1$–$C_6$-hydroxyalkyl residues, the hydroxymethyl- and the hydroxyethyl residue are preferred.

Aside from the oxygen atom, alkoxy, alkenyloxy, alkinyloxy contain one of the above mentioned preferred $C_1$–$C_6$-alkyl-, $C_3$–$C_6$-alkenyl- and/or $C_3$–$C_6$-Alkinyl groups. Particularly preferred groups for this are the methoxy-, ethoxy-, isopropoxy-, tert-butoxy-, allyloxy- and propargyloxy groups.

Alkoxy, especially $C_1$–$C_6$-alkoxy, entirely or partially replaced by fluorine is for example difluoromethoxy, trifluoromethoxy or 2,2,2-trifluoroethoxy.

Aside from the sulphur atom, alkylthio, alkenylthio, alkinyl thio contain one of the above mentioned preferred $C_1$–$C_6$-alkyl-, $C_3$–$C_6$-alkenyl- or $C_3$–$C_6$-alkinyl groups. Preferred groups among these are the methylthio, ethylthio-, isopropylthio- and tert-butylthio groups.

Cyclopentyloxy- and cyclopentylthio- and/or cyclohexyloxy- and cyclohexylthio residues represent preferred $C_3$–$C_8$-cyclo-alkyloxy and $C_3$–$C_8$-cycloalkylthio.

Aside from the oxygen atom, alkanoyloxy groups preferably contain an aliphatic acyl group with 1 to 7 carbon atoms.

Among preferred alkanoyloxy groups are the acetoxy-, propionyloxy- and pivaloyloxy groups.

Alkoxycarbonyl groups, preferably $C_2$–$C_7$-alkoxycarbonyl groups contain, aside from the carbonyl group, one of the above mentioned alkoxy groups, especially $C_1$–$C_6$-alkoxy groups. Preferred alkoxycarbonyl groups are the methoxycarbonyl-, ethoxycarbonyl-, isopropoxycarbonyl-, isobutoxycarbonyl- and tert-butoxycarbonyl groups.

Aside from the oxygen atom, alkoxycarbonyloxy groups preferably contain one of the above mentioned $C_2$–$C_7$-alkoxycarbonyl residues. Among preferred alkoxycarbonyl groups are the methoxycarbonyloxy-, ethoxycarbonyloxy-, isopropoxycarbonyloxy-, isobutoxycarbonyloxy- and tert-butoxycarbonyl groups as well as allyloxycarbonyloxy groups.

Aside from the carbonyl group, alkylaminocarbonyl, especially $C_2$–$C_7$-alkylaminocarbonyl and dialkylaminocarbonyl groups, preferably $C_3$–$C_{13}$-dialkylaminocarbonyl groups, contain an alkylamino- and/or dialkylamino residue whose alkyl groups correspond especially to the $C_1$–$C_6$-alkyl groups of the above description. Preferred groups are the dimethylaminocarbonyl-diethylaminocarbonyl and diisopropylamino-carbonyl groups.

Aside from the unsubstituted amino group, the amino group of the Formula $NR^5R^6$ is one of the below mentioned alkylamino groups, especially $C_1$–$C_6$-alkylamino groups and/or dialkyl-amino groups, especially di-($C_1$–$C_6$-alkyl) amino groups.

Alkylamino especially contains one of the above mentioned $C_1$–$C_6$-alkyl groups. Preferred groups are the methylamino-, ethylamino-, propylamino-, isopropylamino-, butylamino-, and the tert-butylamino groups.

The preferred di-($C_1$–$C_6$-alkyl)amino residue carries two of the same or different of the above mentioned $C_1$–$C_6$-alkyl groups on the nitrogen atom. Preferred groups are the dimethylamino-, diethylamino-, dipropylamino-, diisopropylamino-, isopropyl-, methylamino-, dibutylamino- or tert-butylmethylamino groups.

Acyl, especially $C_1$–$C_6$-acyl, signifies the residue of an aliphatic saturated or unsaturated, straight chained, branched or cyclic carboxylic acid. Preferred acyl residues are formyl-, acetyl-, propionyl-, acryloyl-, butyryl-, isobutyryl-, methacryloyl-, cyclopropylcarbonyl-, pentanoyl-, pivaloyl-, cyclobutylcarbonyl-, hexanoyl- and dimethylacryloyl groups.

Alkanesulfonyl, especially $C_1$–$C_6$-alkanesulfonyl is preferably the methanesulfonyl-, ethanesulfonyl-, propanesulfonyl-, butanesulfonyl-, pentanesulfonyl- or hexanesulfonyl groups.

Saturated or unsaturated, preferably four- to eight-membered heterocycles with one or two hetero-atoms, are for example azetidine, tetrahydrofuran, tetrahydrothiophene, pyrrolidine, tetrahydropyran, tetrahydropyridine, piperidine, tetrahydroazepine, hexahydroazepine, octahydroazocine, pyrazolidine, piperazine, morpholine, thiomorpholine, thiomorpholin-1,1-dioxide, hexahydrodiazepine or hexahydrooxazepine.

Preferred monocyclic aromatic five- or six-membered heterocycles with one to three hetero-atoms are for example furyl, thienyl, pyrrolyl, oxazolyl, isoxazolyl, thiazolyl, isothiazolyl, imidazolyl, pyrazolyl, oxadiazolyl, thiadiazolyl, triazolyl, pyridyl, pyrazinyl, pyridazinyl, pyrimidinyl or triazinyl.

Anellated bi- and tricyclic aromatic or partially hydrated carbocyclic ring systems with 8 to 16 ring atoms and at least one aromatic ring are preferably benzocyclobutyl, indanyl, indenyl, naphthyl, dihydronaphthyl, tetrahydronaphthyl, biphenylenyl, fluoroenyl, anthryl, dihydroanthryl, phenanthryl, dihydrophenanthryl, dibenzocycloheptenyl, dihydrodibenzocycloheptenyl, dihydrodibenzocyclooctenyl or tetrahydrodibenzocyclooctenyl. Their mono- or dioxo- derivates, i.e. for example the residues of indanone, tetralone, anthrone, anthraquinone, fluoroenone, phenanthrone, dibenzocycloheptenone, dihydrodibenzocycloheptenone or tetrahydrodibenzocyclooctenone are also to be understood as partially hydrated carbocyclic ring systems.

Anellated bi- and tricyclic aromatic or partially hydrated heterocyclic ring systems with 8 to 16 ring atoms and at least one aromatic ring are, for example, imidazothiazolyl, benzofuryl, dihydrobenzofuryl, benzothienyl, dihydrobenzothienyl, indolyl, indolinyl, isoindolinyl, benzimidazolyl, indazolyl, benzooxazolyl, benzoisoxazolyl, benzothiazolyl, benzoisothiazolyl, benzofurazanyl, benzothiadiazolyl, benzotriazolyl, oxazolopyridyl, thiazolopyridyl, isothiazolopyridyl, imidazopyridyl, pyrazclopyridyl, thienopyrimidinyl, chromanyl, benzopyranyl, quinolyl, isoquinolyl, dihydroquinolyl, tetrahydroquinolyl, benzodioxanyl, quinoxalinyl, quinazolinyl, naphthyridinyl, carbazolyl, tetrahydrocarbazolyl, pyridoindolyl, acridinyl, phenanthridinyl, dihydrophenanthridinyl, dibenzoisoquinolinyl, dihydrodibenzoisoquinolinyl, phenothiazinyl, dihydrodibenzooxepinyl, benzocycloheptathienyl, dihydrothienobenzothiepinyl, dihydrodibenzothiepinyl, octahydrodibenzothiepinyl, dibenzoazepinyl, dihydrodibenzoazepinyl, octahydrodibenzoazepinyl, benzocycloheptapyridyl, dihydrobenzocycloheptapyridyl, pyridobenzoazepinyl, dihydropyridobenzoazepinyl, dihydropyridobenzodiazepinyl, dihydrodibenzooxazepinyl, dihydropyridobenzooxepinyl, dihydropyridobenzooxazepinyl, dihydrodibenzothiazepinyl or dihydropyridobenzothiazepinyl.

Furthermore, their mono- or dioxo-derivatives and/or optionally their possible tautomers are also to be understood as partially hydrated heterocyclic ring systems, i.e. for example the residues of indolinone, isatin, of benzooxazolone and/or its tautomer hydroxybenzooxazole, of benzisoxazolone, benzothiazolone, benzoisothiazolone and benzimidazolone and/or their corresponding tautomers, hydroxybenzoisoxazole, hydroxybenzothiazole, hydroxybenzoisothiazole and hydroxybenzimidazole, as well as indazolinone, of oxazolopyridinones, thiazolopyridinones, pyrazolopyridinones and imidazopyridinones and/or their corresponding tautomers hydroxyoxazolopyridine, hydroxythiazolopyridine, hydroxypyrazolopyridine and hydroxyimidazopyridine, the residues from the series chromanone, chromone, quinolinone, dihydroquinolinone, tetrahydrocarbazolone, acridone, phenanthridone, benzoisoquinolinone, dihydrodibenzoxepinones, benzocycloheptathiophenones, dihydrothienobenzothiepinones, dihydrodibenzothiepinones, dihydrodibenzoazepinones, benzocycloheptapyridinones, dihydropyridobenzoazepinones, dihydropyridobenzodiazepinones, dihydropyridobenzooxazepinones, dihydrodibenzothiazepinones and of dihydropyridobenzothiazepinones.

Saturated and unsaturated monocyclic, four- to eight-membered heterocycles (as the group —NR$^{13}$R$^{15}$) which, aside from the essential nitrogen atom, can optionally contain one or two further hetero-atoms selected from N and/or S and/or O, are for example azetidine, pyrrolidine, piperidine, (1H)-tetrahydropyridine, hexahydroazepine, (1H)-tetrahydroazepine, octahydroazocine, pyrazolidine, piperazine, hexahydrodiazepine, morpholine, hexahydroxazepine, thiomorpholine or thiomorpholin-1,1-dioxide.

Saturated or unsaturated bi- or tricyclic, anellated or bridged heterocycles with 8 to 16 ring atoms (as the group R$^{13}$R$^{15}$) which, aside from the essential nitrogen atom, can optionally contain one or two further hetero-atoms, selected from N and/or S and/or O, are for example 5-aza-bicyclo[2.1.1]hexane, 2-aza-bicyclo[2.2.1]heptane, 7-aza-bicyclo[2.2.1]heptane, 2,5-diaza-bicyclo[2.2.1]heptane, 2-aza-bicyclo[2.2.2]octane, 8-aza-bicyclo[3.2.1]octane, 2,5-diaza-bicyclo[2.2.2]octane, 9-aza-bicyclo[3.3.1]nonane, indoline, isoindoline, (1H)-dihydroquinoline, (1H)-tetrahydroquinoline, (2H)-tetrahydroisoquinoline, (1H)-tetrahydroquinoxaline, (4H)-dihydrobenzoxazine; (4H)-dihydrobenothiazine, (1H)-tetrahydrobenzo[b]azepine, (1H)-tetrahydrobenzo[c]azepine, (1H)-tetrahydrobenzo[d]azepine, (5H)-tetrahydrobenzo[b]oxazepine, (5H)-retrahydrobenzo[b]thiazepine, 1,2,3,4-tetrahydro-9H-pyrido[3,4-b]indole, (10H)-dihydroacridine, (10H)-dihydrodhenanthridine, 1,2,3,4-tetrahydroacridanone, (10H)-phenoxazine, (10H)-phenothiazine, (5H)-dibenzazepine, (5H)-dihydrodibenzazepine, (5H)-octahydrodibenzazepine, dihydrobenzo[d,e]isoquinoline, (5H)-dihydrodibenzodiazepine, (5H)-benzo[b]pyrido[f]azepine, (5H)-dihydrobenzo[b]pyrido-[f]azepine (11H)-dihydrodibenzo[b,e]oxazepine, (11H)-dihydrodibenzo[b,e]thiazepine, (10H)-dihydrodibenzo[b,f]oxazepine, (10H)-dihydrodibenzo[b,f]thiazepine, (5H)-tetrahydrodibenzazocine, (11H)-dihydrobenzo[e]pyrido[b]-1,4-diazepin-6-one, (11H)-di-hydrobenzo[b]pyrido[e]-1,4-diazepin-5-one.

Concretely, the invention relates to new piperazinyl-substituted compounds of the general Formula (I)

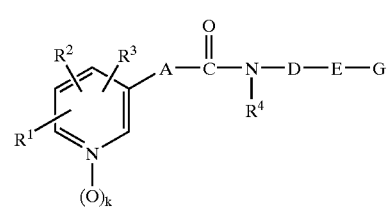

wherein

R$^1$ is selected from hydrogen, hydroxy, halogen, cyano, aminocarbonyl, carboxy, saturated, single or several-fold unsaturated, branched or straight chained or cyclic hydrocarbon residues such as alkyl, alkenyl, alkinyl or cycloalkyl, aryl such as phenyl or heteroaryl such as pyridyl, alkoxy, cycloalkyloxy, alkenyloxy or alkinyloxy or aralkyloxy such as the benzyloxy group, alkoxycarbonyl, alkylaminocarbonyl, dialkylaminocarbonyl, alkanoyloxy, alkoxycarbonyloxy, alkylthio, cycloalkylthio, alkenylthio, alkinylthio, aryloxy such as phenoxy, heteroaryloxy such as pyridyloxy, arylthio such as phenylthio, heteroarylthio such as pyridylthio, trifluoromethyl, hydroxyalkyl, NR$^5$R$^6$, wherein R$^5$ and R$^6$ are selected independent of each other from hydrogen, saturated or unsaturated hydrocarbon residues such as alkyl, alkenyl, alkinyl, or aryl such as phenyl and aralkyl such as benzyl;

R$^2$ is selected from hydrogen, halogen, cyano, saturated hydrocarbon residues such as alkyl, or halogenated hydrocarbon residues such as trifluoromethyl, hydroxy, alkoxy, aralkyloxy residues such as benzyloxy, as well as alkanoyloxy, whereby R$^1$ and R$^2$, in the case that they are immediately adjacent to each other, optionally form a bridge which is selected from —(CH$_2$)$_4$— and —(CH=CH)$_2$— and —CH$_2$O—CR$^7$R$^8$—O—, wherein R$^7$ and R$^8$ are selected independently of each other from hydrogen and alkyl residues;

R$^3$ is selected from hydrogen, halogen, saturated hydrocarbon residues such as alkyl, or halogenated hydrocarbon residues such as trifluoromethyl, or hydroxyalkyl;

R$^4$ is selected from hydrogen, hydroxy, or single or several-fold unsaturated, branched or straight chained or cyclic hydrocarbon residues such as alkyl, alkenyl, alkinyl or cycloalkyl, alkoxy and aralkyloxy such as benzyloxy;

k is 0 or 1;

A is selected from

Alkylene which is optionally substituted one to three-fold by straight chained or branched chained hydrocarbon residues such as alkyl, hydroxy, alkoxy, halogen such as fluorine, or aryl such as phenyl, Alkylene, wherein a methylene unit is isosterically replaced by O, S, $NR^9$, CO, SO or $SO_2$ whereby, with the exception of CO, the isosteric substitution cannot be adjacent to the amide group and, in $NR^9$, the residue $R^9$ is selected from hydrogen, alkyl, alkenyl, alkinyl, acyl or alkanesulfonyl;

Cycloalkylene such as 1,2-cyclopropylene;

Alkenylene which is optionally substituted one to three-fold by alkyl, hydroxy, alkoxy, fluorine, cyano or aryl such as phenyl;

Alkadienylene, which is optionally substituted once or twice by alkyl, fluorine, cyano or aryl such as phenyl, 1,3,5-hexatrienylene, which is optionally substituted by alkyl, fluorine, cyano or aryl such as phenyl, and ethinylene;

D is selected from alkylene, which is optionally substituted once or twice by alkyl, hydroxy, or alkoxy;

alkenylene, which is optionally substituted once or twice by alkyl, hydroxy, or alkoxy;

alkinylene, which is optionally substituted once or twice by alkyl, hydroxy, or alkoxy, as well as alkylene, alkenylene or alkinylene, wherein one to three methylene units is each isosterically replaced by O, S, $NR^{10}$, CO, SO or $SO_2$, wherein $R^{10}$ has the same meaning as $R^9$ but is selected independently thereof;

E

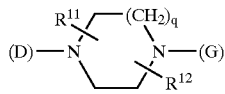

whereby q is 1, 2 or 3;

$R^{11}$ is selected from hydrogen, alkyl, hydroxy, hydroxymethyl, carboxy, or alkoxycarbonyl and $R^{12}$ is selected from hydrogen, alkyl or an oxo group immediately adjacent to a nitrogen atom or $R^{11}$ and $R^{12}$, optionally together, form an alkylene bridge under formation of a bicyclic ring system;

G is selected from G1, G2, G3, G4 or G5, wherein $G^1$ is

whereby r has the meaning 0 to 3, s is 0 or 1;

$R^{13}$ is selected from hydrogen, alkyl, alkenyl, alkinyl, cycloalkyl;

saturated or unsaturated, four to eight-membered heterocycles which can contain one or two hetero-atoms that are selected from N and/or S and/or O;

benzyl, phenyl;

monocyclic aromatic five- or six-membered heterocycles which can contain 1 to 3 hetero-atoms that are selected from N and/or S and/or O and are either directly bound or bound over a methelyene group;

anellated bi- and tricyclic aromatic or partially hydrated carbocyclic ring systems with 8 to 16 ring atoms and at least one aromatic ring, whereby the bond can occur either over an aromatic or a hydrated ring and either directly or over a methylene group;

anellated bi- and tricyclic aromatic or partially hydrated heterocyclic ring systems with 8 to 16 ring atoms and at least one aromatic ring, whereby one to three ring atoms can be selected from N and/or S and/or O and the bond can occur either over an aromatic or a hydrated ring and either directly or over a methylene group;

$R^{14}$ has the same meaning as $R^{13}$ but is selected independently thereof;

$R^{15}$ is selected from hydrogen, hydroxy, $C_1$–$C_3$-alkyl, aralkyl such as benzyl or aryl such as phenyl, monocyclic aromatic five or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, with the exception of compounds in which G has the meaning

in the case that the following substitutents are simultaneously signify $R^{13}$ pyridyl or (optionally halogen-, alkyl-, alkoxy- or Trifluoromethyl-substituted) phenyl, $R^{14}$ hydrogen or (phenyl optionally substituted with halogen-, alkyl-, alkoxy- or Trifluoro methyl, $R^{15}$ is hydrogen, and A represents alkylene, optionally substituted ethenylene or butadienylene, D alkylene or alkenylene as well as E piperazine or homopiperazine and

S=1;

$G^2$ is selected from

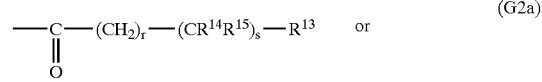

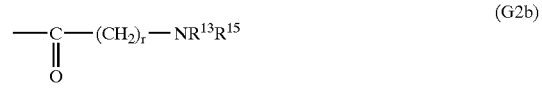

whereby r and s as well as the substitutents $R^{13}$ to $R^{15}$ can have the above meaning, or the grouping

can also be a nitrogen heterocycle bound over the nitrogen atom selected from saturated or unsaturated monocyclic, four to eight-membered heterocycles, which aside from the essential nitrogen atom, can still optionally contain one or two further hetero-atoms selected from N and/or S and/or O, or saturated or unsaturated bi- or tricyclic, anellated or bridged heterocycles with 8 to 16 ring atoms, chat aside from the essential nitrogen atom, can optionally still contain one or two further hetero-atoms that are selected from N and/or S and/or O;

$G^3$ has the meaning

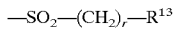 (G3)

wherein r and $R^{13}$ have the above definition, $G^4$ has the meaning

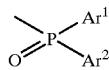 (G4)

whereby $Ar^1$ and $Ar^2$ can be selected independently from each other from phenyl, pyridyl or naphthyl;

$G^5$ has the meaning

 (G5)

whereby $R^{16}$ is selected from trifluoromethyl, alkoxy, alkenyloxy, and aralkyloxy such as benzyloxy, whereby aromatic ring systems in the substitutents $R^1$, $R^2$, $R^4$, $R^5$, $R^6$, $R^{13}$, $R^{14}$, $R^{15}$, $R^{16}$, $Ar^1$ and $Ar^2$ and/or in the ring system —$NR^{13}R^{15}$ can be substituted independently from each other by one to three of the same or different groups selected from halogen, cyano, alkyl, halogen alkyl such as trifluoromethyl, cycloalkyl, aryl such as phenyl, arylalkyl such as benzyl; hydroxy, hydroxy alkyl, alkoxy, alkoxy entirely or partially substituted by fluorine, aralkyloxy such as benzyloxy, aryloxy such as phenoxy; mercapto, alkylthio, carboxy, carboxyalkyl, carboxyalkenyl, alkoxycarbonyl, aralkyloxycarbonyl such as benzyloxycarbonyl, nitro, amino, monoalkylamino, dialkylamino and in the case of two adjacent residues on the aromatic ring, also methylendioxy, and whereby alkyl-, alkenyl- and cycloalkyl residues in the groups $G^1$, $G^2$ and $G^3$ can be substituted by one or two of the same or different groups which are selected from hydroxy, carboxy, alkoxycarbonyl, aralkyloxycarbonyl such as benzyloxycarbonyl, amino, monoalkylamino and dialkylamino;

their cis- and trans-isomers, E- and Z-isomers, especially in case that A is a cyclopropane ring or D contains one or more double bonds, including the enantiomers, diastereomers and other isomers as well as their racemic or non-racemic mixtures and the corresponding endo- and exo-isomers for the case that the ring system E is bicyclic;

their tautomers;

their acid addition salts including their hydrates and solvates.

Furthermore, the invention relates to preferred pyridylalkane, pyridylalkene and pyridylalkine carboxamides of the Formula (I)

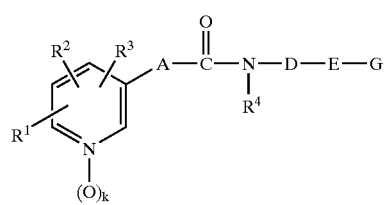 (I)

wherein the substitutents have the following meanings:

$R^1$ is selected from hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from hydrogen, $C_1$–$C_6$-alkyl, $C_3$–$C_6$-alkenyl, $C_3$–$C_6$-alkinyl, benzyl and phenyl;

$R^2$ is selected from hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^1$ and $R^2$, if adjacent, optionally form a bridge selected from

—$(CH_2)_4$— and —$(CH=CH)_2$— or —$CH_2O$—$CR^7R^8$—O—, wherein $R^7$ and $R^8$ are selected independently from each other from hydrogen and $C_1$–$C_6$-alkyl;

$R^3$ is selected from hydrogen, halogen, $C_1$–$C_6$-alkyl, trifluoronethyl and $C_1$–$C_6$-hydroxyalkyl;

$R^4$ is selected from hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1,

A is selected from $C_1$–$C_6$-alkylene, optionally substituted one to three-fold by $C_1$–$C_3$-alkyl., hydroxy, $C_1$–$C_3$-alkoxy, fluorine, or phenyl, $C_2$–$C_6$-alkylene, in which a methylene unit is isosterically replaced by O, S, $NR^9$, CO, SO or $SO_2$, whereby, with the exception of CO, the isosteric substitution cannot be adjacent to the amide group and, in $NR^9$, the residue R9 is selected from hydrogen, $C_1$–$C_6$alkyl, $C_3$–$C_6$-alkenyl, $C_3$–$C_6$-alkinyl, $C_1$–$C_6$-acyl or $C_1$–$C_6$-alkanesulfonyl, 1,2-cyclopropylene, $C_2$–$C_6$-Alkenylene, optionally substituted once to threefold by $C_1$–$C_3$-alkyl, hydroxy, $C_1$–$C_3$-alkoxy, fluorine, cyano or phenyl, $C_4$–$C_6$-alkadienylene, optionally substituted once or twice by $C_1$–$C_3$-alkyl, fluorine, cyano or phenyl;

1,3,5-hexatrienylene, optionally substituted by $C_1$–$C_3$alkyl, fluorine, cyano or phenyl, and ethinylene D is selected from
  $C_2$–$C_{10}$-alkylene, optionally substituted once or twice by $C_1$–$C_6$-alkyl, hydroxy, or $C_1$–$C_6$-alkoxy;
  $C_4$–$C_{10}$-alkenylene, optionally substituted once or twice by $C_1$–$C_6$-alkyl, hydroxy, or $C_1$–$C_6$-alkoxy;
  $C_4$–$C_{10}$-alkinylene, optionally substituted once or twice by $C_1$–$C_6$-alkyl, hydroxy, or $C_1$–$C_6$-alkoxy; as well as
  $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO or $SO_2$, whereby
  $R^{10}$ has the same meaning as $R^9$, but is selected independently thereof;
E signifies

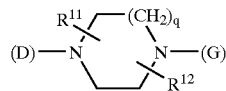

whereby
q has the meaning 1, 2 or 3;
$R^{11}$ is selected from
  hydrogen, $C_1$–$C_6$-alkyl, hydroxy, hydroxymethyl, carboxy, or $C_2$–$C_7$-alkoxycarbonyl and
$R^{12}$ is selected from
  hydrogen, $C_1$–$C_6$-alkyl or an oxo group adjacent to a nitrogen atom, or $R^{11}$ and $R^{12}$ optionally together, form a $C_1$–$C_3$-alkylene bridge under formation of a bicyclic ring system;
G is selected from G1, G2, G3, G4 or G5, whereby
$G^1$ represents

  (G1)

r has the meaning 0 to 3,
s is 0 or 1 and
$R^{13}$ is selected from
  hydrogen, $C_1$–$C_6$-alkyl, $C_3$–$C_6$-alkenyl, $C_3$–$C_6$-alkinyl, $C_3$–$C_8$-cycloalkyl;
  saturated or unsaturated, four to eight-membered heterocycles, which can contain one or two heteroatoms that are selected from N and/or S and/or O;
  benzyl, phenyl;
  monocyclic aromatic five or six-membered heterocycles, which can contain one to three hetero-atoms selected from the group N and/or S and/or O and are either bound directly or over a methylene group,
  anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
  anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group,
$R^{14}$ has the same meaning as $R^{13}$, but is selected independently thereof;
$R^{15}$ is selected from
  hydrogen, hydroxy, methyl, benzyl, phenyl,
  monocyclic aromatic five or six-membered heterocycles, which can contain one to three hetero-atoms from the group N and/or S and/or O and are either bound directly or over a methylene group,
  anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group,
  anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group,
whereby G in the form of $G^1$ cannot have the meaning

  (G1)

in the case that the following substitutions simultaneously signify
  $R^{13}$ pyridyl or (optionally halogen-, alkyl-, alkoxy- or Trifluoromethyl- substituted) phenyl,
  $R^{14}$ hydrogen or (phenyl optionally substituted with halogen-, alkyl-, alkoxy- or trifluoro methyl,
  $R^{15}$ is hydrogen, and
  A represents alkylene, optionally substituted ethenylene or butadienylene,
  D alkylene or alkenylene as well as
  E piperazine or homopiperazine and
  s=1;
$G^2$ is selected from

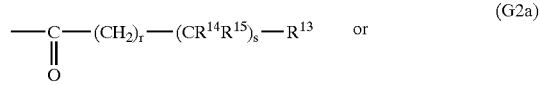  (G2a)

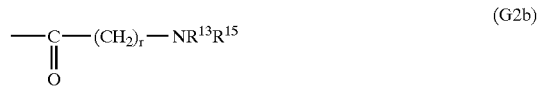  (G2b)

whereby r and s as well as the substitutents $R^{13}$ to $R^{15}$ can have the above meaning, or the grouping

can also be a nitrogen heterocycle bound over the nitrogen atom selected from
  saturated or unsaturated monocyclic, four to eight-membered heterocycles, which aside from the essential nitrogen atom, can optionally still contain one or two further hetero-atoms selected from N and/or S and/or O, or
  saturated or unsaturated bi- or tricyclic, anellated or bridged heterocycles with 8 to 16 ring atoms, that aside from the essential nitrogen atom, can optionally still contain one or two further hetero-atoms that are selected from N and/or S and/or O;
$G^3$ has the meaning

  (G3)

wherein r and $R^{13}$ have the above definition, $G^4$ has the meaning

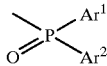
(G4)

whereby
$Ar^1$ and $Ar^2$ can be selected independently from each other from phenyl, pyridyl or naphthyl;
$G^5$ has the meaning

   (G5)

$R^{16}$ is selected from trifluoromethyl, $C_1$–$C_6$-alkoxy, $C_3$–$C_6$-alkenyloxy, and benzyloxy, whereby aromatic ring systems in the substitutents are $R^1$, $R^2$, $R^4$, $R^5$, $R^6$, $R^{13}$, $R^{14}$, $R^{15}$, $R^{16}$, $Ar^1$ and $Ar^2$ and/or in the ring system —$NR^{13}R^{15}$ can be substituted independently from each other by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and whereby alkyl-, alkenyl- and cycloalkyl residues in the groups $G^1$, $G^2$ and $G^3$ can be substituted by one or two of the same or different groups which are selected from hydroxy, carboxy, $C_2$–$C_7$-alkoxycarbonyl, benzyloxycarbonyl, amino, mono-$C_1$–$C_6$-alkylamino and di-(C—$C_6$-alkyl-amino);

their cis- and trans-isomers, E- and Z-isomers, especially in case that A is a cyclopropane ring or D contains one or more double bonds, including the enantiomers, diastereomers and other isomers as well as their racemic or non-racemic mixtures and the corresponding endo- and exo-isomers for the case that the ring system E is bicyclic;

their tautomers;

their acid addition salts including their hydrates and solvates.

According to a further preferred embodiment, the invention relates to compounds of the general Formula (I), whereby $R^1$ is selected from hydrogen, halogen, cyano, $C_1$–$C_6$-alkyl, trifluoromethyl, $C_3$–$C_8$-cycloalkyl, $C_1$–$C_6$-hydroxyalkyl, hydroxy, $C_1$–$C_4$-alkoxy, benzyloxy, $C_1$–$C_4$-alkylthio, $C_1$–$C_5$-alkanoyloxy, $C_1$–$C_4$-alkylthio, $C_2$–$C_5$-alkoxycarbonyl, aminocarbonyl, $C_2$–$C_5$-alkylaminocarbonyl, $C_3$–$C_9$-dialkylaminocarbonyl, carboxy, phenyl, phenoxy, phenylthio, pyridyloxy, and $NR^5R^6$, whereby $R^5$ and $R^6$ are selected independently from each other from hydrogen and $C_1$–$C_6$-alkyl;

$R^2$ is selected from hydrogen, halogen, cyano, $C_1$–$C_6$-alkyl, trifluoromethyl, hydroxy, $C_1$–$C_4$-alkoxy;

$R^3$ is selected from hydrogen, halogen and $C_1$–$C_6$-alkyl.

$R^4$ is selected from hydrogen, $C_1$–$C_6$-alkyl, $C_3$–$C_6$-alkenyl, $C_3$–$C_6$-cycloalkyl, hydroxy, $C_1$–$C_6$-alkoxy and benzyloxy;

k has the meaning 0 or 1,

A is selected from $C_1$–$C_6$-alkylene, optionally substituted one to three-fold by $C_1$–$C_3$-alkyl, hydroxy, fluorine, or phenyl, $C_2$–$C_6$-alkylene, in which a methylene unit is isosterically replaced by O, S, $NR^9$, CO, SO or $SO_2$, whereby, with the exception of CO, the isosteric substitution cannot be adjacent to the amide group and, in $NR^9$, the residue $R^9$ is selected from hydrogen, $C_1$–$C_6$-alkyl, $C_1$–$C_6$-acyl or methanesulfonyl;

1,2-cyclopropylene, $C_2$–$C_6$-Alkenylene, optionally substituted once to three-fold by $C_1$–$C_3$-alkyl, hydroxy, fluorine, cyano or phenyl, $C_4$–$C_6$-alkadienylene, optionally substituted once to two-fold by $C_1$–$C_3$-alkyl, fluorine, cyano or phenyl;

1,3,5-hexatrienylene, optionally substituted by $C_1$–$C_3$-alkyl, fluorine, cyano, and ethinylene D is selected from $C_2$–$C_{10}$-alkylene, optionally substituted once or twice by $C_1$–$C_3$-alkyl or hydroxy;

$C_4$–$C_{10}$-alkenylene, optionally substituted once or twice by $C_1$–$C_3$-alkyl or hydroxy;

$C_4$–$C_{10}$-alkinylene, optionally substituted once or twice by $C_1$–$C_3$-alkyl or hydroxy; as well as $C_2$–$C_{10}$-alkylene, $C_4$–$C_{10}$-alkenylene or $C_4$–$C_{10}$-alkinylene, in which one to three methylene units is each isosterically replaced by O, S, $NR^{10}$, CO, SO or $SO_2$, whereby $R^{10}$ has the same meaning as $R^9$, but is selected independently thereof;

E signifies

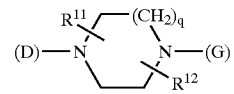

whereby q has the meaning 1, 2 or 3;

$R^{11}$ is selected from hydrogen, $C_1$–$C_3$-alkyl, hydroxy, hydroxymethyl, carboxy, or $C_2$–$C_7$-alkoxycarbonyl and $R^{12}$ is selected from hydrogen or an oxo group adjacent to a nitrogen atom or $R^{11}$ and $R^{12}$, optionally together, form a $C_1$–$C_3$-alkylene bridge under formation of a bicyclic ring system;

G is selected from G1, G2, G3, G4 or G5, whereby $G^1$ represents

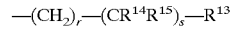   (G1)

r has the meaning 0 to 2, s is 0 or 1 and $R^{13}$ is selected from hydrogen, $C_1$–$C_6$-alkyl, $C_3$–$C_6$-alkenyl, $C_3$–$C_6$-alkinyl, $C_3$–$C_8$-cycloalkyl; benzyl, phenyl;

monocyclic aromatic five or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group, $R^{14}$ has the same meaning as $R^{13}$, but is selected independently thereof;

$R^{15}$ is selected from hydrogen, hydroxy, methyl, benzyl, phenyl;

monocyclic aromatic five or six-membered heterocycles, which can contain one to three hetero-atoms selected from the group N and/or S and/or O and are either bound directly or over a methylene group, anellated bi- and tricyclic aromatic or partially hydrated carbocyclic ring systems with 8 to 16 ring atoms and at least one aromatic ring, wherein the linkage can occur either over an aromatic or a hydrated ring and either directly or over a methylene group, anellated bi- and tricyclic aromatic or partially hydrated heterocyclic ring systems with 8 to 16 ring atoms and at least one aromatic ring, wherein one to three ring atoms can be selected from N and/or S and/or O and the linkage can occur either over an aromatic ring or a hydrated ring and either directly or over a methylene group;

$C^2$ is selected from

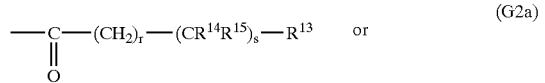 (G2a)

 (G2b)

whereby r and s as well as the substitutents $R^{13}$ to $R^{15}$ can have the above meaning, or the grouping

can also be a nitrogen heterocycle bound over the nitrogen atom selected from saturated or unsaturated monocyclic, four to eight-membered heterocycles, which, aside from the essential nitrogen atom, can optionally still contain one or two further hetero-atoms selected from N and/or S and/or O, or saturated or unsaturated bi- or tricyclic, anellated or bridged heterocycles with 8 to 16 ring atoms, that aside from the essential nitrogen atom, can optionally still contain one or two further hetero-atoms that are selected from N and/or S and/or O;

$G^3$ has the meaning

 (G3)

wherein r and $R^{13}$ have the above definition, $G^4$ has the meaning

 (G4)

whereby $Ar^1$ and $Ar^2$ can be selected independently from each other from phenyl, pyridyl or naphthyl;

$G^5$ has the meaning

 (G5)

$R^{16}$ is selected from trifluoromethyl, $C_1$–$C_6$-alkoxy, $C_3$–$C_6$-alkenyloxy, and benzyloxy, whereby aromatic ring systems in the substitutents are $R^1$, $R^2$, $R^4$, $R^5$, $R^6$, $R^{13}$, $R^{14}$, $R^{15}$, $R^{16}$, $Ar^1$ and $Ar^2$ and/or in the ring system —$NR^{13}R^{15}$ can be substituted independently from each other by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$alkoxycarbonyl, benzyloxycarbonyl, nitro, amino, mono-$C_1$–$C_6$-alkylamino, di-(C—$C_6$-alkyl)-amino and, methylene dioxide in the case of two adjacent residues on the aromatic ring, whereby alkyl-, alkenyl- and cycloalkyl residues in the groups $G^1$, $G^2$ and $G^3$ can be substituted by one or two of the same or different groups which are selected from hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

According to a further embodiment, the invention especially relates to compounds of the general Formula (1), wherein $R^1$ is selected from hydrogen, halogen, cyano, methyl, ethyl, trifluoromethyl, hydroxy, $C_1$–$C_4$-alkoxy, benzyloxy, $C_1$–$C_5$-alkanoyloxy, methylthio, ethylthio, methoxycarbonyl, tert-butoxycarbonyl aminocarbonyl, carboxy, phenoxy, and phenylthio $R^2$ is selected from hydrogen, halogen, trifluoromethyl, hydroxy;

$R^3$ is selected from hydrogen, halogen;

$R^4$ is selected from hydrogen, $C_1$–$C_3$-alkyl, allyl, hydroxy and $C_1$–$C_3$-alkoxy;

k is 0 or 1;

A is selected from $C_1$–$C_6$-alkylene, optionally substituted once or twice by $C_1$–$C_3$-alkyl, hydroxy or fluorine;

$C_2$–$C_6$-alkylene, in which a methylene unit is isosterically replaced by O, S, $NR^9$, CO, SO or $SO_2$, whereby, with the exception of CO, the isosteric substitution cannot be adjacent to the amide group;

$C_2$–$C_6$-alkylene, optionally substituted once or twice by $C_1$–$C_3$ alkyl, hydroxy and/or fluorine;

$C_4$–$C_6$-alkadienylene, optionally substituted by $C_1$–$C_3$-alkyl or one or two fluorine atoms;

1,3,5-hexatrienylene, optionally substituted by fluorine;

D is selected from
- $C_2$–$C_8$-alkylene, optionally substituted once or twice by methyl or hydroxy;
- $C_4$–$C_8$-alkenylene, optionally substituted once or twice by methyl or hydroxy;
- $C_4$–$C_8$-alkinylene, optionally substituted once or twice by methyl or hydroxy; and
- $C_2$–$C_8$-alkylene, $C_4$–$C_8$-alkenylene or $C_4$–$C_8$-alkinylene, wherein one to three methylene units are each isosterically replaced by O, S, NH, $N(CH_3)$ $N(COCH_3)$, $N(SO_2CH_3)$, CO, SO or $SO_2$, whereby E has the meaning

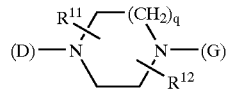

whereby
q is 1 or 2;
$R^{11}$ is selected from
hydrogen, $C_1$–$C_3$-alkyl, hydroxymethyl, or carboxy, and
$R^{12}$ is selected from
hydrogen or an oxo group adjacent to a nitrogen atom
G is selected from G1, G2. G3, G4 or G5, whereby
$G^1$ represents

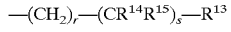

r is 0 to 2 and,
s is 0 or 1; and
$R^{13}$ is selected from
hydrogen, $C_1$–$C_6$-alkyl, $C_3$–$C_8$-cycloalkyl; benzyl, phenyl;

benzocyclobutyl, indanyl, indenyl, oxoindanyl, naphthyl, dihydronaphthyl, tetrahydronaphthyl, oxotetrahydronaphthyl, biphenylenyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptenyl, oxodibenzocycloheptenyl, dihydrodibenzocycloheptenyl, oxodihydrodibenzocycloheptenyl, dihydrodibenzocyclooctenyl, tetrahydrodibenzocyclooctenyl or oxotetrahydrodibenzocyclooctenyl bound directly or over a methylene group;

furyl, thienyl, pyrrolyl, oxazolyl, isoxazolyl, thiazolyl, iso-thiazolyl, pyrazolyl, imidazolyl, oxadiazolyl, thiadiazolyl, triazolyl, pyridyl, pyrazinyl, pyridazinyl, pyrimidinyl, triazinyl, imidazothiazolyl, benzofuryl, dihydrobenzofuryl, benzothienyl, dihydrobenzothienyl, indolyl, indolinyl, isoindolinyl, oxoindolinyl, dioxoindolinyl, benzoxazolyl, oxobenzooxazolinyl, benzoisoxazolyl, oxobenzoisoxazolinyl, benzothiazolyl, oxobenzthiazolinyl, benzoisothiazolyl, oxobenzoisothiazolinyl, benzoimidazolyl, oxobenzoimidazolinyl, indazolyl, oxoindazolinyl, benzofurazanyl, benzothiadiazolyl, benzotriazolyl, oxazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinoloyl, isoquinoloyl, dihydrquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, oxotetrahydrocarbazolyl, pyridoindolyl, acridinyl, oxodihydroacridinyl, phenanthridinyl, dihydrophenanthridinyl, oxodihydrophenanthridinyl, dibenzoisoquinolinyl, dihydrodibenzoisoquinolinyl, oxodihydrodibenzoisoquinolinyl, phenothiazinyl, dihydrodibenzooxepinyl, oxodihydrodibenzooxepinyl, benzocycloheptathienyl, oxobenzocycloheptathienyl, dihydrothienobenzothiepinyl, oxodihydrothienobenzothiepinyl, dihydrodibenzothiepinyl, oxodihydrodibenzothiepinyl, octahydrodibenzothiepinyl, dibenzoazepinyl, dihydrodibenzoazepinyl, oxodihydrodibenzoazepinyl, octahydrodibenzoazepinyl, benzocycloheptapyridyl, oxobenzocycloheptapyridyl, pyridobenzoazepinyl, dihydropyridobenzoazepinyl, oxodihydropyridobenzoazepinyl, dihydropyridobenzodiazepinyl, dihydrodibenzooxazepinyl, dihydropyridobenzooxepinyl, dihydropyridobenzooxazepinyl, oxodihydropyridobenzooxazepinyl, dihydrodibenzothiazepinyl, oxodihydrodibenzothiazepinyl, dihydropyridobenzothiazepinyl or oxodihydropyridobenzothiazepinyl bound directly or over a methylene group;

$R^{14}$ is synonymous with $R^{13}$ but is selected independent thereof;
$R^{15}$ is selected from
hydroxy, methyl, benzyl, phenyl, indanyl, indenyl, naphthyl, dihydronaphthyl, tetrahydronaphthyl, furyl, thienyl, pyrrolyl, oxazolyl, isoxazolyl, thiazolyl, isothiazolyl, pyrazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzooxazolyl, benzothiazolyl, benzoimidazolyl, chromanyl, quinolyl or tetrahydroquinolyl bound directly or over a methylene group;
$G^2$ is selected from

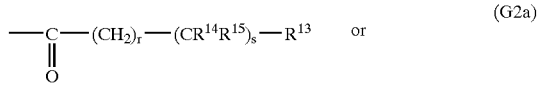 (G2a)

 (G2b)

whereby r and s and the substituents $R^{13}$ to $R^{15}$ can have the above meaning, or the grouping

represents the ring of azetidine bound over the nitrogen or one of the following residues: pyrrolidine, piperidine, (1H)-tetrahydropyridine, hexahydroazepine, (1H)-tetrahydroazepine, octahydroazocine, pyrazolidine, piperazine, hexahydrodiazepine, morpholine, hexahydrooxazepine, thiomorpholine, thiomorpholin-1,1-dioxide, of 5-aza-bicyclo-[2.1.1]hexane, 2-aza-bicyclo[2.2.1]heptane, 7-aza-bicyclo-[2.2.1]heptane, 2,5-diaza-bicyclo[2.2.1]heptane, 2-aza-bicyclo[2.2.2]octane, 8-aza-bicyclo[3.2.1]octane, 2,5-diaza-bicyclo[2.2.2]octane, 9-aza-bicyclo[3.3.1]nonane, indoline, isoindoline, (1H)-dihydroquinoline, (1H)-tetrahydroquinolin, (2H)-tetrahydroisoquinoline, (1H)-tetrahydroquinoxaline, (4H)-dihydrobenzooxazine, (4H)-dihydrobenzothiazine, (1H)-tetrahydrobenzo[b]azepine, (1H)-tetrahydrobenzo[c]azepine, (1H)-tetrahydro-benzo[d]azepine, (5H)-tetrahydrobenzo[b]ox-azepine, (5H)-tetrahydrobenzo[b]thiazepine, 1,2,3,4-tetra-hydro-9H-pyrido[3,4-b]indole, (10H)-dihydroacridine, (10H)-dihydrophenanthridine, 1,2,3,4-tetrahydroacridanone, (10H)-phenoxazine, (10H)-phenothiazine, (5H)-dibenzoazepine, (5H)-dihydrodibenzoazepine, (5H)-octahydrodibenzoazepine, dihydrobenzo[d,e]isoquinoline, (5H)-dihydrodibenzodiazepine, (5H)-benzo[b]pyrido-[f]azepine, (5H)-Dihydrobenzo[b]pyri-do[f]azepine, (11H)-Dihydrodibenzo[b,e]oxazepine, (1H)-dihydrodibenzo[b,e]thiazepine, (10H)-dihydrodibenzo[b,f]-oxazepine, (10H)-dihydrodibenzo[b,f]thiazepine, (5H)-tetra-hydrodibenzoazocine, (11H)-dihydrobenzo[e]pyrido[b]-1,4-diazepin-6-one or (11H)-Dihydrobenzo[b]pyrido[e]-1-1,4-diazepin-5-one.

G³

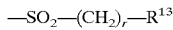  (G3)

wherein r and R¹³ have the above definition,
G⁴ has the meaning

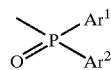  (G4)

whereby
Ar¹ and Ar² are selected independently from each other from phenyl, pyridyl or naphthyl;
G⁵ has the meaning

—COR¹⁶  (G5)

R¹⁶ is selected from
trifluoromethyl, $C_1$–$C_6$-alkoxy, $C_3$–$C_6$-alkenyloxy, and benzyloxy,
whereby aromatic ring systems in the substitutents can be substituted independently from each other by one to three of the same or different groups selected from
halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide in the case of two adjacent residues on the aromatic ring, and
whereby alkyl-, alkenyl- and cycloalkyl residues in the groups G¹, G² and G³ can be substituted by one or two of the same or different groups which are selected from
hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

According to a further very preferred embodiment, the invention relates to compounds of Formula (I), wherein
R¹ is selected from hydrogen, fluorine, chlorine, bormine, methyl, ethyl, trifluoromethyl, hydroxy, $C_1$–$C_4$-alkoxy, methylthio, ethlylthio, carboxy and phenoxy;
R² is selected from hydrogen, chlorine and methyl;
R³ is hydrogen;
R⁴ is selected from hydrogen, $C_1$–$C_3$-alkyl and hydroxy,
k is 0
A is selected from $C_2$–$C_6$-alkylene, which is optionally substituted once or twice by hydroxy or fluorine;
$C_2$–$C_6$-alkylene, wherein a methylene unit is isosterically replaced by O, S or CO, whereby, with the exception of CO, the isosteric substitution cannot be adjacent to the amide group;
$C_2$–$C_6$-alkenylene which is optionally substituted by $C_1$–$C_3$-alkyl and/or fluorine;
$C_4$–$C_6$-alkadienylene;
D is selected from
$C_2$–$C_8$-alkylene which is optionally substituted by methyl or hydroxy;
$C_4$–$C_8$-alkenylene, which is optionally substituted by hydroxy;
$C_4$–$C_8$-alkinylene, which is optionally substituted by hydroxy;
$C_2$–$C_8$-alkylene, $C_4$–$C_8$-alkenylene, $C_4$–$C_8$-alkinylene wherein a methylene unit is respectively isosterically replaced by O, NH, N(CH₃), CO or SO₂ or an ethylene group is isosterically replaced by a group NH—CO and/or CO—NH or a propylene group is isosterically replaced by a group NH—CO—O and/or O—CO—NH;
E is selected from piperazine or hexahydro-1,4-diazepine (homopiperazine), wherein the ring can be optionally substituted by one or two metheyene groups and/or by an oxo group adjacent to a nitrogen atom;
G is selected from hydrogen, $C_3$–$C_8$-cycloalkyl, methoxycarbonyl, tert-butoxycarbonyl, benzyloxycarbonyl, trifluoroacetyl, diphenylphosphinoyl, or a group

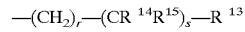

and

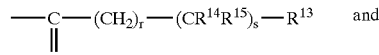

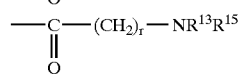

and

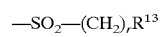

wherein
r has the meaning 0 or 1
s is 0 or 1,
R¹³ is selected from hydrogen, methyl, benzyl, phenyl, indanyl, indenyl, oxoindanyl, naphthyl, tetrahydronaphthyl, fluorenyl, oxofluorenyl, anthryl, dihydroanthryl, oxodihydroanthryl, dioxodihydroanthryl, phenanthryl, dihydrophenanthryl, oxydihydrophenanthryl, dibenzocycloheptenyl, dihydrodibenzocycloheptenyl, oxodihydrodibenzocycloheptyl bound directly or over a methylene group, furyl, thienyl, oxazolyl, isooxazoly, thiazolyl, imidazolyl, oxadiazolyl, pyridyl, pyrazinyl, pyrimidinyl, imidazothiazolyl, benzofuryl, benzothienyl, indolyl, indolinyl, oxoindolinyl, dioxoindolinyl, benzoxazolyl, oxobenzoxoazolinyl, benzothiazolyl, oxobenzthiazolinyl, benzimidazolyl, oxobenzimidazolinyl, indazolyl, benzofurazanyl, benzotriazolyl, oxazolopyridyl, oxodihydrooxazolopyridyl, thiazolopyridyl, oxodihydrothiazolopyridyl, imidazopyridyl, oxodihydroimidazopyridyl, chromanyl, chromanonyl, benzopyranyl, chromonyl, quinolyl, isoquinolyl, oxodihydroquinolinyl, tetrahydroquinolyl, oxotetrahydroquinolinyl, benzodioxanyl, quinazolinyl, carbazolyl, acridinyl, dihydroacridinyl, oxodihydroacridinyl, dihydrophenanthridinyl dihydrobenzo isoquinolinyl, phenothiazinyl, dihydrodibenzoxepinyl, benzocycloheptathienyl, dihydrothienobenzothiepinyl, dihydrodibenzothiepinyl, oxodihydrodibenzothiepinyl, dihydrodibenzoazepinyl, oxodihydrodibenzoazepinyl, octahydrodibenzoazepinyl, benzocycloheptapyridyl, dihydropyridobenzodiazepinyl, dihydrodibenzothiazepinyl bound directly or over a methylene group, $R^{14}$ is selected from hydrogen, methyl, benzyl, phenyl;

$R^{15}$ is selected from hydrogen, hydroxy, methyl, benzyl, phenyl;

naphthyl, tetrahydronaphthyl, furyl, thienyl, oxazolyl, thiazolyl, imidazolyl, pyridyl, benzofuryl, benzothienyl, indolyl, indolinyl, benzoxazolyl, benzothiazolyl, benzimidazolyl, chromanyl, quinolyl or tetrahydroquinolyl bound directly or over a methylene group;

whereby the grouping —$NR^{13}R^{15}$ represents a ring bound over the nitrogen atom of a residue from the series pyrrolidine, piperidine, hexahydroazepine, piperazine, hexahydrodiazepine, morpholine, hexahydroxazepine, thiomorpholine, 7-aza-bicyclo[2,2.1]heptane, 2,5-diazabicyclo[2.2.1]heptane, indoline, isoindoline, (1H)-dihydroquinoline, (1H)-tetrahydroquinoline, (2H)-tetrahydroisoquinoline, (4H)-dihydrobenzoxazine, (4H)-dihydrobenzothiazine, (1H)-tetrahydrobenzo[b]azepine, (1H)-tetrahydrobenzo[d]azepine. (5H)-tetrahydrobenzo[b]oxazepine, (5H)-tetrahydrobenzo[b]thiazepine, (10H)-dihydroacridine, 1,2,3,4-tetrahydroacridanone, (10H)-dihydrophenanthridine, (1H)-dihydrobenzo-[d,e]isoquinoline, (10H)-phenothiazine, (5H)-dibenzo[b,f]azepine, (5H)-dihydrodibenzo[b,f]azepine, (5H)-dihydrodibenzo[c,e]azepine, (5H)-dihydrodibenzodiazepine, (11H)-dihydrodibenzo[b,e]oxazepine (11H)-dihydrodibenzo[b,e]thiazepine, (5H)-dihydrobenzo[b]pyrido[3,2-f]azepine and (11H)-6-oxodihydrobenzo[e]pyrido[3,2-b][1,4]diazepine, and whereby aromatic ring systems in the substituents can be substituted, independently of each other, by one to three of the same or different groups selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy which can be entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carbocyalkenyl, $C_2$–$C_7$-alkoxycarbonyl, benzyloxycarbonyl, nitro, amino, mono-$C_1$–$C_6$-alkylamino or di-($C_1$–$C_6$-alkyl)-amino, and in the case of two adjacent residues on the aromatic ring, methylenedioxy, and whereby alkyl, alkenyl and cycloalkyl residues in the group G can be substituted by one or two of the same or different groups which are selected from hydroxy, carboxy, $C_2$–$C_7$-alkoxycarbonyl, benzyloxycarbonyl, amino, mono-$C_1$–$C_6$-alkylamino and ki-($C_1$–$C_6$-alkyl) amino.

Furthermore, according to a particularly preferred embodiment, the invention relates to compounds of formula (I), wherein $R^1$ is selected from hydrogen, fluorine, methyl, trifluoromethyl ethylthio;

$R^2$, $R^3$ and $R^4$ are each hydrogen;

k has the meaning 0;

A is selected from ethylene, propylene or butylene which are each optionally substituted by hydroxy or one or two fluorine atoms; or $OCH_2$, $SCH_2$;

ethenylene, or 1,3-butadienylene;

D is selected from $C_2$–$C_6$-alkylene which is optionally substituted by hydroxy;

$C_4$–$C_6$ alkenylene;

$C_4$–$C_6$ alkinylene; or $C_2$–$C_6$ alkylene, $C_4$–$C_6$ alkenylene or $C_4$–$C_6$ alkinylene, wherein one or two methylene units is isosterically replaced by O, NH, CO or $SO_2$;

E is selected from piperazine or hexahydro-1,4-diazeazepine;

G is selected from phenyl, benzyl, phenethyl, diphenylmethyl, naphthyl, tetrahydronaphtyl, naphthylmethyl, fluorenyl fluorenylmethyl, anthrylmethyl, dihydrodibenzocycloheptenyl;

furylmethyl, thienylmethyl, thiazolylmethyl, pyridylmethyl, benzothienylmethyl, quinolylmethyl, phenylthienylmethyl, phenylpyridylmethyl, benzocycloheptapyridinyl, dihydrobenzocycloheptapyridinyl, dihydrodibenzooxepinyl, dihydrodibenzothiepinyl, dihydrodibenzoazepinyl, dihdrobenzopyridodiazepinyl;

formyl, acetyl, pivaloyl, phenylacetyl, diphenylacetyl, diphenylpropionyl, naphthylacetyl, benzoyl, naphthoyl, oxofluorenylcarbonyl, oxodihydroanthrylcarbonyl, dioxodihydroanthrylcarbonyl, furoyl, pyridylacetyl, pyridylcarbonyl, chromonylcarbonyl, quinolylcarbonyl, phenylylaminocarbonyl, naphthylaminocarbonyl, tetrahydronaphthylaminacarbonyl, dibenzylaminocarbonyl, benzylphenylaminocarbonyl, diphenylaminocarbonyl, indolinyl-N-carbonyl, isoindolin-N-carbonyl, tetrahydroquinolinyl-N-carbonyl, carbazolyl-N-carbonyl, tetrahydrobenzoazepinyl-N-carbonyl, dihydrodibenzoazepin-N-carbonyl, dihydrobenzopyridoazepinyl-N-carbonyl, oxodihydrobenzopyridoazepinyl-N-carbonyl;

methanesulfonyl, toluenesulfonyl, naphthylsulfonyl, quinolinsulfonyl and diphenylphosphinoyl, wherein aromatic ring systems can be substituted independently of each other by one to three of the same or different groups which are selected from halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino or di-($C_1$–$C_6$-alkyl)-amino, and in the case of two adjacent residues in the aromatic ring methylenedioxy, and whereby alkyl, alkenyl and cycloalkyl residues in the group G can be substituted by one or two of the same or different groups which are selected from hydroxy, carboxy, $C_2$–$C_7$-alkoxycarbonyl, benzyloxycarbonyl, amino, mono-$C_1$–$C_6$-alkylamino or di-($C_1$–$C_6$-alkyl)-amino.

The following end products represent very particular concrete preferred embodiments of the invention:

a) N-[4-(4-diphenylmethylpiperazin-1-yl)-3-hydroxybutyl]-3-pyridin-3-yl-acrylamide N-(3-(4-diphenylmethylpiperazin-1-yl)-propoxy]-3-pyridin-3-yl-acrylamide;
N-[4-(4-diphenylmethylpiperazin-1-yl)-4-oxo-butyl]-3-pyridin-3-yl-acrylamide;
N-[3-(4-diphenylmethylpiperazin-1-sulfonyl)-propyl]-3-pyridin-3-yl-acrylamide;
N-{2-[2-(4-diphenylmethylpiperazin-1-yl)-ethoxy]-ethyl}-3-pyridin-3-yl-acrylamide;
N-(4-{4-[bis-(4-fluorphenyl)-methyl]-piperazin-1-yl}-but-2-in-yl)-3-pyridin-3-yl-acrylamide;
N-{4-[4-(4-carboxyphenyl-phenylmethyl)-piperazin-1-yl]-butyl}-3-pyridin-3-yl-acrylamide and
N-(4-{4-[(4-aminophenyl)-phenylmethyl]-piperazin-1-yl}-butyl)-3-pyridin-3-yl-acrylamide.

b) N-{4-[4-(9H-fluoren-9-yl)-piperazin-1-yl]-butyl}-2-(pyridin-3-yloxy)-acetamide N-{5-[4-(9H-fluoren-9-yl)-piperazin-1-yl]-pentyl}-3-pyridin 3-yl-acrylamide;
N-{6-[4-(9H-fluoren-9-yl)-piperazin-1-yl]-hexyl}-3-pyridin-3-yl-acrylamide;
3-pyridin-3-yl-N-{4-[4-(1,2,3,4-tetrahydronaphthalin-1-yl)-piperazin-1-yl]-butyl}-acrylamide;
3-pyridin-3-yl-N-{4-[4-(5,6,7,8-tetrahydronaphthalin-1-yl)-piperazin-1-yl]-butyl}-acrylamide and
N-{4-[4-(naphthalin-1-yl)-piperazin-1-yl]-butyl}-3-pyridin-3-yl-acrylamide.

c) N-[4-(4-biphenyl-2-yl-piperazin-1-yl)-butyl]-3-pyridin-3-yl-propionamide

N-[5-(4-biphenyl-2-yl-piperazin-1-yl)-pentyl]-3-pyridin-3-yl-acrylamide;
N-[6-(4-biphenyl-2-yl-piperazin-1-yl)-hexyl]-3-pyridin-3-yl-acrylamide;
N-[4-{4-biphenyl-2-yl-piperazin-1-ly}-butyl]-2-(pyridin-3-yloxy)-acetamide as well as
N-[4-(4-biphenyl-2-yl-piperazin-1-yl)-butyl]-5-(pyridin-3-yl)-penta-2,4-diensäureamide.

d) N-{4-[4-(10,11-dihydro-5H-dibenzo[a,d]cyclohepten-5-yl)-piperazin-1-yl]-butyl}-3-pyridin-3-yl-propionamide N-{5-[4-(10,11-dihydro-5H-dibenzo[a,d]cyclohepten-5-yl)-piper-azin-1-yl]-pentyl}-3-pyridin-3-yl-acrylamide;
N-{6-[4-(10,11-dihydro-5H-dibenzo[a,d]cyclohepten-5-yl)-piper-azin-1-yl]-hexyl}-3-pyridin-3-yl-acrylamide;
N-{4-[4-(10,11-dihydro-5H-dibenzo[a,d]cyclohepten-5-yl)-piper-azin-1-yl)-butyl}-5-(pyridin-3-yl)-penta-2,4-diens äureamide;
N-{4-[4-(6,11-dihydro-dibenzo[b,e]oxepin-11-yl)-piperazin-1-yl]-butyl-3-pyridin-3-yl-propionamide and
N-{2-[4-(6,11-dihydrodibenzo[b,e]thiepin-11-yl)-piperazin-1-yl]-ethyl}-3-pyridin-3-yl-acrylamide.

e) N-[4-(4-diphenylacetyl-piperazin-1-yl)-butyl]-3-pyridin-3-yl-acrylamide

N-[4-(4-benzoylpiperazin-1-yl)-butyl]-3-pyridin-3-yl-acrylamide;
N-{4-[4-(2-aminobenzoyl)-piperazin-1-yl]-butyl}-3-pyridin-3-yl-acrylamide;
N-{4-[4-(4-carboxybenzoyl)-piperazin-1-yl]-butyl}-3-pyridin-3-yl-acrylamide;
N-{4-[4-(biphenyl-2-carbonyl)-piperazin-1-yl]-butyl}-3-pyridin-3-yl-acrylamide;
N-{4-[4-(9-oxo-9H-fluoren-4-carbonyl)-piperazin-1-yl]-butyl}-3-pyridin-3-yl-acrylamide and
N-{4-[4-(furan-2-carbonyl)-piperazin-1-yl]-butyl}-3-pyridin-3-yl-acrylamide.

f) N-{4-[4-(naphthalin-1-yl-aminocarbonyl)-piperazin-1-yl]butyl}-3-pyridin-3-yl-propionamide N-{4-[4-(diphenylaminocarbonyl)-piperazin-1-yl]-butyl}-3-pyridin-3-yl-acrylamide;
N-{4-[4-(naphthalin-2-sulfonyl)-piperazin-1-yl]-butyl}-3-pyridin-3-yl-acrylamide as well as
N-[4-(4-diphenylphosphinonyl-piperazin-1-yl)-butyl]-3-pyridin-3-yl-acrylamide.

g) N-[4-(4-biphenyl-2-yl-piperazin-1-yl)-butyl]-3-pyridin-3-yl-acrylamide

N-{4-[4-(9H-fluoren-9-yl)-piperazin-1-yl]-butyl}-3-pyridin-3-yl-acrylamide and
N-{4-[4-(10,11-dihydro-5H-dibenzo[a d)cyclohepten-5-yl)-piper-azin-1-yl]-butyl}-3-pyridin-3-yl-acrylamide.

In the following a series of compounds with the respective specific substituent definitions are listed in Table I without any limitation for further illustration of the compounds according to the invention.

TABLE 1

Exemplifying compounds of formula (I) according to the invention

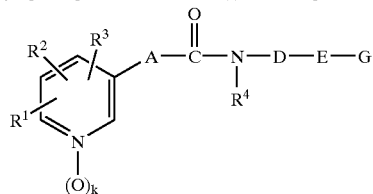

| Nr | R¹–R³ | k | A | R⁴ | D—E—G |
|---|---|---|---|---|---|
| 1 | H | 0 | $CH_2CH_2$ | H | $CH_2CH_2CH_2CH_2$–piperazine-NH |
| 2 | H | 0 | CH=CH | H | $CH_2CH_2CH_2CH_2$–piperazine-NH |
| 3 | H | 0 | CH=CH | H | $CH_2CH_2CH_2CH_2$–piperazine–N–propargyl |
| 4 | H | 0 | CH=CH | H | $CH_2CH_2CH_2CH_2$–piperazine–N–$CH_2CH_2$COOH |
| 5 | H | 0 | $CH_2CH_2$ | H | $CH_2CH_2CH_2CH_2$–piperazine–N–$CH_2CH_2$C(O)O-benzyl |
| 6 | H | 0 | CH=CH | H | $CH_2CH_2CH_2CH_2$–piperazine–N–$CH_2CH_2$NH-isopropyl |
| 7 | H | 0 | CH=CH | H | $CH_2CH_2CH_2CH_2$–piperazine–N–$CH_2$-cyclopropyl |
| 8 | H | 0 | $CH_2CH_2$ | H | $CH_2CH_2CH_2CH_2CH_2$–piperazine–N–cyclopentyl |
| 9 | H | 0 | $CH_2CH_2$ | H | $CH_2CH_2CH_2CH_2$–piperazine–N–$CH_2CH_2$-morpholine |
| 10 | H | 0 | CH=CH | H | $CH_2C{\equiv}CCH_2$–piperazine–N–$CH_2$-phenyl |

TABLE 1-continued

Exemplifying compounds of formula (I) according to the invention

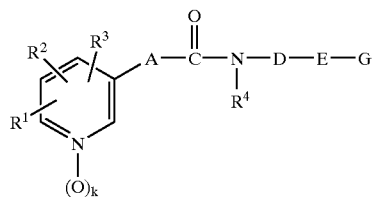

| Nr | R¹–R³ | k | A | R⁴ | D—E—G |
|----|-------|---|-----|----|-------|
| 11 | H | 0 | OCH₂ | H | CH₂CH₂CH₂CH₂—N(3-CH₃ piperazine)N—CH₂—phenyl |
| 12 | H | 0 | CH₂CH₂ | H | CH₂CH₂OCH₂CH₂—N(piperazine)N—CH₂—phenyl |
| 13 | H | 0 | △ (cyclopropyl) | H | CH₂CH₂CH₂CH₂—N(piperazine)N—CH₂CH₂—phenyl |
| 14 | H | 0 | CH=CH | H | CH₂CH₂—N(piperazine)N—CH₂CH₂CH(OH)—phenyl |
| 15 | H | 0 | CH=CH | H | CH₂CH₂CH₂CH₂—N(piperazine)N—CH₂—phenyl-COOH |
| 16 | H | 0 | CH=CH | H | CH₂CH₂CH₂CH₂—N(piperazine)N—CH₂—biphenyl |
| 17 | H | 0 | CH=CH | H | CH₂CH₂CH₂CH₂—N(piperazine)N—CH₂—biphenyl-COOH |
| 18 | H | 0 | CH=CH | H | CH₂CH₂CH₂CH₂—N(piperazine)N—CH₂—naphthyl |

TABLE 1-continued

Exemplifying compounds of formula (I) according to the invention

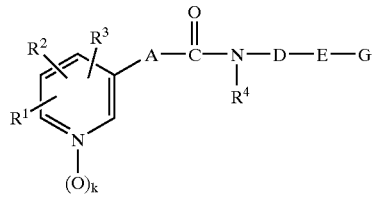

| Nr | R¹–R³ | k | A | R⁴ | D—E—G |
|----|-------|---|---|----|-------|
| 19 | H | 0 | CH$_2$CH$_2$ | H | CH$_2$CH$_2$CH$_2$CH$_2$CH$_2$—N(piperazine)N—CH$_2$-(9-fluorenyl) |
| 20 | H | 0 | CH$_2$CH$_2$ | H | CH$_2$CH$_2$CH$_2$CH$_2$—N(piperazine)N—CH$_2$-(9-anthracenyl) |
| 21 | H | 0 | OCH$_2$ | H | CH$_2$CH$_2$—N(piperazine)N—CH$_2$-(2-pyridyl) |
| 22 | H | 0 | CH=CH | H | CH$_2$CH$_2$CH$_2$CH$_2$—N(piperazine)N—CH$_2$-(2-quinolinyl) |
| 23 | H | 0 | CH=CH—CH=CH | H | CH$_2$CH$_2$CH$_2$CH$_2$—N(piperazine)N—CH(cyclohexyl)(phenyl) |
| 24 | H | 0 | OCH$_2$ | H | CH$_2$CH$_2$—N(piperazine)N—CH(C$_6$H$_5$)$_2$ |
| 25 | H | 0 | CH$_2$NHCH$_2$CH$_2$ | H | CH$_2$CH$_2$—N(piperazine)N—CH(C$_6$H$_5$)$_2$ |
| 26 | H | 0 | C≡C | H | CH$_2$CH$_2$CH$_2$—N(piperazine)N—CH(C$_6$H$_5$)$_2$ |

TABLE 1-continued

Exemplifying compounds of formula (I) according to the invention $$R^2 \underset{R^1}{\overset{R^3}{\diagdown}} \underset{N}{\diagup} A - \underset{\|}{\overset{O}{C}} - \underset{R^4}{N} - D - E - G$$
$$(O)_k$$

| Nr | R¹–R³ | k | A | R⁴ | D—E—G |
|----|-------|---|-----|-----|-------|
| 27 | H | 0 | OCH₂ | H | CH₂CH₂CH₂CH₂—N(piperazine)N—CH(C₆H₅)₂ |
| 28 | H | 0 | CH=CH | H | CH₂C≡CCH₂—N(piperazine)N—CH(C₆H₅)₂ |
| 29 | H | 0 | CH=CH | H | CH₂CH₂CH(OH)CH₂—N(piperazine)N—CH(C₆H₅)₂ |
| 30 | H | 0 | CH=CH | H | OCH₂CH₂CH₂—N(piperazine)N—CH(C₆H₅)₂ |
| 31 | H | 0 | CH=CH | H | CH₂CH₂CH₂C(=O)—N(piperazine)N—CH(C₆H₅)₂ |
| 32 | H | 0 | CH=CH | H | CH₂CH₂CH₂SO₂—N(piperazine)N—CH(C₆H₅)₂ |
| 33 | H | 0 | CH=CH | H | CH₂CH₂NH—C(=O)—N(piperazine)N—CH(C₆H₅)₂ |
| 34 | H | 0 | SCH₂ | H | CH₂CH₂CH₂CH₂—N(piperazine)N—CH(C₆H₅)₂ |
| 35 | H | 0 | CH=CH | H | CH₂CH₂OCH₂CH₂—N(piperazine)N—CH(C₆H₅)₂ |
| 36 | H | 0 | CH=CH | H | CH₂CH₂CH₂C≡CCH₂—N(piperazine)N—CH(C₆H₅)₂ |
| 37 | H | 0 | CH=CH | H | CH₂C≡C—CH=CHCH₂—N(piperazine)N—CH(C₆H₅)₂ |
| 38 | H | 0 | CH=CH | H | CH₂CH₂CH₂CH₂—N(2,5-dimethylpiperazine)N—CH(C₆H₅)₂ |

TABLE 1-continued

Exemplifying compounds of formula (I) according to the invention

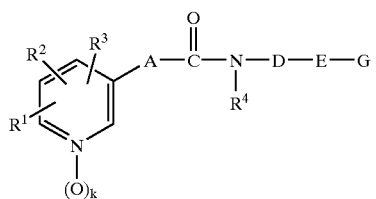

| Nr | R¹–R³ | k | A | R⁴ | D—E—G |
|----|-------|---|-----|----|-------|
| 39 | H | 0 | CH=CH | H | CH₂CH₂CH₂CH₂—N(piperazine with CH₂OH)—CH(C₆H₅)₂ |
| 40 | H | 0 | CH=CH | H | CH₂CH₂CH₂CH₂—N(piperazine with CH₃OOC)—CH(C₆H₅)₂ |
| 41 | H | 0 | CH=CH | H | CH₂CH₂CH₂CH₂—N(piperazinone)—CH(C₆H₅)₂ |
| 42 | H | 0 | CH=CH | H | CH₂CH₂CH₂CH₂—N(diazabicyclic)—CH(C₆H₅)₂ |
| 43 | H | 0 | OCH₂ | H | CH₂CH₂CH₂CH₂—N(piperazine)—CH₂CH(C₆H₅)₂ |
| 44 | H | 0 | CH=CH | H | CH₂CH₂—N(piperazine)—CH₂CH₂CH₂CH(C₆H₅)₂ |
| 45 | H | 0 | CH=CH | H | CH₂CH₂CH₂CH₂—N(piperazine)—CH₂CH₂CH₂C(C₆H₅)₂(OH) |
| 46 | 5-F | 0 | CH₂CH(OH) | H | CH₂CH₂CH₂CH₂—N(piperazine)—N—CH(4-F-C₆H₄)₂ |

TABLE 1-continued
Exemplifying compounds of formula (I) according to the invention
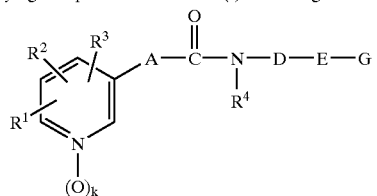
| Nr | R¹–R³ | k | A | R⁴ | D—E—G |
|----|-------|---|------|----|-------|
| 47 | H | 0 | CH=CH | H | CH₂C≡CCH₂—N(piperazine)N—CH(4-F-C₆H₄)(4-F-C₆H₄) |
| 48 | H | 0 | OCH₂ | H | CH₂CH₂CH₂—N(piperazine)N—CH(4-Cl-C₆H₄)(C₆H₅) |
| 49 | H | 0 | △ | H | CH₂CH₂—N(piperazine)N—CH(2-Cl-C₆H₄)(2-Cl-C₆H₄) |
| 50 | H | 0 | CH=CH | H | CH₂CH₂CH(OH)CH₂—N(piperazine)N—CH(2-Cl-C₆H₄)(2-Cl-C₆H₄) |
| 51 | H | 0 | CH=CH | H | CH₂CH₂NH—C(=O)—N(piperazine)N—CH(3-Cl-C₆H₄)(3-Cl-C₆H₄) |

TABLE 1-continued

Exemplifying compounds of formula (I) according to the invention

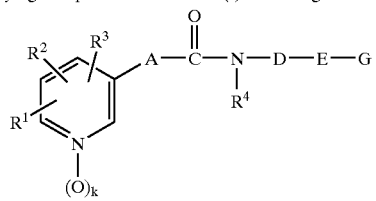

| Nr | R¹–R³ | k | A | R⁴ | D—E—G |
|----|-------|---|------|----|-------|
| 52 | H | 0 | CH=CH | H | CH₂C≡CCH₂—N(piperazine)N—CH(4-Cl-C₆H₄)(4-Cl-C₆H₄) |
| 53 | H | 0 | CH=CH | H | CH₂CH₂CH₂CH₂—N(piperazine)N—CH(4-OH-C₆H₄)(C₆H₅) |
| 54 | H | 0 | CH₂CH₂ | H | CH₂CH₂CH₂CH₂—N(piperazine)N—CH(4-CH₂OH-C₆H₄)(C₆H₅) |
| 55 | H | 0 | CH=CH | H | CH₂CH₂CH₂CH₂—N(piperazine)N—CH(4-COOH-C₆H₄)(C₆H₅) |
| 56 | H | 0 | CH=CH | H | CH₂CH₂CH₂CH₂—N(piperazine)N—CH(4-COOC(CH₃)₃-C₆H₄)(C₆H₅) |

TABLE 1-continued

Exemplifying compounds of formula (I) according to the invention

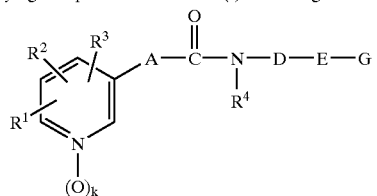

| Nr | R¹–R³ | k | A | R⁴ | D—E—G |
|---|---|---|---|---|---|
| 57 | H | 0 | CH=CH | H | CH₂CH₂—N(piperazine)N—C(phenyl)₃ |
| 58 | 6-C₂H₅S | 0 | CH=CH | H | CH₂CH₂CH₂CH₂—N(piperazine)N—C(phenyl)₃ |
| 59 | H | 0 | △ | H | CH₂CH₂CH₂CH₂—N(piperazine)N—CH(phenyl)(2-pyridyl) |
| 60 | H | 0 | OCH₂ | H | CH₂CH₂CH₂CH₂—N(piperazine)N—CH(phenyl)(3-pyridyl) |
| 61 | 6-CH₃ | 0 | CH=CH | H | CH₂C≡CCH₂—N(piperazine)N—CH(phenyl)(3-pyridyl) |
| 62 | H | 0 | CH=CH | H | OCH₂CH₂CH₂—N(piperazine)N—phenyl |

TABLE 1-continued

Exemplifying compounds of formula (I) according to the invention

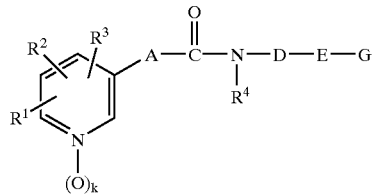

| Nr | R¹–R³ | k | A | R⁴ | D—E—G |
|---|---|---|---|---|---|
| 63 | H | 0 | CH=CH | H | CH₂CH₂—N(piperazine)N—(2-phenylphenyl) |
| 64 | H | 0 | CH₂CH₂ | H | CH₂CH₂CH₂CH₂—N(piperazine)N—(2-phenylphenyl) |
| 65 | H | 0 | CH₂CH₂ | OH | CH₂CH₂CH₂CH₂—N(piperazine)N—(2-phenylphenyl) |
| 66 | H | 0 | CH₂CH₂ | CH₃ | CH₂CH₂CH₂CH₂—N(piperazine)N—(2-phenylphenyl) |
| 67 | H | 0 | CH₂CH₂ | CH₂/CH=CH₂ | CH₂CH₂CH₂CH₂—N(piperazine)N—(2-phenylphenyl) |
| 68 | H | 0 | CH=CH | H | CH₂CH₂CH₂CH₂—N(piperazine)N—(2-phenylphenyl) |
| 69 | H | 1 | CH=CH | H | CH₂CH₂CH₂CH₂—N(piperazine)N—(2-phenylphenyl) |
| 70 | 5-F | 0 | CH=CH | H | CH₂CH₂CH₂CH₂—N(piperazine)N—(2-phenylphenyl) |
| 71 | 6-CH₃ | 0 | CH=CH | H | CH₂CH₂CH₂CH₂—N(piperazine)N—(2-phenylphenyl) |

TABLE 1-continued
Exemplifying compounds of formula (I) according to the invention
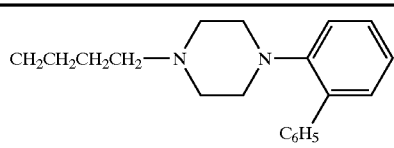
| Nr | R¹–R³ | k | A | R⁴ | D—E—G |
|----|-------|---|---|----|-------|
| 72 | 6-CF$_3$ | 0 | CH=CH | H | 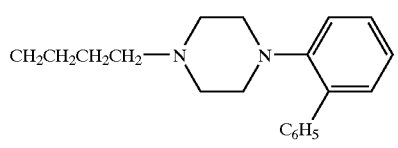 |
| 73 | H | 0 | OCH$_2$ | H | 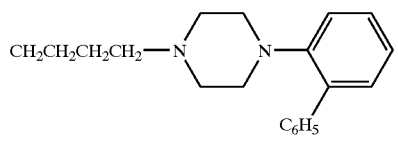 |
| 74 | H | 0 | CH$_2$CH<br>\|<br>OH | H | 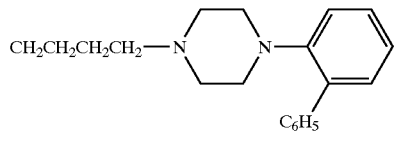 |
| 75 | H | 0 | CH=C<br>\|<br>CH$_3$ | H | 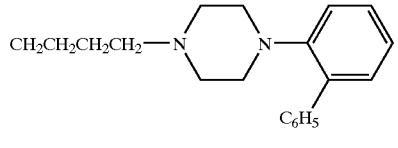 |
| 76 | H | 0 | CH=CH—CH=CH | H | 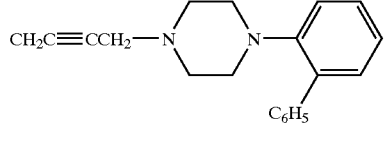 |
| 77 | H | 0 | C=CH<br>\|<br>CH$_3$ | H | 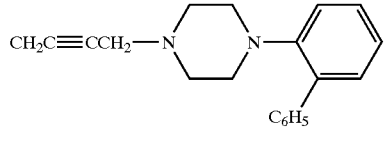 |
| 78 | H | 0 | CH=CH—CH=CH | H | 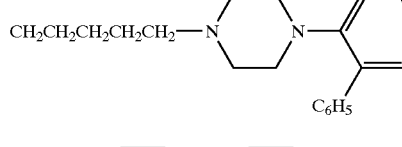 |
| 79 | H | 0 | CH=CH | H | 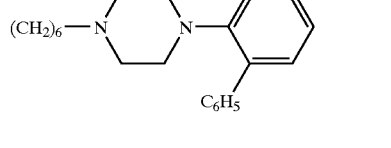 |
| 80 | H | 0 | CH$_2$CH$_2$ | H | (CH$_2$)$_6$—N piperazine—2-phenylphenyl |

TABLE 1-continued

Exemplifying compounds of formula (I) according to the invention

| Nr | R¹–R³ | k | A | R⁴ | D—E—G |
|---|---|---|---|---|---|
| 81 | H | 0 | CH=CH | H | (CH₂)₆—N(piperazine)N—(2-phenylphenyl) |
| 82 | 2-CH₃O | 0 | CH=CH | H | (CH₂)₆—N(piperazine)N—(2-phenylphenyl) |
| 83 | H | 0 | CH=CH | H | CH₂CH₂CH₂CH₂—N(piperazine)N—(4-C₆H₅-phenyl) |
| 84 | 6-CF₃ | 0 | CH=CH | H | CH₂CH₂CH₂CH₂—N(piperazine)N—(4-C₆H₅-phenyl) |
| 85 | H | 0 | CH=CH | H | CH₂CH₂—N(piperazine)N—(1,2,3,4-tetrahydronaphthalen-1-yl) |
| 86 | H | 0 | CH₂CH₂ | H | CH₂CH₂CH₂CH₂—N(piperazine)N—(1,2,3,4-tetrahydronaphthalen-1-yl) |
| 87 | H | 0 | CH=CH | H | CH₂CH₂CH₂CH₂—N(piperazine)N—(1,2,3,4-tetrahydronaphthalen-1-yl) |
| 88 | H | 1 | CH=CH | H | CH₂CH₂CH₂CH₂—N(piperazine)N—(1,2,3,4-tetrahydronaphthalen-1-yl) |
| 89 | 5-CH₃O | 0 | CH=CH | H | CH₂CH₂CH₂CH₂—N(piperazine)N—(1,2,3,4-tetrahydronaphthalen-1-yl) |

TABLE 1-continued

Exemplifying compounds of formula (I) according to the invention

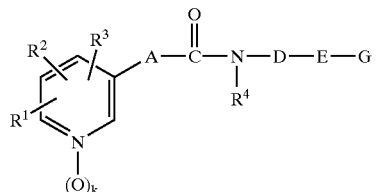

| Nr | R¹–R³ | k | A | R⁴ | D—E—G |
|---|---|---|---|---|---|
| 90 | H | 0 | CH=CH | CH₃ | CH₂CH₂CH₂CH₂—N(piperazine)N-(1,2,3,4-tetrahydronaphthalen-1-yl) |
| 91 | H | 0 | CH=CH—CH=CH | H | CH₂CH₂CH₂CH₂—N(piperazine)N-(1,2,3,4-tetrahydronaphthalen-1-yl) |
| 92 | H | 0 | CH=CH | H | CH₂CH₂CH₂CH₂CH₂—N(piperazine)N-(1,2,3,4-tetrahydronaphthalen-1-yl) |
| 93 | H | 0 | CH₂CH₂ | H | CH₂CH₂CH₂CH₂—N(piperazine)N-(5,6,7,8-tetrahydronaphthalen-1-yl) |
| 94 | H | 0 | CH=CH | H | CH₂CH₂CH₂CH₂—N(piperazine)N-(5,6,7,8-tetrahydronaphthalen-1-yl) |
| 95 | 5-F | 0 | CH=CH | H | CH₂CH=CHCH₂—N(piperazine)N-(5,6,7,8-tetrahydronaphthalen-1-yl) |
| 96 | H | 0 | CH₂CH₂ | H | CH₂CH₂CH₂CH₂—N(piperazine)N-(naphthalen-1-yl) |

TABLE 1-continued

Exemplifying compounds of formula (I) according to the invention

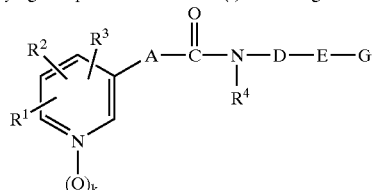

| Nr | R¹–R³ | k | A | R⁴ | D—E—G |
|---|---|---|---|---|---|
| 97 | H | 0 | CH=CH | H | CH₂CH₂CH₂CH₂—N(piperazine)—(naphthalen-1-yl) |
| 98 | H | 0 | CH=CH | H | CH₂CH₂—N(piperazine)—(9H-fluoren-9-yl) |
| 99 | H | 0 | CH₂CH₂ | H | CH₂CH₂CH₂CH₂—N(piperazine)—(9H-fluoren-9-yl) |
| 100 | H | 0 | CH₂CH(OH) | H | CH₂CH₂CH₂CH₂—N(piperazine)—(9H-fluoren-9-yl) |
| 101 | H | 0 | CH=CH | H | CH₂CH₂CH₂CH₂—N(piperazine)—(9H-fluoren-9-yl) |
| 102 | 6-$C_2H_5$S | 0 | CH=CH | H | CH₂CH₂CH₂CH₂—N(piperazine)—(9H-fluoren-9-yl) |

TABLE 1-continued
Exemplifying compounds of formula (I) according to the invention
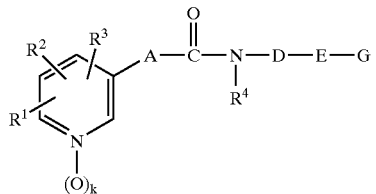
| Nr | R¹–R³ | k | A | R⁴ | D—E—G |
|---|---|---|---|---|---|
| 103 | 5-F | 0 | CH=CH | H | CH₂CH₂CH₂CH₂—N(piperazinyl)-9-fluorenyl |
| 104 | H | 1 | CH=CH | H | CH₂CH₂CH₂CH₂—N(piperazinyl)-9-fluorenyl |
| 105 | H | 0 | CH₂CH₂ | C2H5 | CH₂CH₂CH₂CH₂—N(piperazinyl)-9-fluorenyl |
| 106 | H | 0 | OCH₂ | H | CH₂CH₂CH₂CH₂—N(piperazinyl)-9-fluorenyl |
| 107 | H | 0 | CH=C(CH₃) | H | CH₂CH₂CH₂CH₂—N(piperazinyl)-9-fluorenyl |

TABLE 1-continued
Exemplifying compounds of formula (I) according to the invention
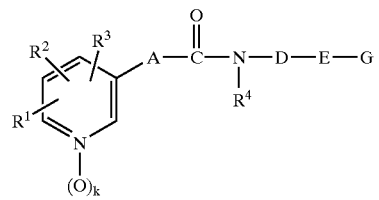
| Nr | R¹–R³ | k | A | R⁴ | D—E—G |
|---|---|---|---|---|---|
| 108 | 6-CH₃ | 0 | CH=CH | H | CH₂CH=CHCH₂—N(piperazine)—N-(9-fluorenyl) |
| 109 | H | 0 | CH=CH—CH=CH | H | CH₂CH=CHCH₂—N(piperazine)—N-(9-fluorenyl) |
| 110 | H | 0 | CH=CH | H | CH₂CH₂CH₂CH₂CH₂—N(piperazine)—N-(9-fluorenyl) |
| 111 | H | 0 | CH=CH | H | CH₂CH₂OCH₂CH₂—N(piperazine)—N-(9-fluorenyl) |
| 112 | 6-C₆H₅O | 0 | CH=CH | H | CH₂CH₂OCH₂CH₂—N(piperazine)—N-(9-fluorenyl) |

TABLE 1-continued

Exemplifying compounds of formula (I) according to the invention

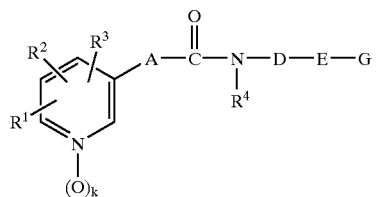

| Nr | R¹–R³ | k | A | R⁴ | D—E—G |
|----|-------|---|---|----|----|
| 113 | H | 0 | CH=CH | H | (CH₂)₆—N(piperazine)—N-fluorenyl |
| 114 | H | 0 | CH=CH | H | CH₂CH₂CH₂CH₂—N(piperazine)—N-(fluorene-COOH) |
| 115 | H | 0 | CH=CH | H | CH₂CH₂—N(piperazine)—N-(10,11-dihydro-5H-dibenzo[a,d]cycloheptenyl) |
| 116 | H | 0 | CH₂CH₂ | H | CH₂CH₂CH₂CH₂—N(piperazine)—N-(10,11-dihydro-5H-dibenzo[a,d]cycloheptenyl) |
| 117 | H | 0 | CH₂CH₂ | OH | CH₂CH₂CH₂CH₂—N(piperazine)—N-(10,11-dihydro-5H-dibenzo[a,d]cycloheptenyl) |

TABLE 1-continued
Exemplifying compounds of formula (I) according to the invention
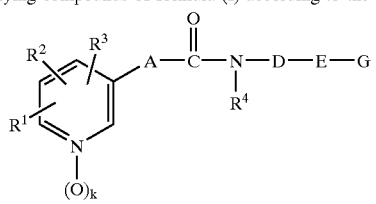
| Nr | R¹–R³ | k | A | R⁴ | D—E—G |
|----|-------|---|---|----|----|
| 118 | H | 0 | CH₂CH(OH) | H |  |
| 119 | H | 0 | CH=CH | H | 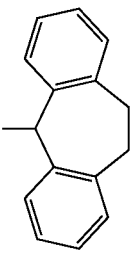 |
| 120 | H | 1 | CH=CH | H | 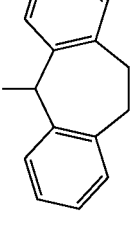 |
| 121 | 2,6-(CH₃)₂ | 0 | CH=CH | H | 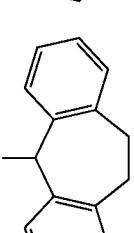 |
| 122 | H | 0 | CH=C(C₆H₅) | H | 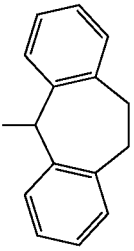 |

TABLE 1-continued
Exemplifying compounds of formula (I) according to the invention
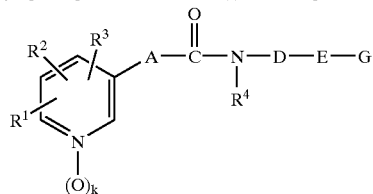
| Nr | R¹–R³ | k | A | R⁴ | D—E—G |
|---|---|---|---|---|---|
| 123 | H | 0 | CH=CH—CH=CH | H | |
| 124 | H | 0 | OCH₂ | H | |
| 125 | H | 0 | CH₂CH₂CH₂CH₂ | H | |
| 126 | H | 0 | CH=CH | H | |
| 127 | H | 0 | CHCH₂ / CH₃ | H | |

TABLE 1-continued

Exemplifying compounds of formula (I) according to the invention

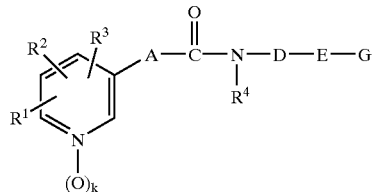

| Nr | R¹–R³ | k | A | R⁴ | D—E—G |
|---|---|---|---|---|---|
| 128 | H | 0 | CH$_2$CH$_2$CH$_2$CH$_2$ | H | OCH$_2$CH$_2$CH$_2$CH$_2$—N(piperazine)—N-(10,11-dihydro-5H-dibenzo[a,d]cyclohepten-5-yl) |
| 129 | H | 0 | CH=CH | H | (CH$_2$)$_6$—N(piperazine)—N-(10,11-dihydro-5H-dibenzo[a,d]cyclohepten-5-yl) |
| 130 | H | 0 | CH=CH | H | CH$_2$CH$_2$CH$_2$CH$_2$—N(piperazine)—N-(1-carboxy-10,11-dihydro-5H-dibenzo[a,d]cyclohepten-5-yl) |
| 131 | H | 0 | CH=CH | H | CH$_2$CH$_2$CH$_2$CH$_2$—N(piperazine)—N-(5H-dibenzo[a,d]cyclohepten-5-yl) |
| 132 | H | 0 | CH=CH | H | CH$_2$CH$_2$CH$_2$CH$_2$—N(piperazine)—N-(dibenzocycloocten-yl) |

TABLE 1-continued

Exemplifying compounds of formula (I) according to the invention

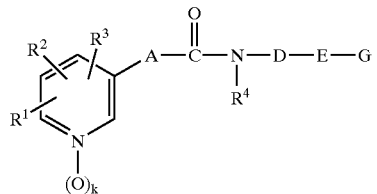

| Nr | R¹–R³ | k | A | R⁴ | D—E—G |
|---|---|---|---|---|---|
| 133 | H | 0 | CH=CH | H | CH₂CH₂CH₂-N(piperazine)N-(4-methylthieno[3,2-d]pyrimidin-4-yl) |
| 134 | H | 0 | CH₂CH₂ | H | CH₂CH₂CH₂-N(piperazine)N-(9H-thioxanthen-9-yl) |
| 135 | H | 0 | CH=CH | H | CH₂CH₂CH₂-N(piperazine)N-(9H-thioxanthen-9-yl) |
| 136 | H | 0 | CH=CH | H | CH₂CH₂CH₂-N(piperazine)N-(4,9-dihydrothieno[2,3-c][2]benzothiepin-4-yl) |
| 137 | H | 0 | CH₂CH₂ | H | CH₂CH₂CH₂-N(piperazine)N-(6,11-dihydrodibenz[b,e]oxepin-11-yl) |

TABLE 1-continued
Exemplifying compounds of formula (I) according to the invention
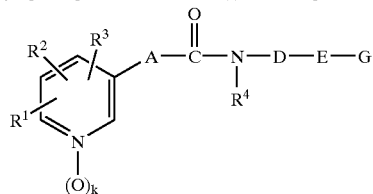
| Nr | R¹–R³ | k | A | R⁴ | D—E—G |
|---|---|---|---|---|---|
| 138 | H | 0 | CH=CH | H | |
| 139 | H | 0 | CH=CH | H | |
| 140 | H | 0 | OCH₂ | H | |
| 141 | H | 0 | CH=CH | H | |
| 142 | H | 0 | CH=CH—CH=CH | H | |

TABLE 1-continued
Exemplifying compounds of formula (I) according to the invention
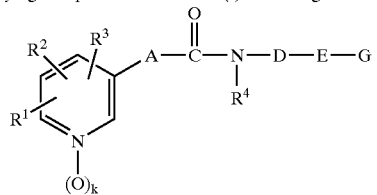
| Nr | R¹–R³ | k | A | R⁴ | D—E—G |
|---|---|---|---|---|---|
| 143 | H | 0 | CH=CH | H | |
| 144 | H | 0 | CH₂CH₂ | H | |
| 145 | H | 0 | CH=CH | H | |
| 146 | H | 0 | CH=CH | H | |

TABLE 1-continued

Exemplifying compounds of formula (I) according to the invention

| Nr | R¹–R³ | k | A | R⁴ | D—E—G |
|---|---|---|---|---|---|
| 147 | H | 0 | CH₂CH₂ | H | CH₂CH₂CH₂CH₂–N(piperazine)–[5H-benzo[5,6]oxepino[3,4-b]pyridin-5-yl] |
| 148 | H | 0 | CH=CH | H | CH₂CH₂CH₂CH₂–N(piperazine)–N–CHO |
| 149 | H | 0 | CH=CH | H | CH₂CH₂CH₂CH₂–N(piperazine)–N–C(=O)CH₃ |
| 150 | H | 0 | CH=CH | H | CH₂CH₂CH₂CH₂–N(piperazine)–N–C(=O)–CH=CH–COOH (fumaroyl) |
| 151 | H | 0 | CH=CH | H | CH₂CH₂CH₂CH₂–N(piperazine)–N–C(=O)–CH=CH–COOH (maleoyl) |
| 152 | H | 0 | CH₂CH₂ | H | CH₂CH₂CH₂CH₂–N(piperazine)–N–C(=O)–C(CH₃)₃ |
| 153 | H | 0 | CH=CH | H | CH₂CH₂CH₂CH₂–N(piperazine)–N–C(=O)–cyclopropyl |
| 154 | H | 0 | CH=CH | H | CH₂CH₂CH₂CH₂–N(piperazine)–N–C(=O)–CH₂–C₆H₅ |
| 155 | H | 0 | CH=CH | H | CH₂CH₂CH₂CH₂–N(piperazine)–N–C(=O)–CH₂CH₂–C₆H₅ |

TABLE 1-continued

Exemplifying compounds of formula (I) according to the invention

| Nr | R¹–R³ | k | A | R⁴ | D—E—G |
|----|-------|---|------|----|-------|
| 156 | H | 0 | OCH₂ | H | CH₂CH₂–N(piperazine)–C(=O)–CH₂–(1-naphthyl) |
| 157 | H | 0 | CH=CH | H | CH₂CH₂CH₂–N(piperazine)–C(=O)–CH₂–(1-naphthyl) |
| 158 | H | 0 | CH=CH | H | CH₂CH₂–N(piperazine)–C(=O)–CH(phenyl)₂ |
| 159 | H | 0 | CH=CH | H | CH₂CH₂CH₂–N(piperazine)–C(=O)–CH(phenyl)₂ |
| 160 | H | 0 | CH=CH | H | CH₂CH₂CH₂–N(piperazine)–C(=O)–CH₂–CH(phenyl)₂ |
| 161 | H | 0 | CH=CH | H | CH₂CH₂CH₂–N(piperazine)–C(=O)–CH₂–(2-thienyl) |
| 162 | H | 0 | CH₂CH₂ | H | CH₂CH₂CH₂–N(piperazine)–C(=O)–CH₂–(4-pyridyl) |

TABLE 1-continued

Exemplifying compounds of formula (I) according to the invention

| Nr | R$^1$–R$^3$ | k | A | R$^4$ | D—E—G |
|---|---|---|---|---|---|
| 163 | H | 0 | CH=CH | H | CH$_2$CH$_2$CH$_2$CH$_2$-piperazine-C(O)-CH$_2$-(1H-indol-3-yl) |
| 164 | H | 0 | CH=CH | H | CH$_2$CH$_2$CH$_2$CH$_2$-piperazine-C(O)-C$_6$H$_5$ |
| 165 | H | 0 | CH$_2$CH$_2$ | H | (CH$_2$)$_6$-piperazine-C(O)-C$_6$H$_5$ |
| 166 | H | 0 | CH=CH | H | (CH$_2$)$_6$-piperazine-C(O)-C$_6$H$_5$ |
| 167 | H | 0 | CH=CH | H | (CH$_2$)$_5$-piperazine-C(O)-C$_6$H$_5$ |
| 168 | H | 0 | CH$_2$CH$_2$ | H | CH$_2$CH$_2$CH$_2$CH$_2$-piperazine-C(O)-C$_6$H$_4$-OH |
| 169 | H | 0 | CH=CH | H | CH$_2$CH$_2$CH$_2$CH$_2$-piperazine-C(O)-C$_6$H$_4$-OH |
| 170 | H | 0 | CH=CH | H | CH$_2$CH$_2$CH$_2$CH$_2$-piperazine-C(O)-C$_6$H$_4$-CH$_2$OH |
| 171 | H | 0 | CH=CH | H | CH$_2$CH$_2$CH$_2$CH$_2$-piperazine-C(O)-C$_6$H$_4$-NH$_2$ |
| 172 | H | 0 | CH=CH | H | CH$_2$CH$_2$CH$_2$CH$_2$-piperazine-C(O)-C$_6$H$_4$-COOH |
| 173 | H | 0 | CH=CH | H | CH$_2$CH$_2$-piperazine-C(O)-C$_6$H$_4$-C$_6$H$_5$ |

TABLE 1-continued

Exemplifying compounds of formula (I) according to the invention

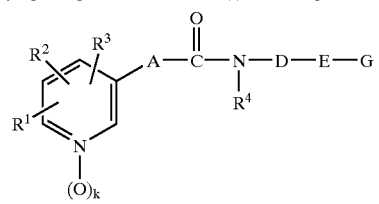

| Nr | R¹–R³ | k | A | R⁴ | D—E—G |
|---|---|---|---|---|---|
| 174 | H | 0 | CH=CH | H | CH₂CH₂CH₂CH₂–piperazine–C(O)–(2-phenyl)phenyl |
| 175 | H | 0 | CH₂CH₂ | H | CH₂CH₂CH₂CH₂–piperazine–C(O)–biphenyl |
| 176 | H | 0 | CH=CH | H | CH₂CH₂CH₂–piperazine–C(O)–C₆H₄–C(O)–C₆H₅ |
| 177 | H | 0 | CH=CH | H | CH₂CH₂CH₂CH₂–piperazine–C(O)–(2'-COOH-biphenyl-2-yl) |
| 178 | H | 0 | CH₂CH₂ | H | CH₂CH₂CH₂CH₂–piperazine–C(O)–biphenyl–COOH |
| 179 | H | 0 | CH=CH | H | (CH₂)₆–piperazine–C(O)–1-naphthyl |
| 180 | H | 0 | CH=CH | H | CH₂CH₂CH₂CH₂–piperazine–C(O)–2-naphthyl |
| 181 | H | 0 | CH=CH | H | CH₂CH₂CH₂CH₂–piperazine–C(O)–(6-COOH-2-naphthyl) |

TABLE 1-continued

Exemplifying compounds of formula (I) according to the invention

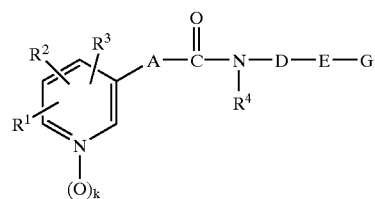

| Nr | R¹–R³ | k | A | R⁴ | D—E—G |
|---|---|---|---|---|---|
| 182 | H | 0 | CH₂CH₂ | H | CH₂CH₂CH₂CH₂–piperazine–C(O)–fluorenone |
| 183 | H | 0 | CH=CH | H | CH₂CH₂CH₂CH₂–piperazine–C(O)–fluorenone |
| 184 | H | 0 | CH₂CH₂ | H | CH₂CH₂CH₂CH₂–piperazine–C(O)–anthraquinone |
| 185 | 5-CF₃ | 0 | CH=CH | H | CH₂CH₂CH₂CH₂–piperazine–C(O)–2-furyl |
| 186 | H | 0 | CH₂CH₂ | H | CH₂CH₂–piperazine–C(O)–2-pyridyl |
| 187 | H | 0 | CH=CH—CH=CH | H | CH₂CH₂CH₂CH₂–piperazine–C(O)–3-pyridyl |
| 188 | H | 0 | CH=CH | H | CH₂CH₂CH₂CH₂–piperazine–C(O)–(5-COOH-3-pyridyl) |
| 189 | H | 0 | CH=CH | H | CH₂CH₂CH₂CH₂–piperazine–C(O)–(6-NH₂-3-pyridyl) |

TABLE 1-continued

Exemplifying compounds of formula (I) according to the invention

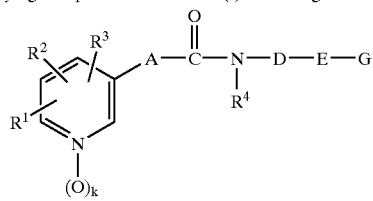

| Nr | R¹–R³ | k | A | R⁴ | D—E—G |
|---|---|---|---|---|---|
| 190 | H | 0 | CH₂CH₂ | H | (6-chloro-2-oxo-benzothiazol-3-ylmethyl-C(O)-piperazinyl-(CH₂)₄–) |
| 191 | H | 0 | CH=CH | H | (6-chloro-2-oxo-thiazolo[5,4-b]pyridin-3-ylmethyl-C(O)-piperazinyl-(CH₂)₄–) |
| 192 | H | 0 | CH=CH | H | (2,3-dihydro-benzo[1,4]dioxin-2-yl-C(O)-piperazinyl-(CH₂)₄–) |
| 193 | H | 0 | CH=CH | H | (quinolin-2-yl-C(O)-piperazinyl-(CH₂)₄–) |
| 194 | H | 0 | CH=CH | H | (cyclopentyl-NH-C(O)-piperazinyl-(CH₂)₄–) |
| 195 | H | 0 | CH=CH | H | (anthracen-9-ylmethyl-NH-C(O)-piperazinyl-(CH₂)₆–) |
| 196 | H | 0 | CH=CH—CH=CH | H | (pyridin-3-ylmethyl-NH-C(O)-piperazinyl-(CH₂)₄–) |

TABLE 1-continued

Exemplifying compounds of formula (I) according to the invention

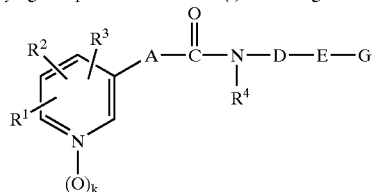

| Nr | R¹–R³ | k | A | R⁴ | D—E—G |
|---|---|---|---|---|---|
| 197 | H | 0 | CH=CH | H | CH₂CH₂CH₂CH₂-piperazine-C(=O)-CH₂-NH-cyclohexyl |
| 198 | H | 0 | CH₂CH₂CH₂CH₂ | H | CH₂CH₂CH₂-piperazine-C(=O)-NH-indanyl |
| 199 | H | 0 | CH₂CH₂ | H | CH₂CH₂CH₂CH₂-piperazine-C(=O)-NH-tetrahydronaphthyl |
| 200 | H | 0 | OCH₂ | H | CH₂CH₂CH₂CH₂-piperazine-C(=O)-NH-tetrahydronaphthyl |
| 201 | H | 0 | CH=CH | H | CH₂CH₂CH₂CH₂CH₂-piperazine-C(=O)-NH-tetrahydronaphthyl |
| 202 | H | 0 | CH₂CH₂ | H | CH₂CH₂CH₂CH₂-piperazine-C(=O)-NH-naphthyl |
| 203 | H | 0 | CH=CH | H | CH₂CH₂-piperazine-C(=O)-NH-acridinyl |
| 204 | H | 0 | CH=CH | H | CH₂CH₂CH₂CH₂-piperazine-C(=O)-NH-(2-C₆H₅-phenyl) |

TABLE 1-continued

Exemplifying compounds of formula (I) according to the invention

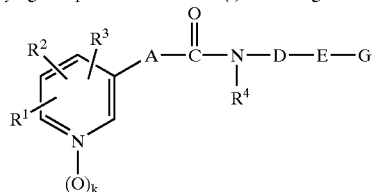

| Nr | R¹–R³ | k | A | R⁴ | D—E—G |
|---|---|---|---|---|---|
| 205 | 6-CH₃ | 0 | CH=CH | H | CH₂CH₂CH₂CH₂—N(piperazine)—C(=O)—N(iPr)₂ |
| 206 | H | 0 | CH₂CH₂ | H | CH₂CH₂CH₂CH₂—N(piperazine)—C(=O)—N(CH₂Ph)₂ |
| 207 | H | 0 | CH₂CH₂CH₂CH₂ | H | CH₂CH₂CH₂CH₂—N(piperazine)—C(=O)—N(Ph)(CH₂Ph) |
| 208 | H | 0 | CH=CH | H | CH₂CH₂—N(piperazine)—C(=O)—N(Ph)₂ |
| 209 | H | 0 | CH=CH | H | CH₂CH₂CH₂CH₂—N(piperazine)—C(=O)—N(Ph)₂ |
| 210 | H | 0 | CH=CH | H | CH₂CH₂CH₂CH₂—N(piperazine)—C(=O)—N(pyrrolidine) |

TABLE 1-continued

Exemplifying compounds of formula (I) according to the invention

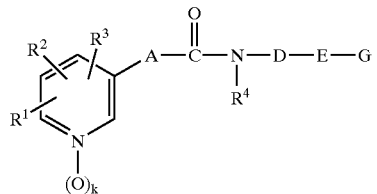

| Nr | R¹–R³ | k | A | R⁴ | D—E—G |
|---|---|---|---|---|---|
| 211 | H | 0 | CH=CH | H | CH₂CH₂CH₂CH₂–piperazine–C(O)–CH₂CH₂–morpholine |
| 212 | H | 0 | CH=CH | H | CH₂CH₂CH₂CH₂–piperazine–C(O)–N(1,2,3,4-tetrahydroquinoline) |
| 213 | H | 0 | CH=CH | H | CH₂CH₂–piperazine–C(O)–N(2,3,4,5-tetrahydro-1H-benzazepine) |
| 214 | H | 0 | CH=CH | H | CH₂CH₂CH₂CH₂–piperazine–C(O)–N(carbazole) |
| 215 | H | 0 | CH₂CH₂ | H | CH₂CH₂–piperazine–C(O)–N(10,11-dihydrodibenzazepine) |
| 216 | H | 0 | CH=CH | H | (CH₂)₆–piperazine–C(O)–N(10,11-dihydrodibenzazepine) |

TABLE 1-continued

Exemplifying compounds of formula (I) according to the invention

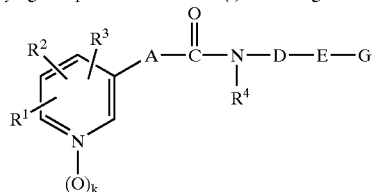

| Nr | R¹–R³ | k | A | R⁴ | D—E—G |
|---|---|---|---|---|---|
| 217 | H | 0 | CH₂CH₂ | H | CH₂CH₂CH₂CH₂—N(piperazine)—C(O)—N(dibenzazepine) |
| 218 | H | 0 | CH=CH | H | CH₂CH₂CH₂CH₂—N(piperazine)—C(O)—N(pyrido-benzazepine) |
| 219 | H | 0 | CH₂CH₂ | H | CH₂CH₂CH₂CH₂—N(piperazine)—C(O)—N(pyrido-benzodiazepinone) |
| 220 | H | 0 | CH=CH | H | (CH₂)₆—N(piperazine)—C(O)—N(pyrido-benzodiazepinone) |
| 221 | H | 0 | CH=CH | H | CH₂CH₂CH₂CH₂—N(piperazine)—N—SO₂—CH₃ |
| 222 | H | 0 | CH=CH—CH=CH | H | CH₂CH₂CH₂CH₂—N(piperazine)—N—SO₂—phenyl |
| 223 | H | 0 | CH₂CH₂ | H | (CH₂)₆—N(piperazine)—N—SO₂—C₆H₄—CH₃ |
| 224 | H | 0 | CH=CH | H | CH₂CH₂—N(piperazine)—N—SO₂—naphthyl |

TABLE 1-continued

Exemplifying compounds of formula (I) according to the invention

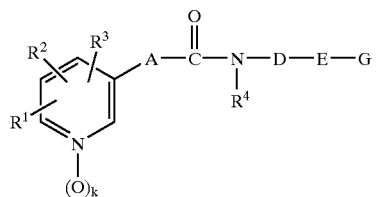

| Nr | R¹–R³ | k | A | R⁴ | D—E—G |
|---|---|---|---|---|---|
| 225 | H | 0 | $CH_2CH_2$ | H | $CH_2CH_2$—N(piperazine)N—$SO_2$—(1-naphthyl) |
| 226 | H | 0 | $CH_2CH_2$ | H | $CH_2CH_2$—N(piperazine)N—$SO_2$—(2-naphthyl) |
| 227 | H | 0 | CH=CH | H | $CH_2CH_2$—N(piperazine)N—$SO_2$—(2-naphthyl) |
| 228 | H | 0 | CH=CH | H | $CH_2CH_2CH_2CH_2$—N(piperazine)N—$SO_2$—(2-naphthyl) |
| 229 | H | 0 | $CH_2CH_2$ | H | $CH_2CH_2CH_2CH_2$—N(piperazine)N—$SO_2$—(3-pyridyl) |
| 230 | 5-F | 0 | CH=CH | H | $CH_2CH_2CH_2CH_2$—N(piperazine)N—$SO_2$—(5-chlorobenzothiophen-2-yl) |
| 231 | H | 0 | CH=CH | H | $CH_2CH_2$—N(piperazine)N—$SO_2$—(quinolin-8-yl) |
| 232 | H | 0 | CH=CH | H | $CH_2CH_2$—N(piperazine)N—P(=O)(phenyl)₂ |

TABLE 1-continued

Exemplifying compounds of formula (I) according to the invention

| Nr | R¹–R³ | k | A | R⁴ | D—E—G |
|---|---|---|---|---|---|
| 233 | H | 0 | OCH$_2$ | H | CH$_2$CH$_2$–piperazine–P(=O)(phenyl)$_2$ |
| 234 | H | 0 | CH=CH | H | CH$_2$CH$_2$CH$_2$CH$_2$–piperazine–P(=O)(phenyl)$_2$ |
| 235 | H | 0 | CH=CH—CH=CH | H | CH$_2$CH$_2$CH$_2$CH$_2$–piperazine–P(=O)(phenyl)$_2$ |
| 236 | 6-CH$_3$ | 0 | CH=CH | H | CH$_2$C≡CCH$_2$–piperazine–P(=O)(phenyl)$_2$ |
| 237 | H | 0 | CH$_2$CH$_2$ | H | CH$_2$CH$_2$CH$_2$CH$_2$CH$_2$–piperazine–P(=O)(phenyl)$_2$ |
| 238 | H | 0 | CH=CH | H | (CH$_2$)$_6$–piperazine–P(=O)(phenyl)$_2$ |

TABLE 1-continued

Exemplifying compounds of formula (I) according to the invention

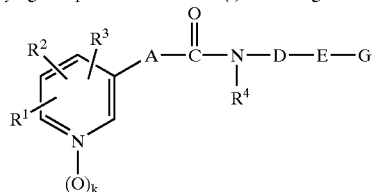

| Nr | R¹–R³ | k | A | R⁴ | D—E—G |
|---|---|---|---|---|---|
| 239 | H | 0 | CH=CH | H | CH₂CH₂CH₂CH₂–N(piperazine)–N–P(=O)(phenyl)(4-chlorophenyl) |
| 240 | H | 0 | CH=CH | H | CH₂CH₂CH₂CH₂–N(piperazine)–N–C(=O)CF₃ |
| 241 | H | 0 | CH=CH—CH=CH | H | CH₂CH₂CH₂CH₂–N(piperazine)–N–C(=O)–O–CH₂CH=CH₂ |
| 242 | H | 0 | CH₂CH₂ | H | CH₂CH₂CH₂CH₂–N(piperazine)–N–C(=O)–O–C(CH₃)₃ |
| 243 | H | 0 | CH=CH | H | CH₂CH₂CH₂CH₂–N(piperazine)–N–C(=O)–O–C(CH₃)₃ |
| 244 | H | 0 | CH=CH | H | (CH₂)₆–N(piperazine)–N–C(=O)–O–C(CH₃)₃ |
| 245 | H | 0 | cyclopropyl | H | CH₂CH₂–N(piperazine)–N–C(=O)–O–C(CH₃)₃ |
| 246 | H | 0 | C≡C | H | CH₂CH₂CH₂CH₂–N(piperazine)–N–C(=O)–O–C(CH₃)₃ |
| 247 | H | 0 | CH=CH | H | CH₂C≡CCH₂–N(piperazine)–N–C(=O)–O–C(CH₃)₃ |

TABLE 1-continued

Exemplifying compounds of formula (I) according to the invention

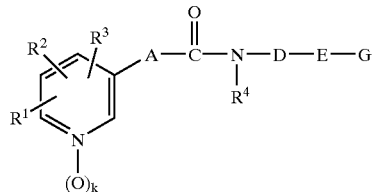

| Nr | R¹–R³ | k | A | R⁴ | D—E—G |
|---|---|---|---|---|---|
| 248 | H | 0 | CH₂CH₂ | H | CH₂CH₂CH₂CH₂—N(piperazine)—C(=O)—O—CH₂—C₆H₅ |
| 249 | H | 0 | CH₂CH₂ | H | CH₂CH₂CH₂CH₂CH₂—N(piperazine)—C(=O)—O—CH₂—C₆H₅ |
| 250 | H | 0 | CH=CH | H | CH₂CH₂—N(homopiperazine)—H |
| 251 | H | 0 | CH=CH | H | CH₂CH₂CH₂CH₂—N(homopiperazine)—H |
| 252 | H | 0 | CH=CH | H | CH₂CH₂CH₂—N(homopiperazine)—cycloheptyl |
| 253 | H | 0 | OCH₂ | H | CH₂CH₂CH₂CH₂—N(homopiperazine)—N—CH₂—C₆H₅ |
| 254 | H | 0 | CH=CH—CH=CH | H | CH₂CH₂—N(homopiperazine)—CH₂CH₂—C₆H₅ |
| 255 | H | 0 | CH₂CH₂ | H | CH₂CH₂CH₂CH₂—N(homopiperazine)—CH(CH₃)—C₆H₅ |
| 256 | H | 0 | CH=CH | H | CH₂CH₂CH₂CH₂—N(homopiperazine)—CH₂—C₆H₄(o-C₆H₅) |

TABLE 1-continued

Exemplifying compounds of formula (I) according to the invention

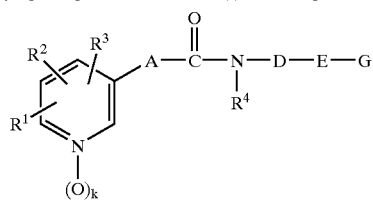

| Nr | R¹–R³ | k | A | R⁴ | D—E—G |
|---|---|---|---|---|---|
| 257 | H | 0 | OCH$_2$ | H | CH$_2$CH$_2$CH$_2$CH$_2$—N(homopiperazine)—CH(C$_6$H$_5$)$_2$ |
| 258 | H | 0 | CH=CH | H | CH$_2$C≡CCH$_2$—N(homopiperazine)—CH(C$_6$H$_5$)$_2$ |
| 259 | H | 0 | CH$_2$CH$_2$ | H | CH$_2$CH$_2$OCH$_2$CH$_2$—N(homopiperazine)—CH(C$_6$H$_5$)$_2$ |
| 260 | H | 0 | CH$_2$CHF | H | CH$_2$CH$_2$CH$_2$CH$_2$—N(homopiperazine)—N—CH$_2$CH(C$_6$H$_5$)$_2$ |
| 261 | H | 0 | C≡C | H | CH$_2$CH$_2$CH$_2$CH$_2$—N(homopiperazine)—CH(2-ClC$_6$H$_4$)$_2$ |
| 262 | H | 0 | CH=CH | H | CH$_2$CH$_2$CH$_2$CH$_2$—N(homopiperazine)—CH(C$_6$H$_5$)(4-COOH-C$_6$H$_4$) |
| 263 | H | 0 | CH$_2$CH$_2$ | H | CH$_2$C≡CCH$_2$—N(homopiperazine)—CH(C$_6$H$_5$)(4-pyridyl) |

TABLE 1-continued

Exemplifying compounds of formula (I) according to the invention

| Nr | R¹–R³ | k | A | R⁴ | D—E—G |
|---|---|---|---|---|---|
| 264 | H | 0 | CH=CH | H | CH₂CH₂—N(homopiperazine)—(2-phenylphenyl) |
| 265 | H | 0 | CH₂CH₂ | H | CH₂CH₂CH₂CH₂—N(homopiperazine)—(2-phenylphenyl) |
| 266 | H | 0 | CH=CH | H | CH₂CH₂CH₂CH₂—N(homopiperazine)—(2-phenylphenyl) |
| 267 | H | 0 | CH₂CH₂ | H | CH₂CH₂CH₂CH₂—N(homopiperazine)—(1-tetrahydronaphthyl) |
| 268 | H | 0 | CH=CH | H | CH₂CH₂CH₂CH₂—N(homopiperazine)—(1-tetrahydronaphthyl) |
| 269 | H | 0 | C(CH₃)=CH | H | CH₂CH₂CH₂CH₂—N(homopiperazine)—(1-tetrahydronaphthyl) |
| 270 | H | 0 | CH₂CH₂ | H | CH₂CH₂CH₂CH₂—N(homopiperazine)—(9-fluorenyl) |

TABLE 1-continued

Exemplifying compounds of formula (I) according to the invention

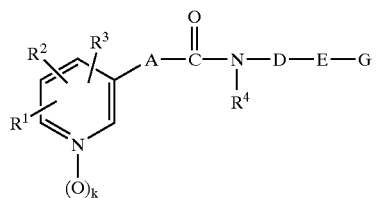

| Nr | R¹–R³ | k | A | R⁴ | D—E—G |
|---|---|---|---|---|---|
| 271 | H | 0 | CH=CH | H | 4-(fluoren-9-yl)-1-homopiperazinyl-CH₂CH₂CH₂CH₂– |
| 272 | H | 0 | CH=CH | H | 4-(10,11-dihydro-5H-dibenzo[a,d]cyclohepten-5-yl)-1-homopiperazinyl-CH₂CH₂– |
| 273 | H | 0 | CH₂CH₂ | H | 4-(10,11-dihydro-5H-dibenzo[a,d]cyclohepten-5-yl)-1-homopiperazinyl-CH₂CH₂CH₂CH₂– |
| 274 | H | 0 | OCH₂ | H | 4-(10,11-dihydro-5H-dibenzo[a,d]cyclohepten-5-yl)-1-homopiperazinyl-CH₂CH₂CH₂CH₂– |
| 275 | H | 0 | CH=CH | H | 4-(10,11-dihydro-5H-dibenzo[a,d]cyclohepten-5-yl)-1-homopiperazinyl-CH₂CH₂CH₂CH₂– |

TABLE 1-continued

Exemplifying compounds of formula (I) according to the invention

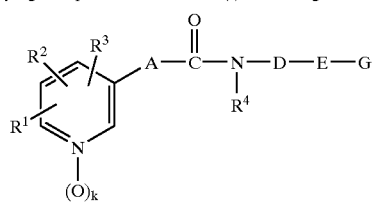

| Nr | R¹–R³ | k | A | R⁴ | D—E—G |
|---|---|---|---|---|---|
| 276 | 6-CF$_3$ | 0 | CH=CH | H | (structure: CH$_2$CH$_2$CH$_2$CH$_2$–N[homopiperazine]–CH[dibenzosuberyl]) |
| 277 | H | 1 | CH=CH | H | (structure: CH$_2$CH$_2$CH$_2$CH$_2$–N[homopiperazine]–CH[dibenzosuberyl]) |
| 278 | H | 0 | CH=CH | CH$_3$ | (structure: CH$_2$CH$_2$CH$_2$CH$_2$–N[homopiperazine]–CH[dibenzosuberyl]) |
| 279 | H | 0 | CH$_2$CH$_2$ | H | (structure: CH$_2$CH=CHCH$_2$–N[homopiperazine]–CH[dibenzosuberyl]) |
| 280 | H | 0 | CH=CH | H | (structure: CH$_2$CH$_2$OCH$_2$CH$_2$–N[homopiperazine]–CH[dibenzosuberyl]) |

TABLE 1-continued
Exemplifying compounds of formula (I) according to the invention
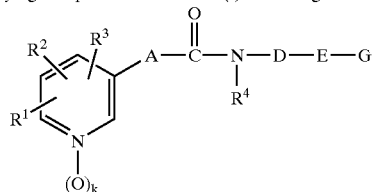
| Nr | R¹–R³ | k | A | R⁴ | D—E—G |
|---|---|---|---|---|---|
| 281 | H | 0 | CH=CH | H | |
| 282 | H | 0 | CH₂CH₂ | H | |
| 283 | H | 0 | CH=CH | H | |
| 284 | H | 0 | CH₂CH₂ | H | |
| 285 | H | 0 | CH=CH | H | |
| 286 | H | 0 | CH₂ | H | |

TABLE 1-continued

Exemplifying compounds of formula (I) according to the invention

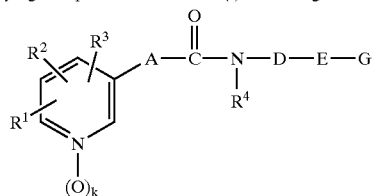

| Nr | R¹–R³ | k | A | R⁴ | D—E—G |
|---|---|---|---|---|---|
| 287 | H | 0 | CH=CH | H | CH₂CH₂—N(piperazine-like 7-ring)—C(=O)—phenyl |
| 288 | H | 0 | CH₂CH₂ | H | CH₂CH₂CH₂—N(7-ring)—C(=O)—phenyl |
| 289 | H | 0 | CH=CH | H | CH₂CH₂CH₂CH₂—N(7-ring)—C(=O)—(2-C₄H₅-phenyl) |
| 290 | H | 0 | CH=CH | H | CH₂CH₂CH₂CH₂—N(7-ring)—C(=O)—naphthyl |
| 291 | H | 0 | CH₂CH₂ | H | CH₂CH₂CH₂CH₂—N(7-ring)—C(=O)—(9-fluorenone) |
| 292 | H | 0 | CH=CH | H | CH₂CH₂—N(7-ring)—C(=O)—(2-furyl) |
| 293 | H | 0 | CH=CH | H | CH₂CH₂CH₂CH₂—N(7-ring)—C(=O)—(2-furyl) |

TABLE 1-continued

Exemplifying compounds of formula (I) according to the invention

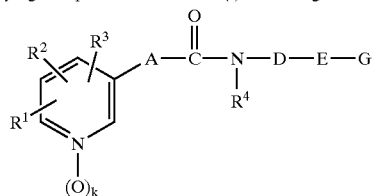

| Nr | R¹–R³ | k | A | R⁴ | D—E—G |
|---|---|---|---|---|---|
| 294 | H | 0 | CH$_2$CH$_2$ | H | CH$_2$CH$_2$CH$_2$CH$_2$–N(homopiperazine)–C(O)–NH–CH$_2$–2-naphthyl |
| 295 | H | 0 | CH=CH | H | CH$_2$CH$_2$CH$_2$CH$_2$–N(homopiperazine)–C(O)–NH–1-naphthyl |
| 296 | H | 0 | CH$_2$CH$_2$ | H | CH$_2$CH$_2$CH$_2$CH$_2$–N(homopiperazine)–C(O)–NH–3-pyridyl |
| 297 | H | 0 | CH=CH | H | CH$_2$CH$_2$CH$_2$CH$_2$–N(homopiperazine)–C(O)–N(10,11-dihydro-5H-dibenzo[b,f]azepine) |
| 298 | H | 0 | CH=CH | H | CH$_2$CH$_2$CH$_2$CH$_2$–N(homopiperazine)–C(O)–N(pyrido-benzazepine) |
| 299 | H | 0 | CH=CH | H | CH$_2$CH$_2$CH$_2$CH$_2$–N(homopiperazine)–C(O)–N(pyrido-benzodiazepinone) |

TABLE 1-continued

Exemplifying compounds of formula (I) according to the invention

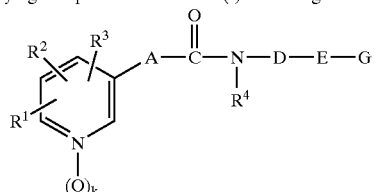

| Nr | R¹–R³ | k | A | R⁴ | D—E—G |
|---|---|---|---|---|---|
| 300 | H | 0 | OCH$_2$ | H | CH$_2$CH$_2$–N(CH$_2$CH$_2$)$_2$N–SO$_2$–C$_6$H$_4$–CH$_3$ |
| 301 | H | 0 | CH=CH | H | CH$_2$CH$_2$–N(CH$_2$CH$_2$)$_2$N–SO$_2$–(2-naphthyl) |
| 302 | H | 0 | CH$_2$CH$_2$ | H | CH$_2$CH$_2$CH$_2$CH$_2$–N(CH$_2$CH$_2$)$_2$N–SO$_2$–(1-naphthyl) |
| 303 | H | 0 | CH=CH | H | CH$_2$CH$_2$CH$_2$CH$_2$–N(CH$_2$CH$_2$)$_2$N–P(=O)(C$_6$H$_5$)$_2$ |
| 304 | H | 0 | CH=CH | H | CH$_2$CH$_2$–N(CH$_2$CH$_2$)$_2$N–C(=O)O–C(CH$_3$)$_3$ |
| 305 | H | 0 | CH=CH | H | CH$_2$CH$_2$CH$_2$CH$_2$–N(CH$_2$CH$_2$)$_2$N–C(=O)O–C(CH$_3$)$_3$ |
| 306 | H | 0 | CH=CH | H | CH$_2$CH$_2$CH$_2$CH$_2$–N(diazocane)N–CH(C$_6$H$_5$)$_2$ |
| 307 | H | 0 | CH$_2$CH$_2$ | H | CH$_2$CH$_2$CH$_2$CH$_2$–N(diazocane)N–(9-fluorenyl) |

TABLE 1-continued

Exemplifying compounds of formula (I) according to the invention

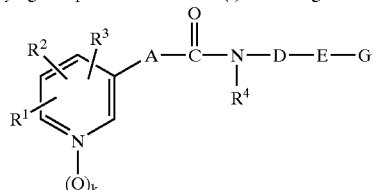

| Nr | R¹–R³ | k | A | R⁴ | D—E—G |
|---|---|---|---|---|---|
| 308 | H | 0 | CH=CH | H | CH₂CH₂CH₂CH₂-[azocane-N-dibenzosuberyl] |
| 309 | H | 0 | CH=CH—CH=CH | H | CH₂CH₂CH₂CH₂-[azocane-N-dibenzosuberyl] |
| 310 | H | 0 | CH=CH | H | CH₂CH₂-[azocane-N-C(O)-CH(phenyl)₂] |
| 311 | H | 0 | CH=CH | H | CH₂CH₂CH₂CH₂-[azocane-N-C(O)-phenyl] |
| 312 | H | 0 | CH=CH | H | CH₂CH₂CH₂CH₂-[azocane-N-C(O)-(9-fluorenone-1-yl)] |
| 313 | H | 0 | OCH₂ | H | CH₂CH₂CH₂CH₂-[azocane-N-C(O)-NH-(2-naphthyl)] |

TABLE 1-continued
Exemplifying compounds of formula (I) according to the invention
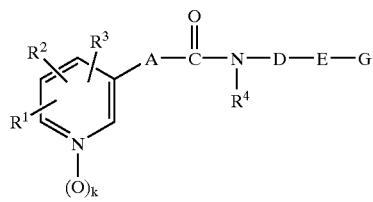
| Nr | R¹–R³ | k | A | R⁴ | D—E—G |
|---|---|---|---|---|---|
| 314 | H | 0 | CH=CH | H | 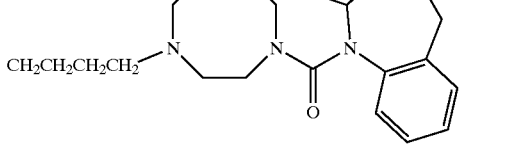 |
| 315 | H | 0 | CH=CH | H | 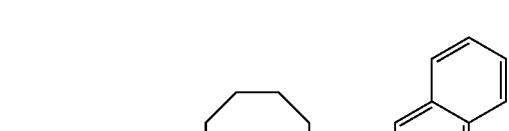 |
| 316 | H | 0 | CH=CH | H | 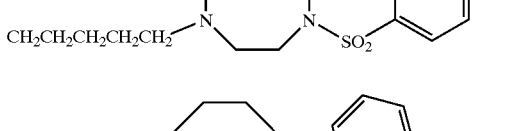 |
| 317 | H | 0 | CH=CH | H | 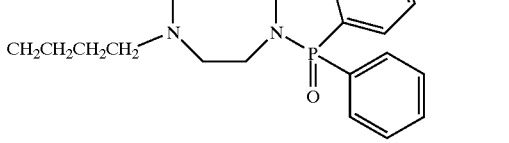 |
| 318 | H | 0 | $CH_2CH_2$ | H |  |
| 319 | H | 0 | CH=CH—CH=CH | H | 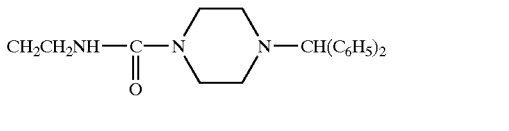 |
| 320 | H | 0 | CH=CH | $CH_3$ | 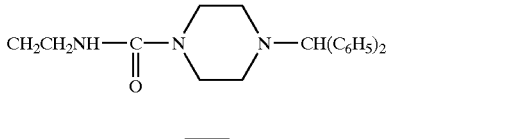 |
| 321 | H | 0 | CH=CH | H | 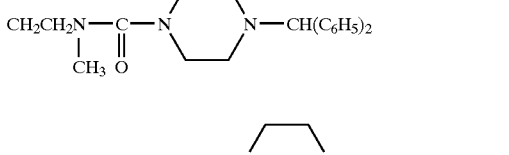 |

TABLE 1-continued

Exemplifying compounds of formula (I) according to the invention

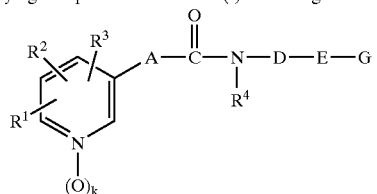

| Nr | R¹–R³ | k | A | R⁴ | D—E—G |
|---|---|---|---|---|---|
| 322 | H | 0 | CH=CH | H | CH₂CH₂—N(piperazine)—CH(phenyl)(2-hydroxyphenyl) |
| 323 | H | 0 | CH₂CH₂ | H | CH₂CH₂CH₂—N(piperazine)—CH(phenyl)(2-hydroxyphenyl) |
| 324 | H | 0 | CH=CH | H | CH₂CH₂CH₂—N(piperazine)—CH(phenyl)(2-hydroxyphenyl) |
| 325 | H | 0 | CH=CH | H | CH₂CH₂—N(piperazine)—CH(phenyl)(2-carboxyphenyl) |
| 326 | H | 0 | CH=CH | H | CH₂CH₂CH₂CH₂—N(piperazine)—CH(phenyl)(2-carboxyphenyl) |
| 327 | H | 0 | CH₂CH₂ | H | CH₂CH₂CH₂CH₂CH₂—N(piperazine)—CH(phenyl)(2-carboxyphenyl) |

TABLE 1-continued

Exemplifying compounds of formula (I) according to the invention

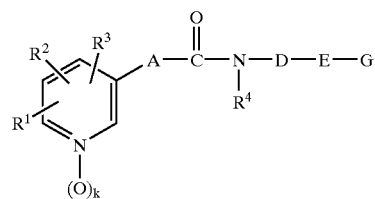

| Nr | R¹–R³ | k | A | R⁴ | D—E—G |
|---|---|---|---|---|---|
| 328 | H | 0 | CH=CH | H | CH₂CH₂CH₂CH₂—piperazine—CH(phenyl)(2-H₂NOC-phenyl) |
| 329 | H | 0 | CH=CH | H | CH₂CH₂CH₂CH₂—piperazine—CH(phenyl)(4-H₂NOC-phenyl) |
| 330 | H | 0 | CH₂CH₂ | H | CH₂CH₂CH₂CH₂—piperazine—CH(phenyl)(4-(CH₂CH₂COOH)-phenyl) |
| 331 | H | 0 | CH=CH | H | CH₂CH₂—piperazine—CH(phenyl)(2-H₂N-phenyl) |
| 332 | H | 0 | CH₂CH₂ | H | CH₂CH₂CH₂CH₂—piperazine—CH(phenyl)(2-H₂N-phenyl) |

TABLE 1-continued

Exemplifying compounds of formula (I) according to the invention

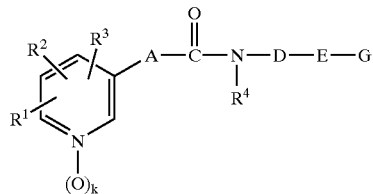

| Nr | R¹–R³ | k | A | R⁴ | D—E—G |
|---|---|---|---|---|---|
| 333 | H | 0 | CH=CH | H | CH₂CH₂CH₂CH₂—piperazine—CH(phenyl)(2-aminophenyl) |
| 334 | H | 0 | CH=CH—CH=CH | H | CH₂CH₂CH₂CH₂—piperazine—CH(phenyl)(2-aminophenyl) |
| 335 | H | 0 | CH=CH | H | (CH₂)₅—piperazine—CH(phenyl)(2-aminophenyl) |
| 336 | H | 0 | CH₂CH₂ | H | CH₂CH₂CH₂CH₂—piperazine—CH(phenyl)(4-aminophenyl) |
| 337 | H | 0 | CH=CH | H | CH₂CH₂CH₂CH₂—piperazine—CH(phenyl)(4-aminophenyl) |

TABLE 1-continued

Exemplifying compounds of formula (I) according to the invention

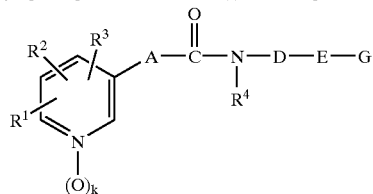

| Nr | R¹–R³ | k | A | R⁴ | D—E—G |
|---|---|---|---|---|---|
| 338 | H | 0 | SCH$_2$ | H | CH$_2$CH$_2$CH$_2$CH$_2$—N(piperazine)N—CH(C$_6$H$_5$)(2-pyridyl) |
| 339 | H | 0 | SCH$_2$ | H | CH$_2$CH$_2$CH$_2$CH$_2$—N(piperazine)N—(2-C$_6$H$_5$-phenyl) |
| 340 | H | 0 | CH=CH | H | CH$_2$CH$_2$NH—C(=O)—N(piperazine)N—(2-C$_6$H$_5$-phenyl) |
| 341 | H | 0 | CH$_2$CH$_2$ | CH$_3$ | CH$_2$CH$_2$N(CH$_3$)—C(=O)—N(piperazine)N—(2-C$_6$H$_5$-phenyl) |
| 342 | H | 0 | CH=CH | H | CH$_2$CH$_2$CH$_2$CH$_2$NH—C(=O)—N(piperazine)N—(2-C$_4$H$_5$-phenyl) |
| 343 | H | 0 | SCH$_2$ | H | CH$_2$CH$_2$CH$_2$CH$_2$—N(piperazine)N—(9H-fluoren-9-yl) |
| 344 | H | 0 | CH=CH | CH$_3$ | CH$_2$CH$_2$N(CH$_3$)—C(=O)—N(piperazine)N—(9H-fluoren-9-yl) |

TABLE 1-continued

Exemplifying compounds of formula (I) according to the invention

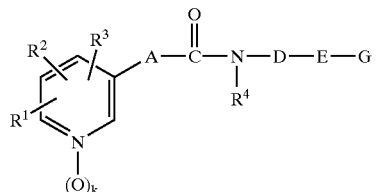

| Nr | R¹–R³ | k | A | R⁴ | D—E—G |
|---|---|---|---|---|---|
| 345 | H | 0 | SCH$_2$ | H | (CH$_2$)$_6$–piperazine–dibenzosuberyl |
| 346 | H | 0 | CH=CH | H | CH$_2$CH$_2$CH$_2$NH–C(=O)–piperazine–dibenzosuberyl |
| 347 | H | 0 | CH=CH | H | CH$_2$CH$_2$CH$_2$CH$_2$–piperazine–C(=O)–(2-hydroxyphenyl) |
| 348 | H | 0 | CH$_2$CH$_2$ | H | CH$_2$CH$_2$CH$_2$CH$_2$–piperazine–C(=O)–(2-aminophenyl) |
| 349 | H | 0 | CH=CH | H | CH$_2$CH$_2$CH$_2$CH$_2$–piperazine–C(=O)–(2-aminophenyl) |
| 350 | H | 0 | CH$_2$CH$_2$ | H | CH$_2$CH$_2$CH$_2$CH$_2$–piperazine–C(=O)–(2-carboxyphenyl) |
| 351 | H | 0 | CH=CH | H | CH$_2$CH$_2$CH$_2$CH$_2$–piperazine–C(=O)–(2-carboxyphenyl) |

TABLE 1-continued

Exemplifying compounds of formula (I) according to the invention

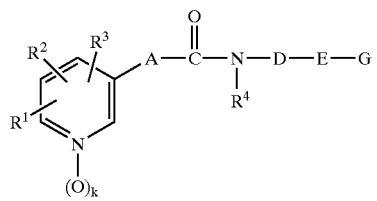

| Nr | R¹–R³ | k | A | R⁴ | D—E—G |
|---|---|---|---|---|---|
| 352 | H | 0 | CH=CH | H | CH₂CH₂CH₂CH₂—N(piperazine)—C(=O)—C₆H₄(o-C(=O)NH₂) |
| 353 | H | 0 | CH=CH | H | CH₂CH₂CH₂CH₂—N(piperazine)—C(=O)—C₆H₄(o-SCH₃) |
| 354 | H | 0 | CH=CH | H | CH₂CH₂CH₂CH₂—N(piperazine)—C(=O)—C₆H₄(p-CH₂CH₂COOH) |
| 355 | H | 0 | CH=CH | H | CH₂CH₂CH₂CH₂—N(piperazine)—C(=O)—C₆H₃(OH)(NH₂) |
| 356 | H | 0 | CH=CH | H | CH₂CH₂—N(piperazine)—C(=O)—(azabenzocycloheptene) |
| 357 | H | 0 | CH₂CH₂ | H | CH₂CH₂CH₂CH₂—N(piperazine)—C(=O)—(azabenzocycloheptene) |
| 358 | H | 0 | CH=CH | H | CH₂CH₂CH₂CH₂—N(piperazine)—C(=O)—(azabenzocycloheptene) |

TABLE 1-continued

Exemplifying compounds of formula (I) according to the invention

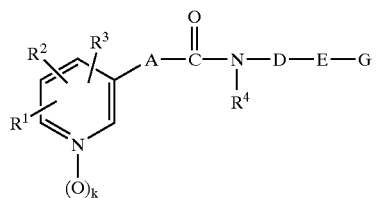

| Nr | R¹–R³ | k | A | R⁴ | D—E—G |
|---|---|---|---|---|---|
| 359 | H | 0 | CH=CH | H | (CH₂)₆–piperazine–C(=O)–6,11-dihydro-5H-benzo[5,6]cyclohepta[1,2-b]pyridin-11-yl |
| 360 | H | 0 | CH=CH | H | CH₂CH₂CH₂CH₂–piperazine–C(=O)–indolin-1-yl |
| 361 | H | 0 | CH=CH—CH=CH | H | CH₂CH₂CH₂CH₂–piperazine–C(=O)–indolin-1-yl |
| 362 | H | 0 | CH₂CH₂ | H | CH₂CH₂CH₂CH₂–piperazine–C(=O)–isoindolin-2-yl |
| 363 | H | 0 | CH=CH | H | CH₂CH₂CH₂CH₂–piperazine–C(=O)–isoindolin-2-yl |
| 364 | H | 0 | CH=CH | H | CH₂CH₂–piperazine–C(=O)–9,10-dihydroacridin-10-yl |

TABLE 1-continued

Exemplifying compounds of formula (I) according to the invention

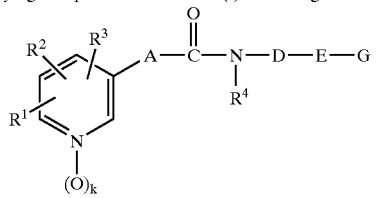

| Nr | R¹–R³ | k | A | R⁴ | D—E—G |
|---|---|---|---|---|---|
| 365 | H | 0 | CH₂CH₂CH₂CH₂ | H | CH₂CH₂CH₂CH₂—N-piperazine-C(O)—N(dibenzazepine) |
| 366 | H | 0 | CH=CH | H | CH₂CH₂CH₂CH₂—N-piperazine-C(O)—N(dihydrophenanthridine) |
| 367 | H | 0 | CH=CH | H | CH₂CH₂OCH₂CH₂—N-piperazine-C(O)—N(dihydrophenanthridine) |
| 368 | H | 0 | CH=CH | H | CH₂CH₂CH₂CH₂—N-piperazine-C(O)—N(benzisoquinoline) |
| 369 | H | 0 | OCH₂ | H | CH₂CH₂CH₂CH₂—N-piperazine-C(O)—N(benzisoquinoline) |
| 370 | H | 0 | CH=CH | H | CH₂CH₂CH₂CH₂—N-piperazine-C(O)—N(dibenzazepine) |

TABLE 1-continued
Exemplifying compounds of formula (I) according to the invention
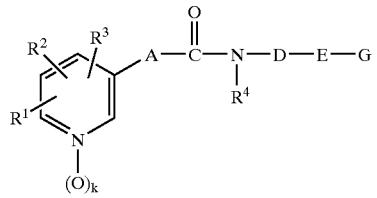
| Nr | R¹–R³ | k | A | R⁴ | D—E—G |
|---|---|---|---|---|---|
| 371 | H | 0 | SCH$_2$ | H | |
| 372 | H | 0 | CH=CH | H | |
| 373 | H | 0 | CH=CH | H | |
| 374 | H | 0 | CH=CH | H | |
| 375 | H | 0 | SCH$_2$ | H | |
| 376 | H | 0 | CH=CH | CH$_3$ | |
| 377 | H | 0 | CH=CH | H | |

TABLE 1-continued

Exemplifying compounds of formula (I) according to the invention

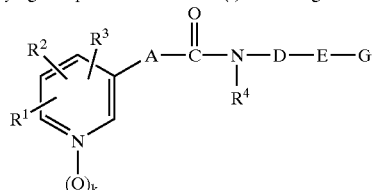

| Nr | R¹–R³ | k | A | R⁴ | D—E—G |
|---|---|---|---|---|---|
| 378 | H | 0 | CH=CH | H | CH₂CH₂CH₂CH₂—N(piperazine)—C(=O)—(2-COOH-phenyl) |
| 379 | H | 0 | CH=CH | H | CH₂CH₂CH₂CH₂—N(piperazine)—C(=O)—(azatricyclic) |
| 380 | H | 0 | CH=CH | H | CH₂CH₂CH₂CH₂—N(piperazine)—C(=O)—N(dibenzazepine) |

Further subject-matter of the claims are known analogous methods for the production of the compounds of formula (I) according to the invention.

According to method variant (A), compounds of formula (I) are (a) obtained in the manner by reacting carboxylic acids of formula (II)

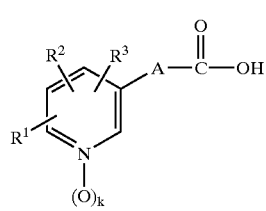

(II)

in which $R^1$, $R^2$, $R^3$, A and k have the meaning given above or their reactive derivatives with compounds of formula (III)

$$H-N(R^4)-D-E-G \quad (III)$$

wherein D, E, G and $R^4$ also have the above described meanings and the meanings given in the claims.

Reactive derivatives of compound (II) can be, for example, activated esters, anhydrides, acid halides (especially acid chlorides) or simple low alkyl esters. Suitable activated esters are, for example, p-nitrophenyl ester, 2,4,6-trichlorphenyl ester, pentachlorophenyl ester, cyanomethyl ester, esters of N-hydroxysuccinimide, N-hydroxyphthalimides, 1-hydroxybenzotriazole, N-hydroxypiperidine, 2-hydroxypyridine, 2-mercaptopyridine, etc. Anhydrides can be symmetric anhydrides or mixed, as they are obtained, for example, with pivaloyl chloride or with chloroformates. Aromatic (for example chloroformic phenyl ester), araliphatic (for example chloroformic benzyl ester) or aliphatic chloroformates (for example chloroformic methyl ester, -ethyl ester or -isobutyl ester) can be used for this.

Reaction of compounds (II) with compounds (III) can also be carried out in the presence of condensation agents such as dicyclohexylcarbodiimide, 1-ethyl-3-(3-dimethylaminopropyl)-carbodiimide hydrochloride, N,N'-carbonyldiimidazole, 1-ethoxycarbonyl-2-ethoxy-1,2-dihydroquinoline, etc. If carbodiimides are used as the condensation agent, reagents such as N-hydroxysuccinimide, N-hydroxyphthalimide, 1-hydroxybenzotriazole, N-hydroxypiperidine, etc. can be advantageously added.

Compounds of formula (III) can be used for reaction as free bases as well as in the form of their acid addition salts. For this, the salts of inorganic acids are to be preferred, i.e. hydrochlorides, hydrochlorides or sulfates for example.

Reaction of compounds (II) or their reactive derivatives with compounds (III) are normally carried out in a suitable, preferably inert solvent. As examples, aromatic hydrocarbons such as benzene, toluene, xylene, halogenated hydrocarbons (for example dichloromethane, chloroform, 1,2-dichloroethane, trichloroethylene), ethers (for example diethyl ether, tetrahydrofuran, dioxane, glycol dimethyl ether), ethyl acetate, acetonicrile or polar aprotic solvents such as, for example, dimethylsulfoxide, dimethylformamide or N-methyl-pyrrolidone are to be named. Pure solvents, as well as mixtures of two or more of them, can be used.

The reaction is optionally carried out in the presence of an auxiliary base. Suitable examples for this are alkali metal carbonates (sodium carbonate, potassium carbonate), alkali metal hydrogen carbonates (sodium hydrogen carbonate, potassium hydrogen carbonate), or organic bases such as, for example, triethylamine, ethyl diisopropylamine, tributylamine, N-methylmorpholine or pyridine. A suitable excess of compound (III) can also be used as a base. If compounds (III) are used in form of their acid addition salts, then it is appropriate to consider the amount of auxiliary base used as equivalent.

The reaction temperatures can—depending on reactivity of the starting materials—vary in a wide range. Generally, the reaction is carried out at temperatures between –40° C. and 180° C., preferably between –10° C. and 130° C., especially at the boiling point of the solvent used.

The starting compounds and/or intermediates (II) and (III) are known and/or can be produced according to known methods in an analogous manner. Moreover, their production is further described below by means of representative examples.

Compounds or formula (I) can also be produced according to the variant pursuant to Method B by reaction of compounds of formula (I) wherein G is hydrogen, whereby the latter which themselves are anti-proliferative active ingredients according to the invention (as follows from the definitions for the general formula). Thereby, the reaction of compounds according to formula (I) occurs with a compound of formula (IV),

L—G (IV)

in which G has the meaning given above, with the exception of hydrogen, and L represents a suitable nucleofuge or reactive group. The type of nucleofuge or reactive group L and the conditions of the reaction are dependent of the nature of group G. According to a further variant pursuant to method (B1) compounds of formula (I), in which G, with the exception of hydrogen, has the meaning of $G^1$ according to the above definition can also be synthesized by reacting compounds of formula (I), in which G is hydrogen, with a suitable alkylation agent and/or arylation agent of formula (IV), wherein G is an alkyl-, alkenyl-, alkinyl-, cycloalkyl-, aryl-, aralkyl-, heteroaryl- or heteroaralkyl residue according to definition and the leaving group L can be a reactive derivative of an alcohol, for example, a halogen atom such as chlorine, bromine or iodine or a sulfonic acid ester, i.e. for example a methanesulfonyloxy group, trifluorcmethanesulfonyloxy-, ethanesulfonyloxy-, benzene-sulfonyloxy-, p-toluenesulfonyloxy-, p-bromobenzene-sulfonyloxy-, m-nitrobenzenesulfonyloxy group, etc. A reactive group L can be a terminal epoxide group.

The reaction of compounds (I), in which G is a hydrogen, and (IV) is usually conducted in a suitably inert solvent. Such solvents can be for example, aromatic hydrocarbons (benzene, toluene, xylene), ethers (for example tetrahydrofuran, dioxane, glycol dimethyl ether), ethyl acetate, acetonitrile, ketones (acetone, ethyl methyl ketone), polar protic solvents such as alcohols (ethanol, isopropanol, butanol, glycol monomethyl ether) or polar aprotic solvents such as, for example, dimethylsulfoxide, dimethylformamide or N-methylpyrrolidone. Pure solvents as well as mixtures of two or more can also be used. Preferably, the reactions are carried out in the presence of bases, whereby the same bases as named in method (a) above can be used. If chlorides or bromides are used as compound (IV), the reaction can be accelerated by the addition of alkali metal iodides, for example sodium iodide, potassium iodide. The reaction temperatures can vary between 0° C. and 180° C. depending on the reactivity of the educts, but preferably lie between 20° C. and 130° C. Finally, according co the variant pursuant to method (B2) compounds of formula (I), in which G represents an acyl residue, a carbamoyl residue, a sulfonyl residue or a phosphinoyl residue according to the above definition, can also be produced in a manner by reacting compounds of formula (I), wherein G is hydrogen, with a carboxylic acid, carbamic acid, sulfonic acid and/or phosphinic acid of formula (V),

HO—G (V)

wherein G is an acyl residue, carbamoyl residue, sulfonyl residue or phosphinoyl residue according to definition, or their derivatives capable of reaction. Preferred derivatives of carboxylic acids and/or sulfonic acids (V) which are capable of reaction are symmetric or unsymmetric carboxylic acid anhydrides and/or sulfonic acid anhydrides or acyl- and/or sulfonyl halides, especially acyl- and/or sulfonyl chlorides. Preferred derivatives of carbamates and/or phosphinic acids which are capable of reaction are the carbamoyl halides and/or phosphinyl halides, especially carbamyl- and/or phosphinyl chlorides. The reaction of the acids (V) and/or their reactive derivatives with compounds (I), in which G is hydrogen, preferably occurs in the presence of auxiliary bases in solvents and under conditions as they are described in method (A).

Compounds of formula (I), wherein G represents a carbamoyl residue according to the definition (G2b) with r=0, i.e. is a group

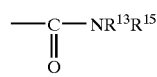

can also be produced pursuant to the variant according co method (B3) by reacting compounds of formula (I), in which G is hydrogen, with a carbonyl group transmitter to an intermediate product and subsequently reacting this directly with a primary or secondary amine with the formula (VI)

H—NR$^{13}$R$^{15}$ (VI)

wherein $R^{13}$ and $R^{15}$ and/or the grouping —NR$^{13}$R$^{15}$ have the above meanings without purifying or isolating the intermediate product.

Bis-trichloromethyl carbonate (triphosgene) and carbonyldiimidazole have been proven as particularly reactive carbonyl group transmitters. The reaction of compounds of formula (I), wherein C is hydrogen, with triphosgene and/or carbonyldiimidazole are typically conducted in an absolute, inert solvent in the presence of a tertiary organic amine as an auxiliary base in such a manner that the solution of compounds (I) and the auxiliary base are slowly poured into a solution of an equivalent amount of carbonyl group transmitter. Thereby, the reaction requires molar ratios of 1:1 for the reaction of compound (I) and carbonyldiimidazol, and, in contrast, a ratio of 1:0.35 for the use of triphosgene. After complete reaction of the components to the intermediate product, compound (VI) is added in stochiometric amounts or in excess as a solution or a solid, whereby the reaction is typically completed at elevated temperature. Suitable inert solvents are, for example hydrocarbons such as hexane, heptane, benzene, toluene, xylene, chlorinated hydrocarbons (for example dichloromethane, chloroform, 1,2-dichloroethane, trichloroethylene), ethers (for example diethyl ether, tetrahydrofuran, dioxane), esters such as ethyl acetate, butyl acetate, acetonitrile or polar aprodic solvents such as formamide or dimethylformamide. Pure solvents as well as mixtures of various solvents can be used. Sometimes it is of advantage to carry out the first partial reaction at low temperature in a low-viscosity, highly-volatile solvent and to remove the solvent after formation of the intermediate and replace it by a higher boiling solvent. Amines such as for example triethylamine, ethyl diisopropylamine, tributylamine, N-methylmorpholine or pyridine are suitable as auxiliary bases.

If compounds (I) or (VI) are used as salts, the amount of the auxiliary base is increased accordingly. The reaction temperatures can lie between −40° C. and 50° C. for the first partial reaction, preferably 0° C. to 30° C., and between 0° C. and 150° C. for the second partial reaction, preferably 20° C. to 120° C. Finally, according to variant pursuant to method (B4) compounds of formula (I), wherein G represents a carbamoyl residue according to the definition (G2b) with r=0 and $R^{15}$ hydrogen, i.e. the group represents

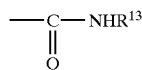

can also be produced by reacting the compounds of formula (I) in which G is hydrogen, with an isocyanate of formula (VII) in which $R^{13}$, has the meaning according to definition

 (VII).

Reaction of the compounds of formula (I), in which G is hydrogen, with the isocyanates of formula (VII) are conducted thereby in an absolute, inert solvent which can be a hydrocarbon such as pentane, hexane, heptane, benzene, toluene, or xylene, chlorinated hydrocarbons (such as dichloromethane, chloroform, 1,2-dichloroechane, trichloroethylene), an ether (for example, diethyl ether, tetrahydrofuran, dioxane), esters such as ethyl acetate, butyl acetate, or polar aprotic solvents such as formamide or dimethylformamide. Mixtures of various solvents can also be used. Thereby, the reaction temperatures can vary in the region from −20° C. to 150° C., but preferably lie at 20° C. to 100° C.

As already mentioned, the compounds of formula (I), wherein G is hydrogen, are themselves active ingredients according to the invention with tumor growth inhibiting activity. However, independent of their therapeutic applicability, they also represent useful intermediate compounds for the production of a multitude of other compounds according to the invention corresponding to the method variants (B1) to (B4).

In principle, the compounds of the formula (I), in which G represents hydrogen, can be produced according to method A by reacting a carboxylic acid of formula (II) with amines of formula (III) in which G is hydrogen as described above. However, since the compounds of formula (III) with hydrogen as G represent α, ω-diamines, the formation of product mixtures is always to be expected in their reaction with carboxylic acids (II) or their reactive derivatives making a subsequent separation necessary.

In contrast, compounds of formula (I), in which C is hydrogen, are essentially more advantageously produced from other compounds of formula (I), in which G is a selectively cleavable group under mild conditions. i.e. corresponds to a nitrogen protective group.

In this connection, among the compounds according to formula (I) with tumor growth inhibiting properties, compounds in which G represents a benzyl group, a 4-methoxybenzyl group, a diphenylmethyl group, a triphenylmethyl group, a benzyloxycarbonyl group, a methoxy- and/or ethoxycarbonyl group, a tert-butoxycarbonyl group, an allyloxycarbonyl group or a trifluoroacetyl group are particularly suitable. Thus, compounds of formula (I) with benzyl, diphenylmethyl, triphenylmethyl or benzyloxycarbonyl groups as G can already be catalytically transformed into compounds of formula (I) with hydrogen as G at room temperature under mild conditions with elementary hydrogen or by transfer hydration. Compounds of formula (I) with a 4-methoxybenzyl group are converted to compounds of formula (I) with hydrogen as G by selective oxidation with ammonium-cer(IV)-nitrate. The cleavage of simple alkoxycarbonyl groups such as the methoxy- or ethoxycarbonyl group as well as the trifluoroacetyl group as G in compounds of formula (I) succeed by alkali hydrolysis under mild conditions without cleaving the A and D linked amide function. This is suitably valid for the cleavage of the triphenylmethyl group and the tert-butoxycarbonyl group in the form of G in compounds of formula (I) which occurs in acidic medium under mild conditions. Finally, compounds of formula (I) with an allyloxycarbonyl group as the meaning for G can be converted into such with hydrogen as the meaning for G in neutral medium with palladium catalyst. All these methods are fully familiar to the person skilled in the art, and are furthermore also documented in various monographs, see for example Greene, Wuts: Protective Groups in Organic Synthesis, New York, 1991.

The compounds of formula (I) produced according to the methods (A) to (B) can be isolated and purified in a known manner, for example by subjecting the residue after distillation of the solvent to partition, extraction, re-precipitation or re-crystallization or another purification method. For this, column chromatography on a suitable support or preparative middle or high pressure liquid chromatography (HPLC) are preferred for this.

The compounds (I) are first normally obtained in form of their free bases or their hydrates or solvates, depending on the type of isolation and purification. Their addition salts with pharmaceutically suitable acids are obtained in a typical manner by converting the base with the desired acid in a suitable solvent. Depending on the number of basic centers of compounds (I), one or more equivalent acids per mole of base can be bound.

Suitable solvents are, for example, chlorinated hydrocarbons such as dichloromethane or chloroform; ethers such as diethyl ether, dioxane or tetrahydrofuran; acetonitrile; ketones such as acetone or ethyl methyl ketone; esters such as methyl acetate or ethyl acetate or low molecular alcohols such as methanol, ethanol or isopropanol; and water. Pure solvents as well as mixtures of two or three solvents can also be used. The salts can be isolated by crystallization, precipitation or the evaporation of the solvent. Thereby, they optionally accumulate as hydrates or solvates.

The bases can be recovered from the salts by alkalization, for example with aqueous ammonia solution, alkali carbonate or diluted sodium hydroxide solution.

The following synthetic examples for end products as well as for starting products and/or intermediate products are meant for illustrating the method variants given above and claimed compounds:

SYNTHETIC EXAMPLES FOR THE END PRODUCTS OF THE INVENTION ACCORDING TO FORMULA (I)

In the production examples for the end products, the abbreviations stand for the following terms:
MP=melting point,
RT=room temperature,
MPLC=intermediate pressure liquid chromatography
THF=tetrahydrofuran,
DMF=dimethylformamide,
abs=absolute,
CDI=carbonyldiimidazole,
EDC=N-(3-dimethylaminopropyl)-N'-ethyl-carbodiimide hydrochloride,
HOBT=1-hydroxybenzotriazole,
TEA=triethylamine.
$^1$H-NMR-Spectrum=proton resonance spectrum, taken at 100 MHz. The chemical shifts are given in ppm against TMS as a standard ($\delta$=0.0), whereby
s=singlet,
d=doublet,
t=triplet,
dt=doublet-triplet,
m=multiplet,
ar=aromatic,
py=pyridine.

Example 1

N-[3-(4-diphenylmethylpiperazin-1-yl)-propoxy]-3-pyridin-3-yl-acrylamide (Substance 30)

3.8 g (22,9 mmol) of 3-(3-pyridyl)-acrylic acid are suspended in 40 ml absolute dichloromethane and after addition of two drops pyridine, are cooled to ca. 0° C. in an ice bath under moisture exclusion. 5 ml (58,5 mmol) of oxalyl chloride are slowly added and the mixture is first stirred for 30 min under ice cooling and then stirred overnight at RT. Subsequently, the solvent and excess oxalyl chloride are distilled off on a rotary evaporator. In order to completely remove the oxalyl chloride, the colorless residue is dried further for two hours under high-vacuum. The acid chloride obtained in this manner is suspended without further purification in 30 ml absolute dichloromethane and cooled to ca. 0° C. in an ice bath under moisture exclusion. 7.45 g (22.9 mmol) 3-(4-diphenylmethyl-piperazinyl)-propyl-hydroxylamine are dissolved in 40 ml absolute dichloromethane and are added dropwise to this suspension. After complete addition, the ice bath is removed and the reaction is stirred for a further two hours at RT. The mixture is subsequently concentrated, taken up in 10% sodium hydroxide solution and extracted three times with acetic acid ethyl ester. The combined organic phases are washed with saturated NaCl solution, dried over sodium sulfate and the solvent is removed under vacuum. The residue is chromatographically purified over silica gel with $CHCl_3/CH_3OH$ (99/1 to 85/15) and crystallized twice from acetic ethyl acid ester after evaporation of the solvent: Colorless crystals with a MP. of 115–117° C.; yield 3.66 g (35%).

$C_{28}H_{32}N_4O_2$ (456.6)

IR-Spectrum (KBr): n(NH) 3200 $cm^{-1}$ n(C=O) 1660 $cm^{-1}$ n(C=C) 1630 $cm^{-1}$ $^1$H-NMR-Spectrum (DMSO-D6): 1.50–1.90 (2H, m, C—C$H_2$—C) 2.05–2.65 (10H, m, piperazine, N—C$H_2$) 3.86 (2H, t, OC$H_2$, J=6.1 Hz) 4.24 (1H, s, $Ar_2$CH) 6.54 (1H, d, CH=C$\underline{H}$CO, J=16.0 Hz) 7.05–7.70 (13H, m, Ar, Py, NH, C$\underline{H}$=CHCO) 7.90–8.15 (1H, m, Py) 8.50–8.70 (1H, m, Py) 8.70–8.90 (1H, m, Py)

Example 2

N-[4-(4-diphenylphosphinoyl-piperazin-1-yl)-butyl]-3-pyridin-3-yl-acrylamide (Substance 234)

2.7 g (18 mmol) 3-(3-pyridyl)-acrylic acid and 3.1 g (19 mmol) CDI are heated under reflux in 100 ml absolute THF under moisture exclusion. After an hour, this is cooled to RT and 7.0 g (19 mmol) 4-(4-diphenyl-phosphinoyl-piperazin-1-yl)-bu-tylamine, dissolved in 30 ml absolute THF, is added dropwise. Following addition, this is further stirred for three hours at RT and left standing overnight. The mixture is poured into 150 ml water and extracted three times with acetic acid ethyl ester by shaking. The combined organic phases are washed with saturated NaCl solution, dried over sodium sulphate and the solution is removed under vacuum. The residue is chromatographically pre-purified over silica gel with $CHCl_3/CH_3OH$ (85/15). After removal of the solvent, the colorless oily residue is further purified by preparative middle pressure chromatography with $CH_2Cl_2/CH_3OH$ (93/7) yield 3.5 g (40%) as amorphous solid material.

$C_{28}H_{33}N_4O_2P$ (488.5)

$^1$H-NMR-Spectrum (CDCl$_3$): 1.40–1.80 (4H, m, C—C$H_2$—C$H_2$—C) 2.20–2.60 (6H, m, piperazine, N—C$H_2$) 2.90–3.25 (4H, m, piperazine) 3.25–3.55 (2H, m, CONHC$\underline{H}_2$) 6.53 (1H, d, CH=C$\underline{H}$CO, J=15.7 Hz) 6.70–6.95 (1H, m, NH) 7.00–8.00 (13H, m, Ar, Py, C$\underline{H}$=CHCO) 8.54 (1H, dd, Py, J=1.4 Hz, J=40.5 Hz) 8.70 (1H, d, Py, J=1.8 Hz)

Example 3

N-[4-(4-diphenylmethyl-piperazin-1-yl)-3-hydroxy-butyl]-3-pyridin-3-yl-acrylamide (Substance 29)

Production Analogues to Example 2.

Batch size: 2.0 g (13.3 mmol) 3-(3-pyridyl)-acrylic acid, 2.4 g (14.6 mmol) CDI and 4.5 g (13.3 mmol) 4-(4-diphenyl-methyl-piperazin-1-yl)-3-hydroxy-butylamine. The addition of the amine occurs at −10° C. Subsequently, this is stirred further for an hour at 0° C.

In the purification, chromatography first occurs with $CHCl_3/CH_3OH$ (95/5); subsequently, crystallization occurs once from 20 ml ethanol and twice each from 50 ml acetic acid ethyl ester: Colorless crystals of MP. 168–171° C.; yield 0.4 g (6%).

$C_{29}H_{34}N_4O_2$ (470.6)

IR-Spectrum (KBr): n(NH) 3270 $cm^{-1}$ n(C=O) 1660 1565 $cm^{-1}$ n(C=C) 1615 $cm^{-1}$ ¹H-NMR-Spectrum (CDCl₃): 1.25–2.00 (2H, m, C—CH₂—C) 2.05–2.85 (10H, m, piperazine, N—CH₂) 3.00–3.60 (2H, m, CH—OH) 3.60–4.00 (2H, m, CONHC H₂) 4.22 (1H, s, Ar₂CH) 6.44 (1H, d, CH=CHCO, J=15.7 Hz) 6.60–8.85 (1H, m, NH) 6.95–7.60 (11H, m, Ar, Py) 7.58 (1H, d, CH=CHCO, J=15.7 Hz) 7.65–7.90 (1H, m, Py) 8.45–8.65 (1H, m, Py) 8.65–8.85 (1H, m, Py)

Example 4

N-[(4-(4-diphenylmethyl-piperazin-1-yl)-4-oxo-butyl]-3-pyridin-3-yl-acrylamide (Substance 31)

Production Analogous to Example 1.

Batch size: 2.3 g (15.4 mmol) 3-(3-pyridyl)-acrylic acid, 4 ml (46.8 mmol) oxalyl chloride and 5.2 g (15.4 mmol) 4-(4-diphenyl-methyl-piperazin-1-yl)-4-oxo-butylamine.

In the purification, chromatography first occurs with CHCl₃/CH₃OH (90/10) subsequently, crystallization occurs twice from 400 ml acetic acid ethyl ester and 300 ml ethyl methyl ketone: colorless crystals of MP. 179–180° C.; yield 3.2 g (45%).

$C_{29}H_{32}N_4O_2$ (468.6)

IR-Spectrum (Kbr): n(NH) 3240 cm⁻¹ n(C=O) 1665, 1550 cm⁻¹ n(C=C) 1630 cm⁻¹

¹H-NMR-Spectrum (CDCl₃): 1.70–2.10 (2H, m, C—CH₂—C) 2.15–2.65 (6H, m, piperazine, CO—CH₂) 3.20–3.80 (6H, m, CONHCH₂, piperazine) 4.20 (1H, s, Ar₂CH) 6.45 (1H, d, CH=CHCO, J=15.7 Hz) 6.75–7.00 (1H, m, NH) 7.05–7.55 (11H, m, Ar, Py) 7.58 (1H, d, CH=CHCO, J=15.7 Hz) 7.70–7.90 (1H, m, Py) 8.45–8.65 (1H, m, Py) 8.65–8.85 (1H, m, Py)

Example 5

N-[3-(4-diphenylmethyl-piperazin-1-yl-sulfonyl)-propyl]-3-pyridin-3-yl-acrylamide (Substance 32)

Production Analogous to Example 1.

Batch size: 0.5 g (3.3 mmol) 3-(3-pyridyl)-acrylic acid, 2 ml (23.4 mmol) oxalyl chloride and 1.24 g (3.3 mmol) 3-(4-diphenyl-methyl-piperazin-1-yl-sulfonyl)-propylamine.

In the purification, chromatography first occurs CHCl₃/CH₃OH (95/5); subsequently, crystallization occurs from 75 ml acetic acid ethyl ester: colorless crystals of MP. 167–168° C.; yield 0.7 g (84%).

$C_{28}H_{32}N_4O_3S$ (504.6)

IR-Spectrum (KBr): n(NH) 3360 cm⁻¹ n(C=O) 1660, 1540 cm⁻¹ n(C=C) 1630 cm⁻¹

¹H-NMR-Spectrum (CDCl₃):

2.00–2.35 (2H, m, C—CH₂—C) 2.35–2.65 (4H, m, piperazine) 3.00 (2H, t, SO₂—CH₂, J=7.1 Hz) 3.20–3.40 (4H, m, piperazine) 3.57 (2H, dt, CONHCH₂, J=6.4 Hz, J=12.8 Hz) 4.27 (1H, s, Ar₂CH) 6.10–6.35 (1H, m, NH) 6.47 (1H, d, CH=CHCO, J=15.7 Hz) 7.05–7.55 (11H, m, Ar, Py) 7.63 (1H, d, CH=CHCO, J=15.7 Hz) 7.70–7.95 (1H, m, Py) 8.50–8.65 (1H, m, Py) 8.70–8.85 (1H, m, Py)

Example 6

N-{2-[2-(4-diphenylmethyl-piperazin-1-yl)-ethoxy]-ethyl}-3-pyridin-3-yl-acrylamide trihydrochloride (substance 35 as trihydrochloride)

Production Analogous to Example 1.

Batch size: 6.0 g (40 mmol) 3-(3-pyridyl)-acrylic acid, 9.4 ml (110 mmol) oxalyl chloride and 12.4 g (36.5 mmol) 2-[2-(4-diphenylmethyl-piperazin-1-yl)-ethoxy]-ethylamine. The crude product is chromatographically pre-purified over silica gel with CHCl₃/CH₃OH (98/2 to 95/5). After removal of the solvent, the residue is dissolved in isopropanol and mixed with isopropanolic HCl solution. The mixture is rotated in and the HCl salt is cyrstallized from 50 ml methanol/6 drops diisopropyl ether: Colorless crystals of MP. 157–159° C.; yield 0.6 g (3%).

$C_{29}H_{34}N_4O_2 \cdot 3HCl$ (580.0)

IR-Spectrum (Kbr): n(NH) 3240 cm⁻¹ n(C=O) 1670, 1550 cm⁻¹ n(C=C) 1630 cm⁻¹

¹H-NMR-Spectrum (CD₃OD): 3.40–4.00 (16H, m, piperazine, CH₂—CH₂—O—CH₂—CH₂) 5.58 (1H, s, Ar₂CH) 7.14 (1H, d, CH=CHCO, J=15.8 Hz) 7.30–7.95 (10H, m, Ar) 7.67 (1H, d, CH=CHCO, J=15.8 Hz) 8.10–8.25 (1H, m, Py) 8.80–9.00 (2H, m, Py) 9.15–9.20 (1H, m, Py)

Example 7

N-{4-(4-(bis-(4-fluorophenyl)-[methyl)-piperazin-1-yl]-but-2-in-yl}-3-pyridin-3-yl-acrylamide.trihydrachloride (Substance 47 as Trihydrochloride)

Production Analogous to Example 1.

Batch size: 2.5 g (16.9 mmol) 3-(3-pyridyl)-acrylic acid, 2 ml (23 mmol) oxalyl chloride and 6.0 g (16.9 mmol) 4-{4-[bis-(4-fluorophenyl)-methyl]-piperazin-1-yl}-but-2-inylamine.

The crude product is chromatographically pre-purified over silica gel with CHCl₃/CH₃OH (95/5). After removal of the solvent, the residue is dissolved in methanol and mixed with methanolic HCl solution. The drawn off HCl salt is first crystallized from isopropanol and subsequently from ethanol/diisopropylether: Colorless crystals of MP. 160–163° C.; yield 3.5 g (35%).

$C_{29}H_{28}F_2N_4O \cdot 3HCl$ (595.9)

IR-Spectrum (KBr): n(NH) 3240 cm⁻¹ n(C=O) 1670, 1550 cm⁻¹ n(C=C) 1630 cm⁻¹

¹H-NMR-Spectrum (D₂O): 2.95–3.55 (8H, m, piperazine) 3.80–4.10 (4H, m, CH₂—CC—CH₂) 5.04 (1H, s, Ar₂CH) 6.72 (1H, d, CH=CHCO, J=15.9 Hz) 6.85–7.60 (9H, m, Ar, CH=CHCO) 7.80–8.00 (1H, m, Py) 8.50–8.70 (2H, m, Py) 8.70–8.85 (1H, m, Py)

Example 8

3-pyridin-3-yl-N-{4-[4-(1,2,3,4-tetrahydronaphthalin-1-yl)-piperazin-1-yl]-butyl}-acrylamide (Substance 87)

Production Analogous to Example 2.

Batch size: 2.7 g (18 mmol) 3-(3-pyridyl)-acrylic acid, 3.15 g (19 mmol) CDI and 5.0 g (17.4 mmol) 4-[4-(1,2,3,4-tetrahydro-naphthalin-1-yl)-piperazin-1-yl]-butylamine.

In the purification, chromatography first occurs with CHCl₃/CH₃OH (95/5 to 90/10); subsequently, crystallization occurs twice each from 40 ml 1-chlorobutane: Colorless crystals of MP. 110–114° C.; yield 3.7 g (50%).

$C_{26}H_{34}N_4O$ (418,6)

IR-Spectrum (Kbr): n(NH) 3300 cm⁻¹ n(C=O) 1650, 1530 cm⁻¹ n(C=C) 1620 cm⁻¹

¹H-NMR-Spectrum (CDCl₃): 1.40–2.10 (8H, m, C—CH₂—CH₂—C, cyclohexyl) 2.25–3.10 (12H, m, piperazine, N—CH₂, cyclohexyl) 3.30–3.60 (2H, m, CONHC$\underline{H}_2$) 3.70–4.00 (1H, m, cyclohexyl) 6.50 (1H, d, CH=C$\underline{H}$CO, J=15.7 Hz) 6.90–7.45 (5H, m, Ar, Py, NH) 7.62 (1H, d, C$\underline{H}$=CHCO, J=15.7 Hz) 7.50–7.90 (2H, m, Py, Ar) 8.50–8.65 (1H, m, Py) 8.70–8.80 (1H, m, Py)

Example 9

3-pyridin-3-yl-N-[4-(4-{5,6,7,8-tetrahydro-naphthalin-1-yl}-piperazin-1-yl)-butyl]-acrylamide (Substance 94)

1.6 g (11.1 mmol) 3-(3-pyridyl)-acrylic acid and 6.2 ml (44.3 mmol) TEA are suspended in 80 ml absolute dichloromethane and cooled to ca. 0° C. under moisture exclusion. 2.0 g (12.1 mmol) 81% HOBT and 2.3 g (12.1 mmol) EDC are added and the mixture is stirred for 30 min under ice cooling. 4.0 g (10.1 mmol) 4-[4-(5,6,7,8-tetrahydro-naphthalin-1-yl)-piperazin-1-yl]-butylamine are added and the mixture is stirred without cooling overnight at RT. Subsequently, the batch is washed twice with 25 ml 2M sodium hydroxide solution and 25 ml water. The organic phase is dried over sodium sulfate and the solvent is removed under vacuum. The residue is chromatographically pre-purified over silica gel with CHCl$_3$/CH$_3$OH (95/5) and crystallized twice from acetonitrile (25 ml and 15 ml): Colorless crystals of MP. 108–109° C.; yield 2.7 g (64%).

$C_{26}H_{34}N_4O$ (418.6)

IR-Spectrum (Kbr): n(NH) 3260 cm$^{-1}$ n(C=O) 1650, 1555 cm$^{-1}$ n(C=C) 1620 cm$^{-1}$ $^1$H-NMR-Spectrum (CDCl$_3$): 1.40–2.10 (8H, m, C—CH$_2$—CH$_2$—C, cyclohexyl) 2.25–3.30 (14H, m, piperazine, N—CH$_2$, cyclohexyl) 3.30–3.70 (2H, m, CONHC$\underline{H}_2$) 6.51 (1H, d, CH=C$\underline{H}$CO, J=15.6 Hz) 6.70–7.45 (5H, m, Ar, Py, NH) 7.63 (1H, d, C$\underline{H}$=CHCO, J=15.6 Hz) 7.70–7.95 (1H, m, Py) 8.45–8.65 (1H, m, Py) 8.65–8.85 (1H, m, Py)

Example 10

N-{4-[(naphthalin-1-yl)-piperazin-1-yl]-butyl}-3-pyridin-3-yl-acrylamide (Substance 97)

Production Analogous to Example 1.

Batch size: 3.38 g (22.7 mmol) 3-(3-pyridyl)-acrylic acid, 7.85 g (61.8 mmol) oxalyl chloride and 8.55 g (20.6 mmol) 4-[(naphtha-lin-1-yl)-piperazin-1-yl]-butylamine.

In the recovery, 40 ml 10% sodium hydroxide solution is added to the reaction solution. The aqueous phase is extracted with dichloromethane. The combined organic phases are washed with 15 ml water, dried over sodium sulfate and the solvent is removed under vacuum. The residue is chromatographically purified over silica gel with CHCl$_3$/CH$_3$OH (98/2 to 96/4).

After removal of the solvent, this is crystallized three times each with 40 ml acetic acid ethyl ester under addition of 5 drops diisopropylether respectively: solid with MP 124–125° C.; yield 1.5 g (18%).

$C_{26}H_{30}N_4O$ (414.6)

IR-Spectrum (KBr): n(NH) 3280 cm$^{-1}$ n(C=O) 1650, 1545 cm$^{-1}$ n(C=C) 1620 cm$^{-1}$ $^1$H-NMR-Spectrum (CDCl$_3$): 1.45–1.95 (4H, m, C—CH$_2$—CH$_2$—C) 2.30–3.40 (10H, m, piperazine, N—CH$_2$) 3.30–3.60 (2H, m, CONHC$\underline{H}_2$) 6.50 (1H, d, CH=C$\underline{H}$CO, J=15.7 Hz) 6.55–6.85 (1H, m, NH) 6.95–7.95 (8H, m, Ar, Py) 7.63 (1H, d, C$\underline{H}$=CHCO, J=15.7 Hz) 8.05–8.35 (1H, m, Py) 8.50–8.70 (1H, m, Py) 8.70–8.85 (1H, m, Py)

Example 11

N-{2-[4-(6,11-dihydrodibenzo[b,e]thiepin-11-yl)-piperazin-1-yl]-ethyl}-3-pyridin-3-yl-acrylamide (Substance 138)

5.0 g (14.1 mmol) N-[2-(piperazin-1-yl)-ethyl]-3-pyridin-3-yl-acrylamidetrihydrochloride (substance 317 as trihydrochloride) and 5.8 ml (42.3 mmol) TEA are suspended in 65 ml absolute dichloromethane. 4.7 g (15.5 mmol) 11-methanesulfonyloxy-6,11-dihydrodibenzo[b,e]thiepine dissolved in 60 ml absolute dichloromethane is added dropwise under moisture exclusion. The mixture is stirred overnight at RT. Subsequently, the batch is washed three times each with 50 ml water. The organic phase is dried over sodium sulfate and the solvent is removed under vacuum. The residue is chromatographically purified over silica gel with CHCl$_3$/CH$_3$OH (95/5). Subsequently, a further purification occurs by means of MPLC with CHCl$_3$/CH$_3$OH (95/5): yield 4.3 g (44%) as an amorphic solid.

$C_{29}H_{30}N_4OS$ (470,6)

IR-Spectrum (Kbr): n(NH) 3270 cm$^{-1}$ n(C=O) 1655, 1535 cm$^{-1}$ n(C=C) 1620 cm$^{-1}$ $^1$H-NMR-Spectrum (CDCl$_3$): 2.00–2.90 (10H, m, piperazine, piperazin-CH$_2$) 3.20–3.70 (3H, m, CONHC$\underline{H}_2$, SCH$_2$) 4.10 (1H, s, Ar$_2$CH) 5.90–6.50 (2H, m, NH, SCH$_2$) 6.49 (1H, d, CH=C$\underline{H}$CO, J=15.7 Hz) 6.90–7.50 (9H, m, Ar, Py) 7.62 (1H, d, C$\underline{H}$=CHCO, J=15.7 Hz) 7.75–7.95 (1H, m, Py) 8.50–8.70 (1H, m, Py) 8.70–8.90 (1H, m, Py)

Example 12

N-[4-(4-biphenyl-2-yl-piperazin-1-yl)-butyl)-3-pyridin-3-yl-acrylamide (Substance 68)

Production Analogous to Example 1.

Batch size: 5.8 g (39.1 mmol) 3-(3-pyridyl)-acrylic acid, 9.1 ml (106 mmol) oxalyl chloride and 5.0 g (16.1 mmol) 4-(4-biphenyl-2-yl-piperazin-1-yl)-butylamine.

In the recovery, 60 ml 10% sodium hydroxide solution is added to the reaction solution. The aqueous phase is extracted twice each with 15 ml dichloromethane. The combined organic phases are washed twice each with 15 ml water, dried over sodium sulfate and the solvent is removed under vacuum. The residue is chromatographically purified over silica gel with CHCl$_3$/CH$_3$OH/NH$_4$OH (85/15/2). After removal of the solvent, this is crystallized twice with 1-chlorobutane: solid with MP. 115° C.; yield 3.3 g (46%).

$C_{28}H_{32}N_4O$ (440.6)

IR-Spectrum (Kbr): n(NH) 3280 cm$^{-1}$ n(C=O) 1650, 1545 cm$^{-1}$ n(C=C) 1620 cm$^{-1}$ $^1$H-NMR-Spectrum (CDCl$_3$): 1.35–2.85 (4H, m, C—CH$_2$—CH$_2$—C) 2.10–2.55 (6H, m, piperazine, N—CH$_2$) 2.75–3.00 (4H, m, piperazine) 3.20–3.50 (2H, m, CONHC$\underline{H}_2$) 6.44 (1H, d, CH=C$\underline{H}$CO, J=15.6 Hz) 6.45–6.70 (1H, m, NH) 6.95–7.85 (12H, m, Ar, C$\underline{H}$=CHCO, Py) 8.45–8.65 (1H, m, Py) 8.65–8.80 (1H, m, Py)

Example 13

N-{4-[4-(9H-fluoroen-9-yl)-piperazin-1-yl]-butyl}-3-pyridin-3-yl-acrylamide (Substance 101)

Production Analogous to Example 1.

Batch size: 19.2 g (129 mmol) 3-(3-pyridyl)-acrylic acid, 15.1 ml (176 mmol) oxalyl chloride and 37.6 g (117 mmol) 4-(9-fluoroenyl-piperazin-1-yl)-butylamine.

In the recovery, 150 ml 10% sodium hydroxide solution is added to the reaction solution: The organic phase is washed three times each with 60 ml water, dried over sodium sulfate and the solvent is removed under vacuum. The residue is chromatographically purified over silica gel with CHCl$_3$/CH$_3$OH (90/10). After removal of the solvent, this is crystallized with 1700 ml acetic acid ethyl ester: solid with MP. 145–147° C.; yield 39.0 g (73%).

C$_{29}$H$_{32}$N$_4$O (452.6)

IR-Spectrum (Kbr): n(NH) 3300 cm$^{-1}$ n(C=O) 1655, 1530 cm$^{-1}$ n(C=C) 1620 cm$^{-1}$ $^1$H-NMR-Spectrum (CDCl$_3$): 1.35–1.80 (4H, m, C—CH$_2$—CH$_2$—C) 2.10–2.80 (10H, m, piperazine, N—CH$_2$) 3.20–3.50 (2H, m, CONHC$\underline{H}_2$) 4.81 (1H, s, Ar$_2$CH) 6.34 (1H, d, CH=C$\underline{H}$CO, J=15.7 Hz) 6.75–7.05 (1H, m, NH) 7.00–7.80 (11H, m, Ar, C$\underline{H}$=CHCO, Py) 8.40–8.60 (1H, m, Py) 8.60–8.70 (1H, m, Py)

Example 14

N-{4-[4-(10,11-dihydro-5H-dibenzo[a,d]cyclohepten-5-yl)-piperazin-1-yl]-butyl}-3-pyridin-3-yl-acrylamide (substance 119)

Production Analogous to Example 1.

Batch size: 4.16 g (27.9 mmol) 3-(3-pyridyl)-acrylic acid, 6.5 ml (76.2 mmol) oxalyl chloride and 12.2 g (25.4 mmol) 4-[4-(10,11-dihydro-5H-dibenzo[a,d]cyclohepten-5-yl)-piperazin-1-yl]-butylamine.

In the recovery, 50 ml 10% sodium hydroxide solution is added to the reaction solution. The aqueous phase is extracted with dichloromethane. The combined organic phases are washed with 50 ml water, dried over sodium sulfate and the solvent is removed under vacuum. The residue is chromatographcially pre-purified over silica gel with CHCl$_3$/CH$_3$OH (98/2 to 90/10). After removal of the solvent, this is crystallized four-fold each with 50 ml acetic acid ethyl ester: Colorless solid with MP. 119–1200° C.; yield 4.9 g (40%).

C$_{31}$H$_{36}$N$_4$O (480.7)

IR-Spectrum (Kbr): n(NH) 3280 cm$^{-1}$ n(C=O) 1670, 1540 cm$^{-1}$ n(C=C) 1625 cm$^{-1}$ $^1$H-NMR-Spectrum (CDCl$_3$): 1.40–1.80 (4H, m, C—(CH$_2$)$_2$—C) 2.10–2.55 (10H, m, piperazine, N—CH$_2$) 2.55–3.00 (2H, m, Ar—CH$_2$—CH$_2$—Ar) 3.20–3.50 (2H, m, CONHC$\underline{H}_2$) 4.75–4.20 (3H, m, Ar$_2$CH, Ar—CH$_2$—CH$_2$—Ar) 6.50 (1H, d, CH=C$\underline{H}$CO, J=15.7 Hz) 6.90–7.40 (10H, m, Ar, Py, NH) 7.61 (1H, d, C$\underline{H}$=CHCO, J=15.7 Hz) 7.70–7.85 (1H, m, Py) 8.50–8.65 (1H, m, Py) 8.70–8.80 (1H, m, Py)

Example 15

N-[2-(4-diphenylacetyl-piperazin-1-yl)-ethyl]-3-pyridin-3-yl-acrylamide (Substance 158)

8.0 g (22.6 mmol) N-[2-(piperazin-1-yl)-ethyl]-3-pyridin-3-yl-acrylic amide trihydrochloride (substance 317 as a trihydrochloride) and 13 ml (92.7 mmol) TEA are present in 100 ml absolute dichloromethane and cooled to ca. 0° C. under moisture exclusion. 6.3 g (24.9 mmol) diphenylacetyl chloride (90%) are dissolved in 70 ml absolute dichloromethane and added dropwise. The mixture is stirred overnight at RT without further cooling. Subsequently, 200 ml dichloromethane are added and the batch is washed three times each with 100 ml water. The organic phase is dried over sodium sulfate and the solvent is removed under vacuum. The residue is crystallized twice from 40 ml and 30 ml acetonitrile. Beige coloured crystals of MP. 1740° C. yield 4.6 g (44%).

C$_{28}$H$_{30}$N$_4$O$_2$ (454.6)

IR-Spectrum (Kbr): n(NH) 3320 cm$^{-1}$ n(C=O) 1675, 1550 cm$^1$ n(C=C) 1610 cm$^1$ $^1$H-NMR-Spectrum (CDCl$_3$): 2.10–2.60 (6H, m, piperazine, N—CH$_2$) 3.30–3.85 (6H, m, piperazine, CONHC$\underline{H}_2$) 5.20 (1H, s, Ar$_2$CH) 6.20–6.40 (1H, m, NH) 6.46 (1H, d, CH=C$\underline{H}$CO, J=15.7 Hz) 7.10–7.40 (11H, m, Ar, Py) 7.61 (1H, d, C$\underline{H}$=CHCO, J=15.7 Hz) 7.70–7.90 (1H, m, Py) 8.50–8.65 (1H, m, Py) 8.70–8.80 (1H, m, Py)

Example 16

N-{2-[4-(10,11-dihydro-dibenzo[b,f]azepin-5-yl-carbonyl)-piperazin-1-yl-ethyl}-3-pyridin-3-yl-propionamide (substance 215)

Production Analogous to Example 15.

Batch size: 8.0 g (21.5 mmol) N-[2-(piperazin-1-yl)-ethyl]-3-pyridin-3-yl-propionamide-trihydrochloride, 12.3 ml (88.1 mmol) TEA and 6.1 g (23.6 mmol) 10,11-dihydro-dibenzo[b,f]azepin-5-carbonyl chloride in 170 ml absolute dichloromethane.

In the purification, this is first chromatographically pre-purified over silica gel with CHCl$_3$/CH$_3$OH (100/0 to 90/10) and, after removal of the solvent, crystallized from 10 ml acetonitrile. Colorless crystals of MP. 146–147° C. yield 0.7 g (6%).

C$_{29}$H$_{33}$N$_5$O$_2$ (483.6)

IR-Spectrum (KBr): n(NH) 3330 cm$^{-1}$ n(C=O) 1660, 1535 cm$^{-1}$ n(C=C) 1630 cm$^{-1}$ $^1$H-NMR-Spectrum (CDCl$_3$) 2.10–2.60 (8H, m, piperazine, CO—CH$_2$, N—CH$_2$) 2.96 (2H, t, Py-CH$_2$, J=7.4 Hz) 3.10–3.45 (10H, m, CONHC$\underline{H}_2$, piperazine, Ar—CH$_2$—CH$_2$—Ar) 5.80–6.00 (1H, m, NH) 7.00–7.60 (10H, m, Ar, Py) 8.35–8.55 (2H, m, Py)

Example 17

N-{2-[4-(naphthalin-2-yl-sulfonyl)-piperazin-1-yl]-ethyl}-3-pyridin-3-yl-acrylamide (Substance 227)

Production Analogous to Example 15.

Batch size: 8.0 g (22.6 mmol) N-(2-(piperazin-1-yl)-ethyl]-3-pyridin-3-yl-acrylamide.trihydrochloride (substance 317 as a trihydrochloride), 13 ml (92.7 mmol) TEA and 5.6 g (24.9 mmol) naphthalin-2-sulfonic acid chloride in 180 ml absolute dichloromethane.

For purification, this is crystallized twice from 150 ml and 100 ml acetonitrile. Beige coloured crystals of MP. 183–184° C. yield 4.0 g (39%).

C$_{24}$H$_{26}$N$_4$O$_3$S (450.6)

IR-Spectrum (Kbr): n(NH) 3250 cm$^{-1}$ n(C=O) 1665, 1555 cm$^{-1}$ n(C=C) 1625 cm$^{-1}$ $^1$H-NMR-Spectrum (CDCl$_3$): 2.35–2.80 (6H, m, piperazine, N—CH$_2$) 3.00–3.35 (4H, m, piperazine) 3.44 (2H, dd, CONHC$\underline{H}_2$, J=5.5 Hz, J=11.2 Hz) 5.90–6.15 (1H, m, NH) 6.35 (1H, d, CH=C$\underline{H}$CO, J=15.6 Hz) 7.15–8.15 (9H, m, Ar, C$\underline{H}$=CHCO, Py) 8.35 (1H, bs, Ar) 8.45–8.60 (1H, m, Py) 8.60–8.75 (1H, m, Py)

Example 18

N-{2-[4-(tert-butoxycarbonyl)-piperazin-1-yl]-ethyl]-3-pyridin-3-yl-acrylamide (Substance 374)

Production Analogous to Example 1.

Batch size: 36.1 g (242 mmol) 3-(3-pyridyl)-acrylic acid, 23.1 ml (264 mmol) oxalyl chloride, 50 g (15.4 mmol)

2-[4-(tert-but-oxycarbonyl)-piperazin-1-yl]-ethylamine and 30.4 ml (220 mmol) TEA in 400 ml absolute dichloromethane.

In the purification, this is crystallized twice from 100 ml acetic acid ethyl ester and 150 ml 1-chlorbutane: Colorless crystals of MP. 92–93° C.; yield 38.4 g (48%).

$C_{19}H_{28}N_1O_3$ (360.5)

IR-Spectrum (Kbr): n(NH) 3320 cm$^{-1}$ n(C=O) 1670, 1530 cm$^{-1}$ n(C=C) 1620 cm$^{-1}$ $^1$H-NMR-Spectrum (CDCl$_3$): 1.47 (9H, s, tert. Butyl 2.30–2.80 (6H, m, piperazine, 1N—CH$_2$) 3.30–3.70 (6H, m, piperazine CONHC$\underline{H}_2$) 6.30–6.55 (1H, m, NH) 6.52 (1H, d, CH=C$\underline{H}$CO, J=15.7 Hz) 7.20–7.40 (1H, m, Py) 7.63 (1H, d, C$\underline{H}$=CHCO, J=15.7 Hz) 7.70–7.90 (1H, m, Py) 8.45–8.65 (1H, m, Py) 8.65–8.85 (1H, m, Py)

Example 19

N-[2-(piperazin-1-yl)-ethyl]-3-pyridin-3-yl-acrylamide.trihydrochloride (Substance 317 as a Trihydrochloride)

38 g (105 mmol) N-{2-[4-(tert-butoxycarbonyl)-piperazin-1 yl}-ethyl]-3-pyridin-3-yl-acrylamide (substance 374) are dissolved in 380 ml methanol and 42 ml concentrated hydrochloric are added. The mixture is stirred for four hours under reflux. After cooling of the solution, the solvent is removed under vacuum. The residue is crystallized from 185 ml methanol. Colorless crystals of MP. 216–226° C. (under decomposition) yield 34.8 g (93%).

$C_{14}H_{20}N_4O.3HCl$ (369,7)

IR-Spectrum (Kbr): n(NH) 3150 cm$^{-1}$ n(C=O) 1670, 1540 cm$^{-1}$ n(C=C) 1610 cm$^{-1}$ $^1$H-NMR-Spectrum (D$_2$O): 3.20–3.75 (12H, m, piperazine, N—CH$_2$—CH$_2$) 6.74 (1H, d, CH=C$\underline{H}$CO, J=15.9 Hz) 7.44 (1H, d, C$\underline{H}$=CHCO, J=15.9 Hz) 7.80–8.00 (1H, m, Py) 8.50–8.70 (2H, m, Py) 8.80–8.90 (1H, m, Py)

In the following Table 2, further synthesized end products according to formula (I) are listed:

TABLE 2

synthesized compounds of formula (I)

| Nr | R$^1$–R$^3$ | A | D—E—G | mp. [° C.] (solvent)$^1$ |
|----|-------------|---|-------|--------------------------|
| 1 | H | CH$_2$CH$_2$ | CH$_2$CH$_2$CH$_2$CH$_2$—N(piperazine)NH | oil$^1$ |
| 2 | H | CH=CH | CH$_2$CH$_2$CH$_2$CH$_2$—N(piperazine)NH | 240–242'" (EtOH) |
| 25 | H | CH$_2$NHCH$_2$CH$_2$ | CH$_2$CH$_2$—N(piperazine)N—CH(C$_6$H$_5$)$_2$ | amorph$^{2,"}$ (CHCl$_3$/MeOH/NH$_3$ 90/9/1) |
| 27 | H | OCH$_2$ | CH$_2$CH$_2$CH$_2$CH$_2$—N(piperazine)N—CH(C$_6$H$_5$)$_2$ | 91–93 (PE) |
| 29 | H | CH=CH | CH$_2$CH$_2$CHCH$_2$—N(piperazine)N—CH(C$_6$H$_5$)$_2$, OH | 168–171 (EE) |
| 30 | H | CH=CH | OCH$_2$CH$_2$CH$_2$—N(piperazine)N—CH(C$_6$H$_5$)$_2$ | 105–107 (EE) |

TABLE 2-continued synthesized compounds of formula (I)

| Nr | R¹–R³ | A | D—E—G | mp. [° C.] (solvent)[1] |
|---|---|---|---|---|
| 31 | H | CH=CH | CH₂CH₂CH₂C(=O)—N(piperazine)N—CH(C₆H₅)₂ | 179–180 (MEK) |
| 32 | H | CH=CH | CH₂CH₂CH₂SO₂—N(piperazine)N—CH(C₆H₅)₂ | 167–168 (EE) |
| 33 | H | CH=CH | CH₂CH₂NH—C(=O)—N(piperazine)N—CH(C₆H₅)₂ | 187–188 (iPrOH) |
| 35 | H | CH=CH | CH₂CH₂OCH₂CH₂—N(piperazine)N—CH(C₆H₅)₂ | 157–159[3] (MeOH/iPr₂O) |
| 36 | H | CH=CH | CH₂CH₂CH₂C≡CCH₂—N(piperazine)N—CH(C₆H₅)₂ | 162–164° (90% iPrOH) |
| 37 | H | CH=CH | CH₂C≡C—CH=CHCH₂—N(piperazine)N—CH(C₆H₅)₂ | amorph[2] (CHCl₃/MeOH) |
| 38 | H | CH=CH | CH₂CH₂CH₂CH₂—N(2,5-diMe-piperazine)N—CH(C₆H₅)₂ | 141–145[3] (EtOH) |
| 42 | H | CH=CH | CH₂CH₂CH₂CH₂—N(2,5-diazabicyclic)N—CH(C₆H₅)₂ | 125–127 (MeCN) |
| 47 | H | CH=CH | CH₂C≡CCH₂—N(piperazine)N—CH(4-F-C₆H₄)₂ | 160–163[3] (EtOH/iPr₂O) |

TABLE 2-continued synthesized compounds of formula (I)

| Nr | R¹–R³ | A | D—E—G | mp. [° C.] (solvent)[1] |
|----|-------|---|-------|-------------------------|
| 60 | H | OCH$_2$ | CH$_2$CH$_2$CH$_2$CH$_2$—N(piperazine)N—CH(phenyl)(3-pyridyl) | resin[2] (CHCl$_3$/MeOH/NH$_3$ 90/9/1) |
| 68 | H | CH=CH | CH$_2$CH$_2$CH$_2$CH$_2$—N(piperazine)N—(2-C$_6$H$_5$-phenyl) | 115 (BuCl) |
| 75 | H | CH=C(CH$_3$) | CH$_2$CH$_2$CH$_2$CH$_2$—N(piperazine)N—(2-C$_6$H$_5$-phenyl) | 186–188″ (EtOH) |
| 83 | H | CH=CH | CH$_2$CH$_2$CH$_2$CH$_2$—N(piperazine)N—(4-C$_6$H$_5$-phenyl) | 178–180 (iPrOH) |
| 86 | H | CH$_2$CH$_2$ | CH$_2$CH$_2$CH$_2$CH$_2$—N(piperazine)N—(1-tetrahydronaphthyl) | 93 (BuCl) |
| 87 | H | CH=CH | CH$_2$CH$_2$CH$_2$CH$_2$—N(piperazine)N—(1-tetrahydronaphthyl) | 110–114 (BuCl) |
| 93 | H | CH$_2$CH$_2$ | CH$_2$CH$_2$CH$_2$CH$_2$—N(piperazine)N—(5,6,7,8-tetrahydronaphthyl) | 81–82 (MeCN) |
| 94 | H | CH=CH | CH$_2$CH$_2$CH$_2$CH$_2$—N(piperazine)N—(5,6,7,8-tetrahydronaphthyl) | 108–109 (MeCN) |

TABLE 2-continued
synthesized compounds of formula (I)
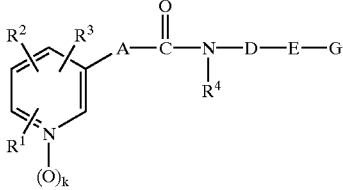
| Nr | R¹–R³ | A | D—E—G | mp. [° C.] (solvent)[1] |
|---|---|---|---|---|
| 96 | H | CH₂CH₂ | 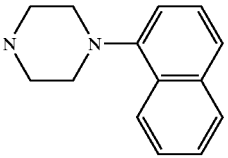 | 104–105 (EE) |
| 97 | H | CH=CH | 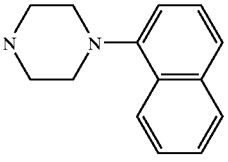 | 124–125 (EE/iPr₂O) |
| 101 | H | CH=CH | 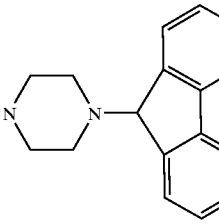 | 145–147 (EE) |
| 119 | H | CH=CH | 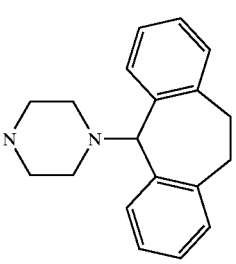 | 119–120 (EE) |
| 138 | H | CH=CH | 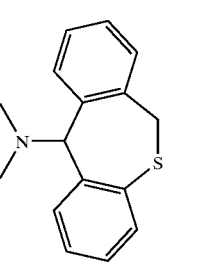 | amorph[2] (CHCl₃/MeOH) |
| 158 | H | CH=CH | 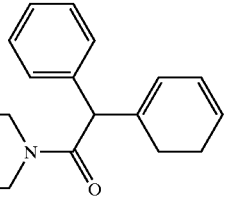 | 174 (MeCN) |

TABLE 2-continued synthesized compounds of formula (I)

| Nr | R¹–R³ | A | D—E—G | mp. [° C.] (solvent)[1] |
|---|---|---|---|---|
| 208 | H | CH=CH | CH₂CH₂—N(piperazine)N(C(=O))—N(phenyl)(phenyl) | 150 (aceton) |
| 215 | H | CH₂CH₂ | CH₂CH₂—N(piperazine)N—C(=O)—N(dibenzazepine) | 146–147 (MeCN) |
| 227 | H | CH=CH | CH₂CH₂—N(piperazine)N—SO₂—(naphthalen-2-yl) | 183–184 (MeCN) |
| 231 | H | CH=CH | CH₂CH₂—N(piperazine)N—SO₂—(quinolin-8-yl) | amorph[2] (CHCl₃/MeOH) |
| 234 | H | CH=CH | CH₂CH₂CH₂CH₂—N(piperazine)N—P(=O)(phenyl)(phenyl) | amorph[2] |
| 251 | H | CH=CH | CH₂CH₂CH₂CH₂—N(homopiperazine)N—H | Ol[2] |
| 305 | H | CH=CH | CH₂CH₂CH₂CH₂—N(homopiperazine)N—C(=O)—O—C(CH₃)₃ | Ol[2] |
| 317 | H | CH=CH | CH₂CH₂—N(piperazine)NH | 216–226/Zers.[3] (MeOH) |

TABLE 2-continued synthesized compounds of formula (I)

| Nr | R¹–R³ | A | D—E—G | mp. [° C.] (solvent)[1] |
|---|---|---|---|---|
| 349 | H | CH=CH | CH₂CH₂CH₂CH₂—N(piperazine)N—C(=O)—(2-aminophenyl) | amorph (MeCN) |
| 374 | H | CH=CH | CH₂CH₂—N(piperazine)N—C(=O)—O—C(CH₃)₃ | 92–93 (EE/BuCl) |

[1]PE = Petroleum ether
EE = Ethyl acetate
MEK = Methyl ethyl ketone
iPrOH = Isopropanol
iPr₂O = Diisopropyl ether
MeO4 = Methanol
EtOH = Ethanol
MeCN = Acetonitrile
BuCl = 1-Chlorobutane
[2]Purified by column chromatography
[3]as a Trihydrochloridee
[4]as a Tetrahydrochloride
[5]as a Trioxalate
[6]as a Sulfate Production of the Starting Substances Example A 4-(4-diphenylphosphinoyl-piperazin-1-yl)-butylamine a) N-diphenylphosphinoyl-piperazine 20 g (84.5 mmol) diphenylphosphinate chloride dissolved in 30 ml DMF are added dropwise to a solution of 21.8 g (253 mmol) piperazine in DMF. After four hours, the solution is concentrated under vacuum, taken up in chloroform and extracted by shaking with 10% hydroxide solution. The organic phase is dried over sodium sulfate and solvent is removed under vacuum. The residue is chromatographically purified over silica gel with CHCl₃/CH₃OH/TEA (90/10/0 to 90/10/6): yield 12 g (49%).

b) 2-[4-(4-diphenylphosphinoyl)-butyl]-isoindolin-1,3-dione 12 g (41.9 mmol) N-diphenylphosphinoyl-piperazine, 11.8 g (42 mmol) N-(4-bromobutyl)-phthalimide, 5.8 g (42 mmol) potassium carbonate and 1.4 g (8 mmol) potassium iodide are heated in ethyl methyl ketone for 6 hours under reflux. After cooling, the reaction mixture is concentrated under vacuum. The residue is taken up in acetic acid ethyl ester and extracted by shaking with water. The organic phase is dried over sodium sulfate and the solvent is removed under vacuum: yield 20 g (100%).

c) 4-(4-diphenylphosphinoyl-piperazin-1-yl)-butylamine 20 g (40 mmol) 2-[4-(4-diphenylphosphinoyl)-butyl]-isoindolin-1,3-dione and 4 ml (80 mmol) hydrazine hydrate are heated in 400 ml ethanol for three hours under reflux. The cooling solution is concentrated under vacuum and the residue is taken up in acetic acid ethyl ester. The suspension is filtered and the residue is washed with toluene. The filtrate and washing fluid are concentrated under vacuum until dry. Subsequently, the residue is taken up in chloroform and shaken with 10% sodium sulfate. The organic phase is dried over sodium sulfate and the solvent is removed under vacuum. The accumulated crude product is further processed without further purification: yield 13.3 g (95%).

Example B 4-(4-diphenylmethyl-piperazin-1-yl)-3-hydroxy-butylamine a) 2-(but-3-enyl)-isoindolin-1,3-dione 50 g (370 mmol) 4-bromo-1-butene and 68.5 g (370 mmol) phthalimide potassium salt are suspended in 800 ml ethyl methyl ketone and heated under reflux for 14 hours. After cooling, the mixture is filtrated and the filtrate is concentrated under vacuum. The residue is taken up in acetic acid ethyl ester and washed with water. The organic phase is dried over sodium sulfate and the solvent is removed under vacuum: yield 50 g (67%).

b) 2-(3,4-epoxybutyl)-isoindolin-1,3-dione 70 g (350 mmol) 2-(but-3-enyl)-isoindolin-1,3-dione are dissolved in dichloromethane. The solution is cooled to ca. 0° C. and a suspension of 120.8 g (350 mmol) 50% 3-chloroperoxy-benzoic acid in dichloromethane is added under cooling. The mixture is left standing without further cooling at room temperature for two days. After addition of 250 ml saturated NaHCO₃ solution the organic phase is separated and washed three times each with 200 ml saturated NaHCO₃ solution and once with water. The organic phase is dried over sodium sulfate and the solvent is removed under vacuum: yield 80 g.

c) 2-(4-(4-diphenylmethyl-piperazin-1-yl)-3-hydroxy-butyl]isoindolin-1,3-dione 5 g (~25 mmol) 2-(3,4-epoxybutyl)-isoindolin-1,3-dione, 7.5 g (30 mmol) benzhydrylpiperazine and 3.5 g (25 mmol) potassium carbonate are stirred in DMF for 6 hours 80° C. After cooling, the reaction mixture is filtered and concentrated under vacuum. The residue is taken up in 300 ml acetic acid ethyl ester and washed three times each with 20 ml water. The organic phase is dried over sodium sulfate and the solvent is removed under vacuum. The residue is chromatographically purified over silica gel with CHCl₃/CH₃OH.

d) 4-(4-diphenylmethyl-piperazin-1-yl)-3-hydroxy-butylamine 15 g (30 mmol) 2-[4-(4-diphenylmethyl-piperazin-1-yl)-3-hydroxy-butyl]-isoindolin-2,3-dione and 3.9 ml (60 mmol) hydrazine-hydrate (80%) are heated under reflux in 100 ml ethanol for three hours. The cooled solution is concentrated under vacuum and the residue is taken up in acetic acid ethyl ester. The suspension is filtrated and the residue is distributed between acetic acid ethyl ester and 10% sodium hydroxide solution. The combined organic phases are dried over sodium sulfate and concentrated under vacuum until dry. The resin is further processed without further purification: yield 4.8 g (47%).

Example C 1-(4-aminobutyryl)-4-diphenylmethyl-piperazine a) 1-(4-chlorobutyryl)-4-diphenylmethyl-piperazine 25 g (99 mmol) benzhydrylpiperazine and 15.2 ml (109 mmol) TEA are present in 200 ml absolute THF and cooled to ca. 0° C. under moisture exclusion. 14 g (99 mmol) 4-chlorobutyric chloride are dissolved in 40 ml absolute THF and added dropwise. The mixture is stirred an additional three hours at RT and subsequently filtered. The filtrate is concentrated under vacuum, the residue is taken up in acetic acid ethyl ester and washed with saturated NaCl solution. The organic phase is dried over sodium sulfate and concentrated under vacuum until dry. The resin is further processed without further purification: yield 35.1 g (99%).

b) 1-(4-aminobutyryl)-4-diphenylmethyl-piperazine 8.9 g (24.9 mmol) 1-(4-chlorobutyryl)-4-diphenylmethylpiperazine, 4.8 g (73.8 mmol) sodium azide, 1 g potassium iodide and 1 g molecular sieve 4A are stirred in 70 ml DMF for five hours at 70° C. After cooling, the reaction mixture is filtered and the filtrate is concentrated under vacuum. The accumulated crude product is dissolved in methanol and mixed with a spatula tip of palladium-carbon (10%). The mixture is stirred for two days at RT under hydrogen atmosphere. The mixture is filtered from the catalyst and the solvent is removed under vacuum. The residue is chromatographically purified over silica gel with CHCl₃/CH₃OH/TEA (90/10/5): yield 5.2 g (62%) as a colorless amorphous solid.

EXAMPLE D 3-(4-diphenylmethyl-piperazin-1-yl-sulfonyl)-propylamine a) 1-diphenylmethyl-4-(3-chloropropanesulfonyl)-piperazine 39.2 g (155 mmol) benzhydrylpiperazine and 19.7 ml (141 mmol) TEA are present in 100 ml absolute dichloromethane and cooled to ca. 0° C. under moisture exclusion. 25 g (141 mmol) 3-chloropropanesulfonyl chloride are dissolved in 70 ml absolute dichloromethane and added dropwise. The mixture is stirred for two hours under cooling and subsequently mixed with chloroform and washed with saturated NaCl solution. The organic phase is dried over sodium sulfate and concentrated under vacuum until dry. The solid is further processed without further purification: yield 59.2 g.

b) 2-[3-(4-diphenylmethyl-piperazin-1-yl-sulfonyl)-propyl]isoindolin-1,3-dione

The reaction of the halogenide to phthalimide occurs analogously to Example B)a).

Batch size: 15 g (38 mmol) 1-diphenylmethyl-4-(3-chloropropane sulfonyl)-piperazine and 7.2 g (39 mmol) phthalimide-potassium salt in DMF at 80° C.

The purification occurs by chromatography on silica gel with petroleum ether/acetic acid ethyl ester (4/1). Yield 14 g (71%).

c) 3-(4-diphenylmethyl-piperazin-1-yl-sulfonyl)-propylamine

The reaction of the phthalimide to the amine occurs analogously to Example B)d).

Batch size: 149 (27.8 mmol) 2-[3-(4-diphenylmethyl-piperazin-1-yl-sulfonyl)-propyl)-isoindolin-1,3-dione and 2.8 ml (55.6 mmol) hydrazine.hydrate.

The resulting resin is further processed without further purification: Yield 1.5 g (15%).

EXAMPLE E

2-[2-(4-diphenylmethyl-piperazin-1-yl)-ethoxy]-ethylamine a) 2-(2-(4-diphenylmethyl-piperazin-1-yl)-ethoxy]-ethanol 71.7 g (284 mmol) benzhydrylpiperazine, 45 g (361 mmol) 2-(2-chloroethoxy)-ethanol, 43.2 g (312 mmol) potassium carbonate and 9.4 g (57 mmol) potassium iodide are stirred in 400 ml absolute DMF for 8 hours at 75° C. After cooling, the solution is concentrated under vacuum. The residue is distributed between acetic acid ethyl ester and water. The aqueous phase is extracted twice with acetic acid ethyl ester and the combined organic phases are washed three times with saturated sodium chloride solution. The organic phase is dried over sodium sulfate and the solvent is removed under vacuum. The residue is chromatographically purified over silica gel with CHCl₃/CH₃OH (90/10): Yield 104 g.

b) 2-{2-[2-(4-diphenylmethyl-piperazin-1-yl)-ethoxy]-ethyl}-isoindolin-1,3-dione 40 g (~118 mmol) 2-[2-(4-diphenylmethyl-piperazin-1-yl)-ethoxy]-ethanol, 31.1 g (119 mmol) triphenylphosphine and 17.3 g (118 mmol) phthalimide are suspended in 200 ml THF and 24.2 ml (119 mmol) are azodicarbonic acid diethyl ester are added dropwise under protective atmosphere and light cooling (to Ca. 15° C.). The mixture is stirred without further cooling for three hours and subsequently, the solvent is removed under vacuum. The residue is taken up in 1N HCl and washed twice each with 50 ml acetic acid ethyl ester respectively. The aqueous phase is neutralized with ca. 50 g sodium hydrogen carbonate and extracted four times each with 125 ml chloroform. The combined chloroform phases are dried over sodium sulfate and the solvent is removed under vacuum. The residue is chromatographically purified over silica gel with $CHCl_3/CH_3OH$ (99/1 to 90/10): Yield 11 g (19%).

c)2-[2-(4-diphenylmethyl-piperazin-1-yl)-ethoxy]-ethylamine

The reaction of the phthalimide to the amine occurs analogously to Example B)d).

Batch size: 27 g (55.6 mmol) 2-{2-[2-(4-diphenylmethyl-piperazinyl)-ethoxy]-ethyl}-isoindol-1,3-dione and 5.4 ml (110 mmol) hydrazine-hydrate.

The purification occurs by chromatography on silica gel with $CHCl_3/CH_3OH/TEA$ (9/1/0 to 9/1/1): Yield 12.4 g (66%).

Example F

4-{4-[bis-(4-fluorophenyl)-methyl]-piperazin-1-yl}-but-2-inylamine a) 2-propinyl-isoindolin-1,3-dione 32.3 g (271 mmol) 3-bromopropine are dissolved in 150 ml DMF and 50.3 g (271 mmol) phthalimide potassium salt are added under ice cooling. The suspension is warmed at 70° C. for eight hours. The mixture is concentrated under a vacuum and the residue is distributed between acetic acid ethyl ester and water. The organic phase is dried over sodium sulfate and the solvent is removed under vacuum. The residue is crystallized from acetic acid ethyl ester: Yield 36.4 g (72%) colorless crystals.

b) 2-(4-{4-[bis-(4-fluorophenyl)-methyl]-piperazin-1-yl}-but-2-inyl)-isoindolin-1,3-dione 15 g (81 mmol) 2-propinyl-isoindolin-1,3-dione, 15 g (52 mmol) [bis-(4-fluorophenyl)-methyl]-piperazine, 2:5 g (81 mmol) paraformaldehyde and 0,2 g copper sulfate are stirred for three hours in 200 ml dioxane at 100° C. The cool solution is concentrated under vacuum and the residue is distributed between acetic acid ethyl ester and saturated NaCl solution. The organic phase is dried over sodium sulfate and concentrated under vacuum until dry. The residue is chromatographically purified over silica gel with acetic acid ethyl ester/petroleum ether (1/1): Yield 23.4 g (93%) yellow amorphous solid.

c) 4-{4-[bis-(4-fluorophenyl)-methyl]-piperazin-1-yl}-but-2-inylamine

The reaction of the phthalimide to the amine occurs analogously to Example 21)d): 23.3 g (48 mmol) 2-(4-{4-[bis-(4-fluorophenyl)-methyl]-piperazin-1-yl}-but-2-inyl)-isoindolin-1,3-dione and 4.7 ml (96 mmol) hydrazine.hydrate. The purification occurs by chromatography on silica gel with $CHCl_3/CH_3OH$ (90/10 to 85/15): Yield 9.8 g (58%).

EXAMPLE G

4-[4-(1,2,3,4-tetrahydronaphthalin-1-yl)-piperazin-1-yl]-butylamine a) 2-{4-[4-(1,2,3,4-tetrahydronaphthalin-1-yl)-piperazin-1-yl]-butyl}-isoindolin-1,3-dione.dihydrochloride 30 g (138,6 mmol) 1-(1,2,3,4-tetrahydronaphthyl)-1-piperazine, 40.3 g (140 mmol) N-(4-bromobutyl)-phthalimide and 27.6 g (200 mmol) potassium carbonate are stirred in 150 ml DMF for three hours at RT. The mixture is concentrated under a vacuum and the residue is distributed between 200 ml acetic acid ethyl ester and 150 ml water. The aqueous phase is extracted 50 ml acetic acid ethyl ester and the combined organic phases are washed four times with water. The organic phase is dried over sodium sulfate and concentrated under vacuum until dry. The residue is dissolved in 400 ml methanol and mixed with 70 ml 6.6M isopropanolic hydrochloric acid. The salt precipitated in the cold is drawn off and dried. Colorless crystals of MP.175–180° C.: Yield-53.2 g (78%).

b) 4-[4-(1,2,3,4-tetrahydronaphthalin-1-yl)-piperazin-1-yl]-butylamine

The reaction of the phthalimide to the amine occurs analogously to Example B)d).

Batch size: 52 g (106 mmol) 2-{4-[4-(1,2,3,4-tetrahydronaphthalin-1-yl)-piperazin-1-yl]-butyl}-isoindolin-1,3-dione-dihydrochloride and 14.6 ml (300 mmol) hydrazine-hydrate in 500 ml ethanol.

The accumulated crude product is further processed without further purification: Yield 27.4 g (89%).

Example H

4-[4-(5,6,7,8-tetrahydro-naphthalin-1-yl)-piperazin-1-yl]-butylamine.trihydrochloride a) 2-{4-[4-(5,6,7,8-tetrahydro-naphthalin-1-yl]-piperazin-1-yl)-butyl}-isoindolin-1,3-dione The reaction of the piperazine with the phthalimide occurs analogously to Example 26a.

Batch size: 24 g (110.9 mmol) 1-(5,6,7,8,-tetrahydronaphthalin-1-yl)-piperazine, 32.6 g (115.4 mmol) N-(4-bromobutyl)-phthalimide and 30.6 g (221.8 mmol) potassium carbonate in 240 ml DMF.

The purification occurs by chromatography over silica gel with $CHCl_3/CH_3OH$ (100/0 to 98/2): Yield 41.6 g (89%).

b) 4-[4-(5,6,7,8-tetrahydronaphthalin-1-yl)-piperazin-1-yl]-butylamine.Trihydrochloride The reaction of the phthalimide to the amine occurs analogously to Example 21d.

Batch size: 41.5 g (99.4 mmol) 2-{4-[4-(5,6,7,8-tetrahydronaphthalin-1-yl)-piperazin-1-yl]-butyl}-isoindolin-1,3-dione and 9.5 ml (198.8 mmol) hydrazine-hydrate in 400 ml ethanol.

The purification occurs by a chromatography over silica gel with $CHCl_3/CH_3OH/NH_4OH$ (90/10/0 to 90/9/1). After removing the solvent the residue is dissolved in 300 ml isopropanol and mixed with 47 ml 6M isopropanolic hydrochloric acid. The salts precipitating in the cold is filtered off and dried: Yield 23.5 g (59%).

Example I

4-[4-(naphthalin-1-yl)-piperazin-1-yl)]-butylamine a) 2-[4-(naphthalin-1-yl-piperazin-1-yl)-butyl]-isoindolin-1,3-dione The reaction of the piperazine with the phthalimide occurs analogously to Example G)a).

Batch size: 21 g (100 mmol) 1-(1-naphthyl)-piperazine [Production according to Glennon et al., J. Med. Chem. 29, 2375 (1986)], 28.3 g (100 mmol) N-(4-bromobutyl)-phthalimide and 20.8 g (150 mmol) potassium carbonate in 250 ml DMF.

The accumulated crude product is further processed without further purification: Yield 30 g (68%).

b) 4-[4-(naphthalin-1-yl)-piperazin-1-yl)]-butylamine

The reaction of phthalimide to the amine occurs analogously to Example B)d).

Batch size: 30 g (68 mmol) 2-[4-(naphthalin-1-yl-piperazin-1-yl)-butyl]-isoindolin-1,3-dione and 6.9 g (137 mmol) hydrazine hydrate in ethanol.

The accumulated crude product is further processed without further purification: Yield 14.6 g (75%).

Example J 11-methanesulfonyloxy-6,11-dihydrodibenzo[b,e]-thiepine a) 6.11-dihydro-dibenzo[b,e]thiepin-11-ol 48 g (212 mmol) 6.1-dihydro-dibenzo[b,e]thiepin-11-one are dissolved in 480 ml absolute methanol and cooled to ca. −10° C. 19.2 g (507 mmol) sodium borohydride is added portion wise to this solution. The mixture is stirred for three hours at RT without further cooling. After the careful addition of 30 ml water, the suspension is concentrated under vacuum. The residue is taken up in 500 ml dichloromethane and washed twice each with 150 ml water. The organic phase is dried over sodium sulfate and the solvent is removed under vacuum. The residue is crystallized from 180 ml toluene. Colorless crystals of MP. 108° C.: Yield 41.2 g (85%).

b) 11-methanesulfonyloxy-6,11-dihydrodibenzo[b,e]-thiepine 3.5 g (15.5 mmol) 6,11-dihydro-dibenzo[b,e]thiepin-11-ole and 2.4 ml (17 mmol) TEA are dissolved in 50 ml absolute dichloromethane. The mixture is cooled to ca. 5° C. and a solution of 1.3 ml (16.3 mmol) methanesulfonyl chloride in 10 ml absolute dichloromethane is added dropwise. The mixture is additionally stirred for two at RT and directly employed in Example 11.

Example K

2-[4-tert-butoxycarbonyl-piperazin-1-yl)-ethylamine a) 2-{2-[4-(tert-butoxycarbonyl)-piperazin-1-yl]-ethyl}-isoindolin-1,3-dione 44.7 g (240 mmol) N-(tert-butoxycarbonyl)-piperazine, 60.9 g (240 mmol) N-(2-bromoethyl)-phthalimide, 49.8 g (360 mmol) potassium carbonate and 49.5 g (330 mmol) sodium iodide are heated in 1000 ml ethyl methyl ketone for five hours under reflux. After cooling the reaction mixture and concentrated under vacuum. The residue is taken up in 700 ml chloroform and extracted twice by shaking each with 50 ml water. The organic phase is dried over sodium sulfate and the solvent is distilled off. The residue is crystallized from 110 ml methanol. Colorless crystals of MP. 136–138° C.: Yield 47.6 g (55%).

b) 2-[4-(tert-butoxycarbonyl)-piperazin-1-yl]-ethylamine

The reaction of the phthalimide to the amine occurs analogously to Example B)d).

Batch size: 42.2 g (120 mmol) 2-{2-[4-(tert-butoxycarbonyl)-piperazin-1-yl]-ethyl}-isoindolin-1,3-dione and 11.6 ml (240 mmol) hydrazine-hydrate in 450 ml ethanol.

The accumulated crude product is further processed without further purification: Yield 24.8 g (90%).

Example L 4-(4-biphenyl-2-yl-piperazin-1-yl)-butylamine a) 2-[4-(4-biphenyl-2-yl-piperazin-1-yl)-butyl]-isoindolin-1,3-dione The reaction of piperazine with the phthalimide occurs analogous to Example G)a).

Batch size: 15.3 g (64.2 mmol) 1-(o-biphenylyl)-piperazine, 18.5 g (64.2 mmol) N-(4-bromobutyl)-phthalimide and 13.3 g (96 mmol) potassium carbonate in 270 ml ethyl methyl ketone. The purification occurs by chromatography over silica gel with $CHCl_3/CH_3OH$ (98/2): Yield 29 g (99%).

b) 4-(4-biphenyl-2-yl-piperazin-1-yl)-butylamine

The reaction of the phthalimide to the amine occurs analogously to Example B)d).

Batch size: 20.8 g (47.3 mol) 2-[4-(4-biphenyl-2-yl-piperazin-1-yl)-butyl]-isoindolin-1,3-dione and 4.6 ml (94.6 mmol) hydrazine-hydrate in 185 ml ethanol.

The accumulated crude product is further processed without further purification: Yield 11.6 g (79%).

Example M

4-[4-(9H-fluoroen-9-yl)-piperazin-1-yl]-butylamine a) 2-{4-[4-(9H-fluoroen-9-yl)-piperazin-1-yl]-butyl}-isoindol-in-1,3-dione The reaction of the piperazine with the phthalimide occurs analogously to Example 26a.

Batch size: 25 g (77.3 mmol) 1-(9-fluoroenyl)-piperazine di-hydrochloride, 22.9 g 181 mmol) N-(4-bromobutyl)-phthalimide and 34 g (246 mmol) potassium carbonate in 80 ml DMF.

The purification occurs by chromatography over silica gel with $CHCl_3/CH_3OH$ (99/1 to 90/10): Yield 30 g (86%).

b) 4-[4-(9H-fluoroen-9-yl)-piperazin-1-yl]-butylamine

The reaction to the phthalimide to the amine occurs analogously to Example 21d.

Batch size: 33 g (76.4 mmol) 2-{4-[4-(9H-fluoroen-9-yl)-piper-azin-1-yl]-butyl}-isoindolin-1,3-dione and 7.4 ml (153 mmol) hydrazine-hydrate in ethanol.

The accumulated crude product is further processed without further purification: Yield 11.5 g (46%).

Example N

4-[4-(10,11-dihydro-5H-dibenzo[a,d]cyclohepten-5-yl)-1-piperazin-1-yl]-butylamine a) 1-(10,11-dihydro-5H-dibenzo[a,d]cyclohepten-5-yl)-piperazine 48 g (210 mmol) 5-chloro-10,11-dihydro-5H-dibenzo[a,d]dicyclo-heptene are dissolved in 500 ml dioxane and after addition of 45 g (522 mmol) piperazine, the mixture is heated under reflux for 7 hours with stirring. After cooling, this is concentrated under vacuum and the residue is distributed between 500 ml chloroform and 300 ml water. The aqueous phase is additionally washed three times each with 200 ml chloroform. The combined organic phases are dried over sodium sulphate and the solvent is removed under vacuum. The residue is chromatographically purified over silica gel with $CHCl_3/CH_3OH$ (98/2 to 90/10): Yield 34.5 g (58%).

b) 2-{4-[4-(10,11-dihydro-5H-dibenzo[a,d] cyclohepten-5-yl)-piperazin-1-yl]-butyl}-isoindolin-1,3-dione The reaction of the piperazine with the phthalimide occurs analogously to Example G)a).

Batch size: 34.5 g (124 mmol) 1-(10,11-dihydro-5H-dibenzo-[a,d]cyclohepten-5-yl)-piperazine, 35 g (124 mmol) N-(4-bromobutyl)-phthalimide and 3.7 g (24.8 mmol) sodium iodide in 80 ml DMF.

The purification occurs by chromatography over silica gel with $CHCl_3/CH_3OH$ (98/2): Yield 55.3 g (93%).

c) 4-[4-(10,11-dihydro-5H-dibenzo[a,d]cyclohepten-5-yl)-1-piperazin-1-yl]-butylamine The reaction of the phthalimide to the amine occurs analogously to Example B)d).

Batch size: 30 g (62.5 mmol) 2-{4-[4-(10,11-dihydro-5H-di-benzo[a,d]cyclohepten-5-yl)-piperazin-1-yl]-butyl}-isoindolin-1,3-dione and 6.2 ml (125 mmol) hydrazine.hydrate in 250 ml ethanol.

The accumulated crude product is further processed without further purification: Yield 12.8 g (58%).

The active ingredients according to the invention can be processed to the desired medicaments in the form of their acid addition salts, hydrates or solvates individually or in combination with each other, optionally under addition of other active ingredients. In the case of the combination of active ingredients according to the invention with other medicinals, these can also optionally be separately present next to each other in the medicine packaging, for example as tablets next to vials, depending on the requirements.

Further subject-matter of the invention is a method for the treatment of the human or animal body in which a compound or compound mixture according to formula (I), wherein the substituents have the above described meanings, is administered for treatment of tumors and/or as a cytostatic agent, cancerostatic agent or as an immunosuppressing agent, optionally in combination with further cytostatic or immunosuppressive active ingredients or other active ingredients suitable for the named indications.

Furthermore, the invention relates to a compound or compound mixture according to formula (I) for use in a therapeutic method in which the therapeutic use is carried out in connection with one or more medical indications with tumors or for immunosuppression, optimally in combination with further pharmaceuticals suitable for the named indications.

The use of one or more compounds according to formula (I), for the production of medicaments for the treatment of the human or animal body, especially in connection with one or more medical indications in the treatment of tumors or for immunosuppression, optimally in combination with further pharmaceuticals suitable in these indications or the use of compounds according to formula (I) in a corresponding diagnosis method also represent an embodiment according to the invention, whereby the compounds for the designated medical indications are included that are excluded from claims 1 and 2 in view of the definition of group G1. The medical indications according to the invention of the compounds excluded from the protective scope of the compound claims are new.

The respective suitable tumor indications are illustrated in the last section of the description in the discussion of the pharmacological test results.

A method for the production of medicaments with an amount of one or more compounds according to formula. (I) which are suitable for the processing of these active ingredients together with respective suitable pharmaceutically acceptable carriers and adjuvants for finished medicinal forms equally belongs to the scope of protection according to the invention.

Depending on the medical indication being considered the respective suitable medicinal form is selected for the suitable therapeutic application, whereby especially 0.001 or 0.01 to 2 mg and/or 0.1, 1, 2, 5, 10, 20, 25, 30, 50, 100, 200, 300, 500, 600, 800, 1000, 2000, 3000, 4000 or 5000 mg of active ingredient according to the claims 1 to 7, 9 and 10 are applied as a dosage and/or dose unit for single administration.

The invention also relates to the use of the compounds according to formula (I) for treatment in the above indications, as well as a diagnostic agent.

The production methods of the respective suitable medicaments as well as a series of examples of medicinal forms are described in the following for better understanding of the invention.

Therapeutic Administration Forms

The production of medicaments with an amount of one or more compounds according to the invention and/or their use in the application according to the invention occurs in the customary manner by means of common pharmaceutical technology methods. For this, the active ingredients as such or in the form of their salts are processed together with suitable, pharmaceutically acceptable adjuvants and carriers to medicinal forms suitable for the various indications and types of application. Thereby, the medicaments can be produced in such a manner that the respective desired release rate is obtained, for example a quick flooding and/or a sustained or depot effect.

Preparations for parenteral use, to which injections and infusions belong, are among the most important systemically employed medicaments for tumor treatment as well as for other indications.

Preferably, injections are administered for the treatment of tumors. These are prepared either in the form of vials or also as so-called ready-to-use injection preparations, for example as ready-to-use syringes or single use syringes in addition to perforation bottles for multiple withdrawals. Administration of the injection preparations can occur in the form of subcutaneous (s.c.), intramuscular (i.m.), intravenous (i.v.) or intracutaneous (i.c.) application. The respective suitable injection forms can especially be produced as solutions, crystal suspensions, nanoparticular or colloid-disperse systems, such as for example, hydrosols.

The injectable formulations can also be produced as concentrates which can be adjusted with aqueous isotonic dilution agents to the desired active ingredient dosage. Furthermore, they can also be produced as powders, such as for example lyophilisates, which are then preferably dissolved or dispersed immediately before application with suitable diluents. The infusions can also be formulated in the form of isotonic solutions, fat emulsions, liposome formulations, microemulsions and liquids based on mixed micells, for example, based on phospholipids. As with injection preparations, infusion formulations can also be prepared in the form of concentrates to dilute. The injectable formulations can also be applied in the form of continuous infusions as in stationary as well as in out-patient therapy, for example in the form of mini-pumps.

Albumin, plasma expanders, surface active compounds, organic solvents, pH influencing compounds, complex forming compounds or polymeric compounds can be added to the parenteral medicinal forms, especially as substances for influencing the adsorption of the active ingredients to protein or polymers or also with the aim of decreasing the adsorption of the active ingredient to materials such as injection instruments or packaging materials, for example plastic or glass.

The active ingredients can be bound to nanoparticles in the preparations for parenteral use, for example on finely dispersed particles based on poly(meth)acrylates, polyacetates, polyglycolates, polyamino acids or polyether urethanes. The parenteral formulations can also be constructively modified as depot preparations, for example on the multiple unit principle, where the active ingredients are incorporated in a most finely distributed and/or dispersed, suspended form or as crystal suspensions, or on the single unit principle, where the active ingredient is enclosed in a medicinal form, for example, a tablet or a seed which is subsequently implanted. Often, these implantations or depot medicaments in single unit and multiple unit medicinal forms consist of so-called biodegradable polymers, such as for example, polyether urethanes of lactic and glycolic acid, polyether urethanes, polyamino acids, poly(meth)acrylates or polysaccharides.

Sterilized water, pH value influencing substances, such as for example organic and inorganic acids or bases as well as their salts, buffer substances for setting the pH value, agents for isotonicity, such as for example sodium chloride, monosodium carbonate, glucose and fructose, tensides and/or surface active substances and emulsifiers, such as for example, partial fatty acid esters of polyoxyethylene sorbitan (Tween®) or for example fatty acid esters of polyoxethylene (Cremophor®), fatty oils such as for example peanut oil, soybean oil and castor oil, synthetic fatty acid esters, such as for example ethyl oleate, isopropyl myristate and neutral oil (Miglyol®) as well as polymer adjuvants such as for example gelatine, dextran, polyvinylpyrrolidone, organic solvent additives which increase solubility, such as for example propylene glycol, ethanol, N,N-dimethylacetamide, propylene glycol or complex forming compounds such as for example citrates and urea, preservatives, such as for example hydroxypropyl benzoate and hydroxymethyl benzoate, benzyl alcohol, anti-oxidants, such as for example sodium sulphite and stabilizers, such as for example EDTA, are suitable as adjuvants and carriers in the production of preparations for parenteral use.

In suspensions, addition of thickening agents to prevent the settling of the active ingredients from tensides and peptizers, to secure the ability of the sediment to be shaken, or complex formers, such as EDTA, ensues. This can also be achieved with the various polymeric agent complexes, for example with polyethylene glycols, polystyrol, carboxymethylcellulose, Pluronics® or polyethylene glycol sorbitan fatty acid esters. The active ingredient can also be incorporated in liquid formulations in the form of inclusion compounds, for example with cyclodextrins. As further adjuvants, dispersion agents are also suitable. For production of lyophilisates, builders are also used, such as for example mannite, dextran, saccharose, human albumin, lactose, PVP or gelatine varieties.

As long as the active ingredients are not incorporated in the liquid medicinal formulations in the form of a base, they are used in the form of their acid addition salts, hydrates or solvates in the preparations for parenteral use.

A further systemic application form of importance is peroral administration as tablets, hard or soft gelatine capsules, coated tablets, powders, pellets, microcapsules, oblong compressives, granules, chewable tablets, lozenges, gums or sachets. These solid peroral administration forms can also be prepared as sustained action and/or depot systems. Among these are medicaments with an amount of one or more micronized active ingredients, diffusions and erosion forms based on matrices, for example by using fats, wax-like and/or polymeric compounds, or so-called reservoir systems. As a retarding agent and/or agent for controlled release, film or matrix forming substances, such as for example ethylcellulose, hydroxypropylmethylcellulose, poly(meth)acrylate derivatives (for example Eudragit®), hydroxypropylmethylcellulose phthalate are suitable in organic solutions as well as in the form of aqueous dispersions. In this connection, so-called bio-adhesive preparations are also to be named in which the increased retention time in the body is achieved by intensive contact with the mucus membranes of the body. An example of a bio-adhesive polymer is the group of Carbomers®.

For sublingual application, compressives, such as for example non-disintegrating tablets in oblong form of a suitable size with a slow release of active ingredient, are especially suitable. For purposes of a targeted release of active ingredients in the various sections of the gastrointestinal tract, mixtures of pellets which release at the various places are employable, for example mixtures of gastric fluid soluble and small intestine soluble and/or gastric fluid resistant and large intestine soluble pellets. The same goal of releasing at various sections of the gastrointestinal tract can also be conceived by suitably produced laminated tablets with a core, whereby the coating of the agent is quickly released in gastric fluid and the core of the agent is slowly released in the small intestine milieu. The goal of controlled release at various sections of the gastrointestinal tract can also be attained by multilayer tablets. The pellet mixtures with differentially released agent can be filled into hard gelatine capsules.

Anti-stick and lubricant and separating agents, dispersion agents such as flame dispersed silicone dioxide, disintegrates, such as various starch types, PVC, cellulose esters as granulating or retarding agents, such as for example wax-like and/or polymeric compounds on the basis of Eudragit®, cellulose or Cremophor® are used as a further adjuvants for the production of compressives, such as for example tablets or hard and soft gelatine capsules as well as coated tablets and granulates.

Anti-oxidants, sweetening agents, such as for example saccharose, xylite or mannite, masking flavors, aromatics, preservatives, colorants, buffer substances, direct tableting agents, such as for example microcrystalline cellulose, starch and starch hydrolysates (for example Celutab®), lactose, polyethylene glycols, polyvinylpyrrolidone and dicalcium phosphate, lubricants, fillers, such as lactose or starch, binding agents in the form of lactose, starch varieties, such as for example wheat or corn and/or rice starch, cellulose derivatives, for example methylcellulose, hydroxypropylcellulose or silica, talcum powder, stearates, such as for example magnesium stearate, aluminium stearate, calcium stearate, talc, siliconized talc, stearic acid, acetyl alcohol or hydrated fats, etc. are also used.

In this connection, oral therapeutic systems constructed especially on osmotic principles, such as for example GIT (gastrointestinal therapeutic system) or OROS (oral osmotic system), are also to be mentioned.

Effervescent tablets or tabsolute both of which represent immediately drinkable instant medicinal forms which are quickly dissolved or suspended in water are among the perorally administrable compressives.

Among the perorally administrable forms are also solutions, for example drops, juices and suspensions, which can be produced according to the above given method, and can still contain preservatives for increasing stability and optionally aromatics for reasons of easier intake, and colorants for better differentiation as well as antioxidants and/or vitamins and sweeteners such as sugar or artificial sweetening agents. This is also true for inspissated juices which are formulated with water before ingestion. Ion exchange resins in combination with one or more active ingredients are also to be mentioned for the production of liquid injestable forms.

A special release form consists in the preparation of so-called floating medicinal forms, for example based on tablets or pellets which develop gas after contact with body fluids and therefore float on the surface of the gastric fluid. Furthermore, so-called electronically controlled release systems can also be formulated by which active ingredient release can be selectively adjusted to individual needs.

A further group of systemic administration and also optionally topically effective medicinal forms are represented by rectally applicable medicaments. Among these are suppositories and enema formulations. The enema formulations can be prepared based on tablets with aqueous solvents for producing this administration form. Rectal capsules can also be made available based on gelatine or other carriers.

Hardened fat, such as for example Witepsol®, Massa Estarinum®, Novata®, coconut fat, glycerol-gelatine masses, glycerol soap-gels and polyethylene glycols are suitable as suppository bases.

For long-term application with a systematic active ingredient release up to several weeks, pressed implants are suitable which are preferably formulated on the basis of so-called biodegradable polymers.

As a further important group of systemically active medicaments, transdermal systems are also to be emphasized which distinguish themselves, as with the above-mentioned rectal forms, by circumventing the liver circulation system and/or liver metabolism. These plasters can be especially prepared as transdermal systems which are capable of releasing the active ingredient in a controlled manner over longer or shorter time periods based on different layers and/or mixtures of suitable adjuvants and carriers. Aside from suitable adjuvants and carriers such as solvents and polymeric components, for example based on Eudragit®, membrane infiltration increasing substances and/or permeation promoters, such as for example oleic acid, Azone®, adipinic acid derivatives, ethanol, urea, propylglycol are suitable in the production of transdermal systems of this type for the purpose of improved and/or accelerated penetration.

As topically, locally or regionally administration medicaments, the following are suitable as special formulations-vaginally or genitally applicable emulsions, creams, foam tablets, depot implants, ovular or transurethral administration instillation solutions. For opthalmological application, highly sterile eye ointments, solutions and/or drops or creams and emulsions are suitable.

In the same manner, corresponding otological drops, ointments or creams can be designated for application to the ear. For both of the above-mentioned applications, the administration of semi-solid formulations, such as for example gels based on Carbopols® or other polymer compounds such as for example polyvinylpyrolidone and cellulose derivatives is also possible.

For customary application to the skin or also to the mucus membrane, normal emulsions, gels, ointments, creams or mixed phase and/or amphiphilic emulsion systems (oil/water-water/oil mixed phase) as well as liposomes and transfersomes can be named. Sodium algenate as a gel builder for production of a suitable foundation or cellulose derivatives, such as for example guar or xanthene gum, inorganic gel builders, such as for example aluminium hydroxides or bentonites (so-called thixotropic gel builder), polyacrylic acid derivatives, such as for example Carbopol®, polyvinylpyrolidone, microcrystalline cellulose or carboxymethylcellulose are suitable as adjuvants and/or carriers. Furthermore, amphiphilic low and high molecular weight compounds as well as phospholipids are suitable. The gels can be present either as hydrogels based on water or as hydrophobic organogels, for example based on mixtures of low and high molecular paraffin hydrocarbons and Vaseline.

Anionic, cationic or neutral tensides can be employed as emulsifiers, for example alkalized soaps, methyl soaps, amine soaps, sulfonated compounds, cationic soaps, high fatty alcohols, partial fatty acid esters of sorbitan and polyoxyethylene sorbitan, for example lanette types, wool wax, lanolin; or other synthetic products for the production of oil/water and/or water/oil emulsions.

Hydrophilic organogels can be formulated, for example, on the basis of high molecular polyethylene glycols. These gel-like forms are washable. Vaseline, natural or synthetic waxes, fatty acids, fatty alcohols, fatty acid esters, for example as mono-, di-, or triglycerides, paraffin oil or vegetable oils, hardened castor oil or coconut oil, pig fat, synthetic fats, for example based on acrylic, caprinic, lauric and stearic acid, such as for example Softisan® or triglyceride mixtures such as Miglyol® are employed as lipids in the form of fat and/or oil and/or wax-like components for the production of ointments, creams or emulsions.

Osmotically effective acids and bases, such as for example hydrochloric acid, citric acid, sodium hydroxide solution, potassium hydroxide solution, monosodium carbonate, further buffer systems, such as for example citrate, phosphate, tries-buffer or triethanolamine are used for adjusting the pH value.

Preservatives, for example such as methyl- or propyl benzoate (parabenes) or sorbic acid can be added for increasing stability.

Pastes, powders or solutions are to be mentioned as further topically applicable forms. Pastes often contain lipophilic and hydrophilic auxiliary agents with very high amounts of fatty matter as a consistency-giving base.

Powders or topically applicable powders can contain for example starch varieties such as wheat or rice starch, flame dispersed silicon dioxide or silica, which also serve as diluents, for increasing flowability as well as lubricity as well as for preventing agglomerates.

Nose drops or nose sprays serve as nasal application forms. In this connection, nebulizers or nose creams or ointments can come to use.

Furthermore, nose spray or dry powder formulations as well as controlled dosage aerosols are also suitable for systemic administration of the active ingredients.

These pressure and/or controlled dosage aerosols and dry powder formulations can be inhaled and/or insufflated. Administration forms of this type also certainly have importance for direct, regional application in the lung or bronchi and larynx. Thereby, the dry powder compositions can be formulated for example as active ingredient-soft pellets, as an active ingredient-pellet mixture with suitable carriers, such as for example lactose and/or glucose. For inhalation or insufflation, common applicators are suitable which are suitable for the treatment of the nose, mouth and/or pharynx. The active ingredients can also be applied by means of an ultrasonic nebulizing device. As a propellant gas for aerosol spray formulations and/or controlled dosage aerosols, tetrafluoroethane or HFC 134a and –or heptafluoropropane or HFC 227 are suitable, wherein non-fluorinated hydrocarbons or other propellants which are gaseous at normal pressure and room temperature, such as for example propane, butane or dimethyl ether can be preferred. Instead of controlled dosage aerosols, propellant-free, manual pump systems can also be used.

The propellant gas aerosols can also suitably contain surface active adjuvants, such as for example isopropyl myristate, a polyoxyethylene sorbitan fatty acid ester, sorbitan trioleate, lecithins or soya lecithin.

For regional application in situ, solutions for instillation, for example for transurethral administration in bladder tumors or genital tumors, or for profusion in liver tumors or other organ carcinomas are suitable.

The respective suitable medicinal forms can be produced in accordance with the prescription and procedures based on pharmaceutical-physical fundamentals as they are described for example in the following handbooks and are included in the present inventive subject-matter with respect to the production of the respective suitable medicaments:

Physical Pharmacy (A. N. Martin, J. Swarbrick, A. Cammarata), 2nd Ed., Philadelphia Pa., (1970), German version: Physikalische Pharmazie, (1987), 3rd edition, Stuttgart;

R. Voigt, M. Bornschein, Lehrbuch der pharmazeutischen Technologie, Verlag Chemie, Weinheim, (1984), 5th edition;

P. H. List, Arzneimformenlehre, Wissenschaftliche Verlagsgesellschaft mbH, Stuttgart, (1985), 4th edition;

H. Sucker, P. Fuchs, P. Speiser, Pharmazeutische Technologie, Georg Thieme Verlag, Stuttgart-New York, (1991), 2nd edition;

A. T. Florence, D. Attwood, Physicochemical Principles of Pharmacy, The Maximillan Press Ltd., Hong Kong, (1981);

L. A. Trissel, Handbook on Injectable Drugs, American Society of Hospital Pharmacists, (1994), 8th edition;

Y. W. Chien, Transdermal Controlled Systemic Medications, Marcel Dekker Inc., New York-Basel, (1987);

K. E. Avis, L. Lachmann, H. A. Liebermann, Pharmaceutical Dosage Forms: Parenteral Medications, volume 2, Marcel Dekker Inc., New York-Basel, (1986);

B. W. Müller, Controllen Drug Delivery, Paperback APV, volume 17, Wissenschaftliche Verlagsgesellschaft mbH, Stuttgart, (1987);

H. Asch, D. acetic P. C. Schmidt, Technologie von Salben, Suspensionen and Emulsionen, Wissenschaftliche Verlagsgesellschaft mbH, Stuttgart, (1984);

H. A. Liebermann, L. Lachman, J. B. Schwartz, Pharmaceutical Desage forms: Tablets, Volume 1, Marcel Dekker Inc., New York, 2nd Edition (1989);

D. Chulin, M. Deleuil, Y. Pourcelot, Powder Technology and Pharmaceutical Processes, in J. C. Williams, T. Allen, Handbook of Powder Technology, Elsevier Amsterdam-London-New York-Tokyo, (1994);

J. T. Carstensen, Pharmaceutical Principles of Solid Dosage Forms, Technomic Publishing Co., Inc., Lancaster-Basel, (1993).

Production Examples

1. Injection therapeutics a) Parenteral Solution

| | |
|---|---:|
| active ingredient used according to the invention | 5.000 g |
| acid sodium phosphate | 5.000 g |
| sodium tartrate | 12.000 g |
| benzyl alcohol | 7.500 g |
| water for injection purposes | to 1000.000 ml |

The solution is produced according to the customary method, sterilized and filled into 10 ml vials. One vial contains 50 mg of the compound according to the invention.

b) Parenteral Solution

| | |
|---|---:|
| active ingredient used according to the invention | 1.000 g |
| hydrochloric acid, dilute | 5.000 g |
| sodium chloride | 6.000 g |
| water for injection purposes | to 1000.000 ml |

The solution is produced according to a customary method by stirring; the medicinal form is adjusted to a suitable pH value by acid addition and subsequently filled into 100 ml vials and sterilized. A vial contains 100 mg of the compound according to the invention.

c) Parenteral Dispersion

| | |
|---|---:|
| active ingredient used according to the invention | 10.000 g |
| soya lecithin | 20.000 g |
| saturated triglycerides | 100.000 g |
| sodium hydroxide | 7.650 g |
| water for injection purposes | to 1000.000 ml |

The active ingredient(s) used according to the invention is dispersed in the saturated triglycerides. Then the soya lecithin is added under stirring, and subsequent to this, the aqueous solution of sodium hydroxide is added with subsequent homogenization. The dispersion is sterilized and filled into 10 ml vials. A vial contains 50 mg of the compound according to the invention.

d) Biodegradable Parenteral Depot Medicinal Form

| | |
|---|---:|
| active ingredient used according to the invention | 10.000 g |
| polylactic acid/polygylcolic acid polymer | 70.000 g |
| polyvinylpyrrolidone | 0.200 g |

-continued

| | |
|---|---|
| gelatine | 2.000 g |
| soya lecithin | 2.000 g |
| isotonic sodium chloride solution | to 1000.000 ml |

First, the active ingredient is incorporated into the biodegradable polymer comprising polylactic acid and polyglycolic acid by a suitable method (spray drying, solvent-evaporation or phase separation) and subsequently subjected to a sterilization process. The particles are introduced into a 2-chamber ready-made syringe in which the adjuvant solution, which is also produced in a sterile manner, is filled. The biodegradable microparticles are mixed with the dispersion agent shortly before application and dispersed. A ready-made syringe contains 200 mg of the active compound according to the invention.

e) Parenteral Dispersion for Subcutaneous Instillation

| | |
|---|---|
| active ingredient used according to the invention | 25,000 g |
| soya lecithin | 25,000 g |
| arachis oil | 400,000 g |
| benzyl alcohol | 50,000 g |
| Miglyole ® | to 1000,000 g |

The active ingredient is dispersed together with soya lecithin and arachis oil. The benzyl alcohol is dissolved in Miglyole® and added to the dispersion. The entire dispersion is sterilized and subsequently filled into vials with 2 ml content. A vial contains 50 mg active ingredient.

f) Parenteral Perfusions Solution

The solution named under example b) can also be used for perfusion of liver for example.

According to need, instead of ampules with injection solution, so-called perforation bottles (vials), which can also be optionally preserved, and infusion solutions with an amount of one or more active ingredients according to the invention can also be made available in the customary manner under addition of buffer substances for adjustment of physiological pH value and/or the isotonicity and/or a best possible suitable pH value for the medicinal form (euhydria) and optional further required nutrients, vitamins, amino acids, stablizers and other necessary adjuvants, possibly in combination with further medicinal agents suitable for the mentioned indications.

2. Solid, Peroral Administrable Medicaments a) Tablets

| | |
|---|---|
| active ingredient used according to the invention | 10.000 g |
| lactose | 5.200 g |
| starch, soluble | 1.800 g |
| hydroxypropylmethylcellulose | 900 g |
| magnesium stearate | 100 g |

The above components are mixed with each other and compacted in a conventional manner, wherein a tablet weight of 180 mg is set. Each tablet contains 100 mg active ingredient. If desired, the tablets obtained in this manner are coated, provided with a film coat and/or enterically coated.

b) Coated Tablet Core

| | |
|---|---|
| active ingredient used according to the invention | 10.000 g |
| flame dispersed silicon dioxide | 500 g |
| corn starch | 2.250 g |
| stearic acid | 350 g |
| ethanol | 3.0 l |
| gelatine | 900 g |
| purified water | 10.0 l |
| talcum | 300 g |
| magnesium stearate | 180 g |

From these components, a granulate is produced which is pressed to the desired coated tablet cores. Each core contains 50 mg of active ingredient. The core can be further processed in a customary manner to coated tablets. If desired, a gastric fluid resistant or retarding film coat can be applied in a known manner.

c) Vials for Drinking

| | |
|---|---|
| active ingredient used according to the invention | 0.050 g |
| glycerine | 0.500 g |
| sorbite, 70% solution | 0.500 g |
| sodium saccharinate | 0.010 g |
| methyl-p-hydroxybenzoate | 0.040 g |
| aromatic agent | q.s. |
| sterile water | q.s. to 5 ml |

The above-mentioned components are mixed in a customary manner to a suspension and filled in a suitable drink vial having 5 ml content.

d) Poorly Soluble Sublingual Tablets

| | |
|---|---|
| active ingredient used according to the invention | 0.030 g |
| lactose | 0.100 g |
| stearic acid | 0.004 g |
| talcum purum | 0.015 g |
| sweetener | q.s. |
| aromatic agent | q.s. |
| rice starch | q.s. to 0.500 g |

The active ingredient is compacted together with the adjuvants under high pressure to sublingual tablets, favourably in oblong form.

e) Soft Gel Capsule

| | |
|---|---|
| active ingredient used according to the invention | 0.050 g |
| fatty acid glyceride mixture (Miglyole ®) | q.s. to 0.500 g |

The active ingredient is impasted together with the fluid carrier mixture and mixed together with further adjuvants suitable for the encapsulation and filled into elastic soft gelatine capsules which are sealed.

f) Hard Gelatine Capsules

| | |
|---|---|
| active ingredient used according to the invention | 0.150 g |
| microcrystalline cellulose | 0.100 g |

| | |
|---|---|
| -continued | |
| hydroxypropylmethylcellulose | 0.030 g |
| mannite | 0.100 g |
| ethylcellulose | 0.050 g |
| triethyl citrate | 0.010 g |

The active ingredient is mixed together with the adjuvants, microcrystalline cellulose, hydroxypropylmethylcellulose and mannite, wet with granulation liquid and formed into pellets. These are subsequently coated with a solution of ethylcellulose and triethyl citrate in organic solvents in a fluidized-bed apparatus. A hard gelatine capsule contains 150 mg of active ingredient.

3. Topically Administrable Medicinal Forms a) Hydrophilic Ointment

| | |
|---|---|
| active ingredient used according to the invention | 0.500 g |
| Eucerinum ® anhydricum | 60.000 g |
| microcrystalline wax | 15.000 g |
| Vaseline oil | q.s. to 100.000 g |

The above-mentioned adjuvants are melted and further processed together with the active ingredient to an ointment in a customary manner.

b) Lipophilic Ointment

| | |
|---|---|
| active ingredient used according to the invention | 10.000 g |
| propylene glycol | 50.000 g |
| paraffin, liquid | 100.000 g |
| paraffin wax | 100.000 g |
| Vaseline | to 1000.000 ml |

The active ingredient(s) used according to the invention is dissolved in propylene glycol at ca. 60° C. At the same time, the lipophilic components are melted at 60–70° C. and subsequently combined with the active ingredient solution. The ointment is emulsified at first at 60–70° C. and subsequently cooled to 35–40° C. under constant emulsification and then filled in 10 g tubes. A tube contains 100 mg of the compound according to the invention.

4. Inhalation Therapeutic Agent

Further subject-matter is a pharmaceutical formulation which is characterized in that it contains an active ingredient (s) used according to the invention as a base or a physiologically acceptable salt thereof together with carriers and/or diluents customary for this and suitable for administration by means of inhalation.

In connection with the production of the medicaments, particularly suitable physiologically acceptable salts of the active ingredients are, as already illustrated in the synthesis section, acid addition salts derived from inorganic or organic acids such as for example especially hydrochloride, hydrobromide, sulfate, phosphate, maleate, tartrate, citrate, benzoate, 4-methoxybenzoate, 2- or 4-hydroxybenzoate, 4-chlorobenzoate, p-tosylate, methane sulfonate, ascorbate, salicylate, acetate, formate, succinate, lactate, glutarate, gluconate or tricarballylate.

The administration of the active ingredient(s) used of the invention by means of inhalation occurs according to the invention in conventional ways customary for administrations of this form, for example in the form of a commercial controlled dosage aerosol or in combination with a spacer in controlled dosage aerosols, a metering valve is delivered with whose help, a dosed amount of the composition is administered. For spraying, the present compositions can be formulated for example as aqueous solutions or suspensions and be administered by means of an atomizer. Aerosol spray formulations in which the active ingredient is either suspended with one or two stabilizers in a propellant as a carrier and/or diluent, for example tetrafluoroethane or HFC 134a and/or heptafluoropropane or HFC 227 can equally be used, whereby however, non-fluorinated hydrocarbons or other propellants which are gaseous at normal pressure and room temperature, such as propane, butane or dimethyl ether, can be preferred. Thereby, propellant-free manual pump systems or dry powder systems as described below can also be used.

Suitably, the propellant aerosols can also contain surface active adjuvants, such as for example isopropyl myristate, polyoxyethylene sorbitan fatty acid ester, sorbitan trioleate, lecithins, oleic acid.

For administration by means of inhalation and/or insufflation, the medicaments with an amount of compounds according to the invention can also be formulated in the form of dry powder compositions, for example as active ingredient—soft pellets or as an active ingredient-powder mixture with a suitable carrier, such as for example lactose and/or glucose. The powder compositions can be formulated and administered as single doses or as multiple doses.

The compounds according to the invention are preferably administered by means of a controlled dosage aerosol or in the form of a dry powder dosage formulation, wherein the latter preferably contains glucose and/or lactose as a carrier substance.

As applicators for inhalation of the pharmaceutical formulations containing one or more of the active ingredients used according co the invention, all applicators are generally suitable which are suitable for controlled dosage aerosols and/or a dry powder dosage formulation, such as for example usual applicators for the nose, mouth and or pharynx, or also devices standing under propellant gas for the delivery of a spray (as controlled dosage aerosol or dry powder dosage formulation) as they are also used for inhalations in the nose, mouth and/or pharynx.

A further embodiment can also consist of an aqueous solution of the active ingredient(s) used according to the invention, which also optionally contains further active ingredients and/or additives, which are applied by means of an ultrasound atomizer.

a) Controlled Dosage Aerosol

| | Intended dose per stroke | per aerosol % by weight |
|---|---|---|
| active ingredient used according to the invention | 0.500 mg | 0.66 |
| stabilizer | 0.075 mg | 0.10 |
| HFC 134a | 75.500 mg | 99.24 | b) Controlled Dosage Aerosol

|  | Intended dose per stroke | per aerosol % by weight |
|---|---|---|
| active ingredient used according to the invention | 0.250 mg | 0.32 |
| Stabilizer | 0.038 mg | 0.05 |
| HFC 227 | 79.180 mg | 99.63 |

In the examples a) and b) the micronized active ingredient is, after previous dispersion in a small amount of the stabilizer, placed in a suspension vessel in which the bulk amount of propellant gas solution is found. The corresponding suspension is dispersed by means of a suitable stirring system (for example high performance mixer or ultrasound mixer) until an ultra-fine dispersion results. The suspension is then continuously held in flux in a filling apparatus suitable for cold propellants or pressure fillings.

Alternatively, the suspension can also be produced in a suitable cooled stabilizer solution in HFC 134a/227.

The examples c) to d) describe the composition and production of dosage dry powder formulations.

c) Dosage-Dry Powder Formulation

|  | mg/dose |
|---|---|
| active ingredient used according to the invention | 0.500 mg | d) Dosage-Dry Powder Formulation

|  | mg/dose |
|---|---|
| active ingredient used according to the invention | 0.500 mg |
| lactose Ph.Eur. | to 2.5 mg or to 5.0 mg | e) Dosage-Dry Powder Formulation

|  | mg/dose |
|---|---|
| active ingredient used according to the invention | 0.250 mg |
| lactose Ph.Eur. | to 2.5 mg or to 5.0 mg |

In example c) the active ingredient is formulated after micronization under addition of steam as pellets with an MMAD between 0.1 and 0,3 mm diameter and brought to use in a multi-dose powder applicator.

In the examples d) and e) the active ingredient is micronized, thereafter, bulk material is mixed with the lactose in the given amounts, and subsequently, filled in a multi-dose powder inhalator.

In all of the examples set forth above, the active ingredient or the medicinal agent in the form of the respective suitable pharmaceutical acceptable salt and/or acid addition salts can be present, insofar as the base is not preferred in each case.

Pharmaceutical Experimental Section

1. Growth Inhibition of Human Tumor Cells

The tumor growth inhibiting activity of the substances was determined on human tumor cells in standardized in vitro test systems. In the screening tests, the substances gave $IC_{50}$-values in a concentration range of 0.1 nM to 10 μM.

Example 1

HepG2 cells derived from a human liver carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each.

Three days after the beginning of treatment, the medium was again renewed with the test compounds. After six days of substance incubation, the test was ended and the protein amount in the individual wells was determined with the sulforhodamin-B-method (according to P. Skehan et al.: New Colorimetric Cytoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curve and given as a comparative measurement for the activity of the test compounds.

The results obtained are depicted in the following Table:

| Test substance No. | $IC_{50}$-value [μM] |
|---|---|
| 29 | 0.6 |
| 31 | 0.8 |
| 32 | 0.5 |
| 37 | 0.5 |
| 47 | 1 |
| 158 | 0.2 |
| 208 | 0.3 |
| 227 | 0.6 |

Example 2

A549 cells derived from a human lung carcinoma plated at a density of 20,000 cells/ml in 12-well plastic dishes. Cultivation occurred in Richters IMEM-ZO nutrient medium with 5% fetal calf serum (FCS) in a tissue culture incubator with a gas mixture of 5% $CO_2$ and 95% air at a temperature of 37° C. One day after opening, the culture medium was aspirated from the cells and replaced by fresh medium which contained the respective concentrations of the test substances. For the individual concentrations and the controls without test substances, three fold batches were done for each. Three days after the beginning of treatment, the medium was again renewed with the test compounds.

After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [$\mu$M] |
|---|---|
| 32 | 0.5 |
| 60 | 2 |
| 87 | 0.5 |
| 94 | 2 |
| 101 | 0.4 |
| 138 | 4 |
| 215 | 5 |
| 234 | 0.1 |

Example 3

HT-29 cells derived from a human colon carcinoma plated at a density of 20,000 cells/ml in 12-well plastic dishes. Cultivation occurred in Richters IMEM-ZO nutrient medium with 5% foetal calf serum (FCS) in a tissue culture incubator with a gas mixture of 5% $CO_2$ and 95% air at a temperature of 37° C. One day after plating, the culture medium was aspirated from the cells and replaced by fresh medium which contained the respective concentrations of the test substances. For the individual concentrations and the controls without test substances, three-fold batches were done for each. Three days after the beginning of treatment, the medium was again renewed with the test compounds. After four days of substance incubation, the test was ended and the protein amount in the individual wells was determined with the sulforhodamin-B-method (according to P. Skehan et al.: New Colorimetric Cytotoxicity Assay for Anticancer-Drug Screening. J. Natl. Cancer Inst. 82: 1107–1112, 1990). The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [$\mu$M] |
|---|---|
| 30 | 0.7 |
| 35 | 3 |
| 38 | 0.4 |
| 97 | 0.1 |
| 119 | 0.2 |

Example 4

THP-1 cells derived from a human monocytic leukemia plated at a density of 200,000 cells/ml in 96-well plastic dishes. Cultivation occurred in RPMI 1640 nutrient medium with 10% foetal calf serum (FCS) in a tissue culture incubator with a gas mixture of 5% $CO_2$ and 95% air at a temperature of 37° C. For the individual concentrations and the controls without test substances as well as for the background with nutrient medium but without cells, three-fold batches were done for each. After four days of substance incubation 20 $\mu$l WST-1 reagent (Boehringer Mannheim) was respectfully pipetted in each individual well. After 30 to 60 minute incubation in the tissue culture incubator at 37° C. and 5% $CO_2$, the light extinction was measured in an ELISA reader at 450 nm wave length. The backgrounds were each subtracted from the typical measured valves. (The $IC_{50}$-values (defined as that concentration in which the cell growth was inhibited by 50%) was taken from the dose-response curves and given as a comparative measurement for the activity of the test compounds.

The following results were obtained:

| Test substance No. | $IC_{50}$-value [$\mu$M] |
|---|---|
| 68 | 0.01 |
| 87 | 0.02 |
| 101 | 0.3 |
| 119 | 0.02 |

2. Indications

The compounds of formula (I) and their salts permit a therapeutic use in malignant illnesses of humans and animals through their excellent inhibition of the growth of tumor cells. The anti-neoplastic activity of the described substances can be used for prophylactic, adjunct, palliative, and curative treatment of solid tumors, leukemic illnesses and lymphomas as well as for decreasing or preventing metastasis formation in humans and animals. The therapeutic use is possible in the following illnesses for example: gynaecological tumors, ovarian carcinomas, testicle tumors, prostate carcinomas, skin cancer, kidney cancer, bladder tumors, oesophagus carcinomas, stomach cancer, rectal carcinomas, pancreas carcinomas, thyroid cancer, adrenal tumors, leukemia and lymphomas, Hodgkin's disease, tumor illnesses of the CNS, soft-tissue sarcomas, bone sarcomas, benign and malignant mesotheliomas, but especially intestine cancer, liver cancer, breast cancer, bronchial and lung carcinomas, melanomas, acute and chronic leukemias. Benign papillomatosis tumors can also be limited in their growth with the named substances. The broad effectiveness of the new compounds were tested for example in very different human tumor cells in vitro according to the methods described in point 1. Thereby, the following $IC_{50}$ valves were obtained for the compound Nr. 119:

| Cell line | Source | $IC_{50}$-values [mM] |
|---|---|---|
| HT-29 | colon carcinoma | 0.2 |
| A549 | lung carcinoma | 0.2 |
| HepG2 | hepatocelluar carcinoma | 0.08 |
| THP-1 | monocytic leukemia | 0.02 |

The novelty of the compounds can be expected to have an independent activity profile in the effectiveness against the various tumor types. Thus, tumors which are resistant to customary cytostatic agents, for example, can respond entirely to these substances. In addition, based on the independent characteristics, combinations of the new compounds with known pharmaceuticals used in chemotherapy are promising as long as their properties are complimented in a suitable manner. The integration of the new structures in a therapy scheme could be successful with one or more substances from the following classes for example: anti-metabolites (for example cytarabine, 5-fluorouracil, 6-mercaptopurine, methotrexate), alkylating agents (for example busulfane, carmustine, cisplatin, carboplatin, cyclophosphamide, dacarbazine, melphalane, thiotepa), DNA-intercalating substances and topoisomerase inhibitors (for example actinomycin D, daunorubicin, doxorubicin, mitomycin C, mitoxantrone, etoposide, teniposide, topotecane, irinotecane), spindle poisons (for example vincristine, navelbine, taxol, taxoter), hormonally active agents (for example tamoxifene, flutamide, formestane, gosereline) or other cytostatic agents with complex modes of action (for example L-asparaginase, bleomycin, hydroxyurea). Resistant tumor cells can be made sensitive again for example by interaction of the new compounds with a mechanism of resistance for common cytostatic agents (for example P-glycoprotein, MRP, glutathione-s-transferase, metallothionein).

3. Immuno Suppressing Activity

Many anti-tumor agents have not only a cytotoxic effect on tumor cells, but also on the blood cell system. This leads to a weakening of the immune defence, which can, in turn, be specifically employed to suppress the rejection reaction after an organ transplantation for example. Also use of the main compounds, optionally in combination with other immunological diseases (for example, psoriasis or autoimmune diseases) seems likely. In order to test the possibility for a therapeutic use in illnesses of this type, the substance activity was tested on freshly isolated lymphocytes as follows:

The spleen of a Swiss mouse served as a lymphocyte source. The lymphocyte population was isolated from the spleen cell suspension over a ficoll gradient and taken up in IMEM-ZO culture medium with 0.1% dextran 70,000 and 2% foetal calf serum. The cells were plated at a density of ca. 500,000 cells/well/ml in a 12-well plate, 1 ml doubly concentrated test substance solution was pipetted per well and this was subsequently incubated in a tissue culture incubator at 37° C. and 5% $CO_2$. After 2 days, a 1 ml-aliquot with 5 µl of the fluorescent dye solutions propidium iodide (8 mg/ml) and 3,3'-dihexyloxacarbocyanin iodide (40 µg/ml) each was added per well, and incubated for 3 minutes at room temperature. Subsequently, 10,000 cells per each sample were measured on a flow-through cytometer and the percentage amount of vital cells in the population was determined. By means of the dose-response curves, $IC_{50}$-values were calculated which were also employed in the following Tables for the characterization of the individual substances:

| Test Substance No. | $IC_{50}$ value [µM] |
|---|---|
| 87 | 0.09 |
| 101 | 0.07 |
| 119 | 0.03 |

The independent structural class of the compounds can also be expected to be successful for an efficient combination with known immunosuppressive agents such as for example cyclosporin A, tacrolimus, rapamycin, azathioprine and glucocorticoids.

What is claimed is:

1. Pyridylalkane, pyridylalkene and pyridylalkine carboxamindes of formula (I)

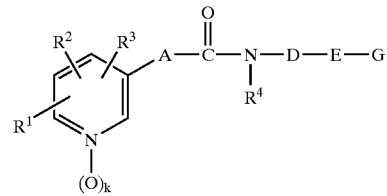

wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a substituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;
a substituted $C_4$–$C_{10}$-alkenylene which is substituted once or twice by $C_1$–$C_6$-alkyl, hydroxy, or $C_1$–$C_6$-alkoxy;
$C_4$–$C_{10}$-alkinylene;
a substituted $C_4$–$C_1$-alkinylene which is substituted once or twice by $C_1$–$C_6$-alkyl, hydroxy, or $C_1$–$C_6$-alkoxy; and
$C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;
E is

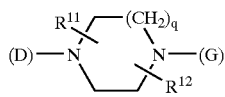

wherein
q is 1;
$R^{11}$ is selected from the group consisting of hydrogen $C_1$–$C_6$-alkyl, hydroxy, hydroxymethyl, carboxy, or $C_2$–$C_7$-alkoxycarbonyl;
$R^{12}$ is selected from the group consisting of hydrogen, $C_1$–$C_6$-alkyl and an oxo group adjacent to a nitrogen atom;
and wherein $R^{11}$ and $R^{12}$ may together form a $C_1$–$C_3$-alkylene bridge under formation of a bicyclic ring system;
G is G1, wherein
$G^1$ is —$(CH_2)_r$—$(CR^{14}R^{15})_s$—$R^{13}$
r is 0, 1, 2 or 3;
s is 0 or 1;
$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;
saturated or unsaturated four to eight-membered heterocycles which contain one or two hetero-atoms selected from the group consisting of N, S and O;
benzyl, phenyl;
monocyclic aromatic five or six-membered heterocycles which contain one to three hetero-atoms selected from the group consisting of N, S and O where the heterocycles are either bound directly or over a methylene group;
anellated bi- and tricyclic aromatic or partially hydrogenated carbocyclic ring systems with 8 to 16 ring atoms and at least one aromatic ring, wherein the linkage may occur either over an aromatic or a hydrogenated ring and either directly or over a methylene group;
anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage may occur either over an aromatic ring or a hydrogenated ring and either directly or over a methylene group;
$R^{14}$ has the same meaning as $R^{13}$, but is selected independently thereof;
$R^{15}$ is selected from the group consisting of hydrogen, hydroxy, methyl, benzyl, and phenyl;
monocyclic aromatic five or six-member heterocycles, which contain one to three hetero-atoms selected from the group consisting of N, S and O and wherein the heterocycles are either bound directly or over a methylene group;
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;
anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrogenated ring and either directly or over a methylene group;
wherein G is not —$(CH_2)_r$—$(CR^{14}R^{15})_s$—$R^{13}$ when
$R^{13}$ represents pyridyl or phenyl, which may be substituted by halogen, alkyl, alkoxy or trifluoromethyl;
$R^{14}$ represents hydrogen or phenyl, which may be substituted by halogen, alkyl, alkoxy or trifluoromethyl;
$R^{15}$ represents hydrogen;
A represents alkylene, substituted ethenylene or butadienylene;
D represents alkylene or alkenylene;
E represents piperazine or homopiperazine; and
S is 1;
wherein G is not phenyl, N-containing heteroaryl, —$CH_2)_{0-2}$—$CH_2$—$C_6H_5$, —$(CH_2)_{0-2}$—$CH_2$—$C_5H_5N$;

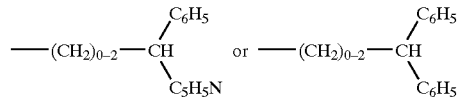

wherein the phenyl group or moiety may be substituted by one or two members selected from the group consisting of halogen, a $C_1$–$C_6$ alkyl, trifluoromethyl and a $C_1$–$C_6$ alkoxy, when
$R^1$ is hydrogen, a halogen, a $C_1$–$C_6$-alkyl, a $C_1$–$C_6$-alkoxy, a $C_1$–$C_6$-alkylthio, a $C_3$–$C_8$-cycloalkyloxy, a $C_3$–$C_8$-cycloalkylthio, a $C_2$–$C_7$-alkoxycarbonyl, carboxy, a phenyl, a phenoxy, a phenylthio, 3-pyridyloxy or 3-pyridylthio;
$R^2$ is hydrogen, a hydroxy, a $C_1$–$C_7$-alkanoyloxy or a $C_2$–$C_7$-alkoxycarbonyloxy, or when $R^1$ and $R_2$ are adjacent to each other, they may combine to form tetramethylene or —$CH_2OCR^{8a}R^{9a}O$—, wherein $R^{8a}$ and $R^{9a}$ are the same or different and are each a $C_1$–$C_6$-alkyl;
$R^3$ is hydrogen, a $C_1$–$C_6$-alkyl or a hydroxy-$C_1$–$C_6$-alkyl;
A is a $C_1$–$C_6$-alkylene or —$(CR^{6a}$=$CR^{7a})ra$-, wherein $R^{6a}$ is hydrogen, a $C_1$–$C_6$-alkyl or a phenyl, $R^{7a}$ is hydrogen, a $C_1$–$C_6$-alkyl, cyano or a phenyl, and ra is 1 or 2;
$R^4$ is hydrogen;
D is a $C_1$–$C_{10}$-alkylene or a $C_4$–$C_{10}$-alkylene interrupted by at least one double bond; and
E is selected from the group consisting of piperazine, piperazine, which is substituted by $C_1$–$C_6$-alkyl, homopiperazine, and homopiperazine, which is substituted by $C_1$–$C_6$-alkyl.

2. A compound according to formula (I)

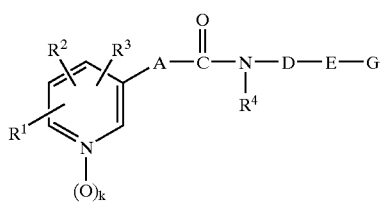

wherein
R¹ is selected from the group consisting of hydrogen, halogen, cyano, $C_1$–$C_6$-alkyl, trifluoromethyl, $C_3$–$C_8$-cycloalkyl, $C_1$–$C_6$-hydroxyalkyl, hydroxy, $C_1$–$C_4$-alkoxy, benzyloxy, $C_1$–$C_4$-alkylthio, $C_1$–$C_5$-alkanoyloxy, $C_1$–$C_4$-alkylthio, $C_2$–$C_5$-alkoxycarbonyl, aminocarbonyl, $C_2$–$C_5$-alkylaminocarbonyl, $C_3$–$C_9$-dialkylaminocarbonyl, carboxy, phenyl, phenoxy, phenylthio, pyridyloxy, and $NR^5R^6$, wherein
R⁵ and R⁶ are selected independently of each other from hydrogen and $C_1$–$C_6$-alkyl;
R² is selected from the group consisting of hydrogen, halogen, cyano, $C_1$–$C_6$-alkyl, trifluoromethyl, hydroxy, and $C_1$–$C_4$-alkoxy;
R³ is selected from the group consisting of hydrogen, halogen and $C_1$–$C_6$-alkyl;
R⁴ is selected from the group consisting of hydrogen, $C_1$–$C_6$-alkyl, $C_3$–$C_6$-alkenyl, $C_3$–$C_6$-cycloalkyl, hydroxy, $C_1$–$C_6$-alkoxy and benzyloxy;
k is 0 or 1;
A is selected from the group consisting of $C_1$–$C_6$-alkylene;
a substituted $C_1$–$C_6$-alkylene which is substituted one to three-fold by $C_1$–$C_3$-alkyl, hydroxy, or fluorine;
$C_2$–$C_6$-alkylene, in which a methylene unit is isosterically replaced by O, S, NR⁹, CO, SO or $SO_2$, wherein, with the exception of CO, the isosteric substitution is not adjacent to the amide group and, the residue R⁹, is selected from the group consisting of hydrogen, $C_1$–$C_6$-alkyl, $C_1$–$C_6$-acyl and methane sulfonyl;
$C_2$–$C_6$-alkenylene;
a substituted $C_2$–$C_6$-alkenylene which is substituted once to three-fold by $C_1$–$C_3$-alkyl, hydroxy, fluorine, or cyano;
$C_4$–$C_6$-alkadienylene;
a substituted $C_4$–$C_6$-alkadienylene which is substituted once to twice by $C_1$–$C_3$-alkyl, fluorine, or cyano;
1,3,5-hexatrienylene;
a substituted 1,3,5-hexatrienylene which is substituted by $C_1$–$C_3$-alkyl, fluorine, cyano; and
ethinylene;
D is selected from the group consisting of $C_2$–$C_{10}$-alkylene;
a substituted $C_2$–$C_{11}$-alkylene which is substituted once or twice by $C_1$–$C_3$-alkyl or hydroxy;
$C_1$–$C_{10}$-alkenylene;
a substituted $C_4$–$C_{10}$-alkenylene which is substituted once or twice by $C_1$–$C_3$-alkyl or hydroxy;
$C_4$–$C_{10}$-alkinylene;
a substituted $C_4$–$C_{10}$-alkinylene which is substituted once or twice by $C_1$–$C_3$-alkyl or hydroxy; and $C_2$–$C_{10}$-alkylene, $C_4$–$C_{10}$-alkenylene or $C_4$–$C_{10}$-alkinylene, wherein one to three methylene units are isosterically replaced by O, S, $NR^{10}$, CO, SO, or $SO_2$, wherein
R¹⁰ has the same meaning as R⁹, but is selected independently thereof;
E is

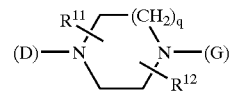

wherein
q is 1;
R¹¹ is selected from the group consisting of hydrogen $C_1$–$C_3$-alkyl, hydroxy, hydroxymethyl, carboxy, and $C_2$–$C_7$-alkoxycarbonyl and
R¹² is selected from the group consisting of hydrogen, and an oxo group adjacent to a nitrogen atom; and wherein R¹¹ and R¹² may together form a $C_1$–$C_3$-alkylene bridge under formation of a bicyclic ring system;
G is G1, wherein
$G^1$ is $-(CH_2)_r-(CR^{14}R^{15})_s-R^{13}$
r is 0, 1 or 2;
s is 0 or 1;
R¹³ is selected from the group consisting of hydrogen, $C_1$–$C_6$-alkyl, $C_3$–$C_6$-alkenyl, $C_3$–$C_6$-alkinyl, $C_3$–$C_8$-cycloalkyl; benzyl, phenyl;
monocyclic aromatic five or six-membered heterocycles, which contain one to three hetero-atoms selected from the group consisting of N, S and O, wherein the heterocycles are either bound directly or over a methylene group;
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;
anellated bi- and tricyclic aromatic or partially hydrogenated heterocyclic ring systems with 8 to 16 ring atoms and at least one aromatic ring, wherein one to three ring atoms are selected from the group consisting of N, S and O, wherein the linkage occurs either over an aromatic ring or a hydrogenated ring and either directly or over a methylene group;
R¹⁴ has the same meaning as R¹³, but is selected independently thereof;
R¹⁵ is selected from the group consisting of hydrogen, hydroxy, methyl, benzyl, phenyl;
monocyclic aromatic five or six-membered heterocycles, which contain one to three hetero-atoms selected from the group consisting of N, S and O, wherein the heterocycles are either bound directly or over a methylene group;
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group; and
anellated bi- and tricyclic aromatic or partially hydrogenated heterocyclic ring systems with 8 to 16 ring atoms and at least one aromatic ring, wherein one to three ring atoms can be selected from N, S and O and the linkage may occur either over an aromatic ring or a hydrogenated ring and either directly or over a methylene group;

wherein G is not phenyl, N-containing heteroaryl, —(CH$_2$)$_{0-2}$—CH$_2$—C$_6$H$_5$, —(CH$_2$)$_{0-2}$—CH$_2$—C$_5$H$_5$N;

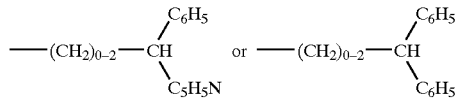

wherein the phenyl group or moiety may be substituted by one or two members selected from the group consisting of halogen, a C$_1$–C$_6$ alkyl, trifluoromethyl and a C$_1$–C$_6$ alkoxy, when R$^1$ is hydrogen, a halogen, a C$_1$–C$_6$-alkyl, a C$_1$–C$_6$-alkoxy, a C$_1$–C$_6$-alkylthio, a C$_3$–C$_8$-cycloalkyloxy, a C$_3$–C$_8$-cycloalkylthio, a C$_2$–C$_7$-alkoxycarbonyl, carboxy, a phenyl, a phenoxy, a phenylthio, 3-pyridyloxy or 3-pyridylthio;

R$^2$ is hydrogen, a hydroxy, a C$_1$–C$_7$-alkanoyloxy or a C$_1$–C$_7$-alkoxycarbonyloxy, or when R$^1$ and R$_2$ are adjacent to each other, they may combine to form tetramethylene or —CH$_2$OCR$^{8a}$R$^{9a}$O—, wherein R$^{8a}$ and R$^{9a}$ are the same or different and are each a C$_1$–C$_6$-alkyl;

R$^3$ is hydrogen, a C$_1$–C$_6$-alkyl or a hydroxy-C$_1$–C$_6$-alkyl;

A is a C$_1$–C$_6$-alkylene or —(CR$^{6a}$=CR$^{7a}$)ra-, wherein R$^{6a}$ is hydrogen, a C$_1$–C$_6$-alkyl or a phenyl, R$^{7a}$ is hydrogen, a C$_1$–C$_6$-alkyl, cyano or a phenyl, and ra is 1 or 2;

R$^4$ is hydrogen;

D is a C$_1$–C$_6$-alkylene or a C$_4$–C$_{10}$-alkylene interrupted by at least one double bond; and E is selected from the group consisting of piperazine, piperazine, which is substituted by C$_1$–C$_6$-alkyl, homopiperazine, and homopiperazine, which is substituted by C$_1$–C$_6$-alkyl.

3. The compound according to claim 2, wherein

R$^1$ is selected from the group consisting of hydrogen, halogen, cyano, methyl, ethyl, trifluoromethyl, hydroxy, C$_1$–C$_4$-alkoxy, benzyloxy, C$_1$–C$_5$-alkanoyloxy, methylthio, ethylthio, methoxycarbonyl, terrt-butoxycarbonyl, aminocarbonyl, carboxy, phenoxy, and phenylthio;

R$^2$ is selected from the group consisting of hydrogen, halogen, trifluoromethyl and hydroxy;

R$^3$ is selected from the group consisting of hydrogen and halogen;

R$^4$ is selected from the group consisting of hydrogen, C$_1$–C$_3$-alkyl, allyl, hydroxy and C$_1$–C$_5$-alkoxy;

k is 0 or 1;

is selected from the group consisting of C$_1$–C$_6$-alkylene;

a substituted C$_1$–C$_6$-alkylene which is substituted once or twice by C$_1$–C$_3$-alkyl, hydroxy or fluorine;

C$_2$–C$_6$-alkylene, in which a methylene unit is isosterically replaced by O, S, NR$^9$, CO, SO or SO$_2$, wherein, with the exception of CO, the isosteric substitution is not adjacent to the amide group;

C$_2$–C$_6$-alkenylene;

a substituted C$_2$–C$_6$-alkenylene which is substituted once or twice by C$_1$–C$_3$-alkyl, hydroxy or fluorine;

C$_4$–C$_6$-alkadienylene;

a substituted C$_4$–C$_6$-alkadienylene which is substituted by C$_1$–C$_3$-alkyl or one or two fluorine atoms;

1,3,5-hexatrienylene;

a substituted 1,3,5-hexatrienylene which is substituted by fluorine;

D is selected from the group consisting of C$_2$–C$_8$-alkylene;

a substituted C$_2$–C$_8$-alkylene which is substituted once or twice by methyl or hydroxy;

C$_4$–C$_8$-alkenylene;

a substituted C$_4$–C$_8$-alkenylene which is substituted once or twice by methyl or hydroxy;

C$_4$–C$_8$-alkinylene;

a susbstituted C$_4$–C$_8$-alkinylene which is substituted once or twice by methyl or hydroxy; and C$_2$–C$_8$-alkylene, C$_4$–C$_8$-alkenylene or C$_4$–C$_8$-alkinylene, wherein one to three methylene units are each isosterically replaced by O, S, NH, N(CH$_3$), N(COCH$_3$), N(SO$_2$CH$_3$), CO, SO or SO$_2$;

E is

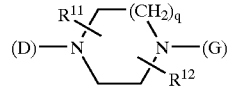

wherein q is 1;

R$^{11}$ is selected from the group consisting of hydrogen C$_1$–C$_3$-alkyl, hydroxymethyl, and carboxy;

R$^{12}$ is selected from the group consisting of hydrogen and an oxo group adjacent to a nitrogen atom;

G is G1, wherein

G$^1$ represents —(CH$_2$)$_r$—(CR$^{14}$R$^{15}$)$_s$—R$^{13}$;

r is 0, 1 or 2;

s is 0 or 1;

R$^{13}$ is selected from the group consisting of hydrogen, C$_1$–C$_6$-alkyl, C$_3$–C$_8$-cycloalkyl; benzyl, phenyl, benzcyclobutyl, indanyl, indenyl oxoindanyl, naphthyl, dihydronaphthyl, tetrahydronaphthyl, oxotetrahydronaphthyl, biphenylenyl, fluorenyl, oxofluorenyl, anthryl, dihydroanthyrl, oxodihydroanthryl, dioxodihydroanthryl, phenanthryl, dihydrophenanthryl, oxodihydrophenanthryl, dibenzocycloheptenyl, oxodibenzocycloheptenyl, dihydrodibenzocycloheptenyl, oxodihydrodibenzocycloheptenyl, dihydrodibenzocycloooctenyl, tetrahydrodibenzocyclooctenyl, oxotetrahydrodibenzocyclooctenyl bound directly over a methylene group;

furyl, thienyl, pyrrolyl, oxazolyl, isoxazolyl, thizolyl, isothiazolyl, pyrazolyl, imidazolyl, oxadiazolyl, thiadiazolyl, triazolyl, pyridyl, pyrazinyl, pyridazinyl, pyrimidinyl, triazinyl, imidazothiazolyl, benzofuryl, dihydrobenzofuryl, benzothienyl, dihydrobenzothienyl, indolyl, indolinyl, isoindolinyl, oxoindolinyl, dioxoindolinyl, benzoxazolyl, oxobenzooxaolinyl, benzooisoxazolyl, oxobenzoisoxazolinyl, benzothiazolyl, oxobenzthiazolinyl, benzoisothiazolyl, oxobenzoisothiazolinyl, benzoimidazolyl, oxobenzoimidazolinyl, indazolyl, oxoindazolinyl, benzofurazanyl, benzothiadiazolyl, benzotriazolyl, oxazolopridyl, oxodihydrooxazolopyridyl, thiazolopyridyl, oxodihydrooxazolopyridyl, thiazolopyridyl, oxodihydrothiazolopyridyl, isothiazolopyridyl, imidazopyridyl, oxodihydroimidazopyridyl, pyrazolopyridyl, oxodihydropyrazolopyridyl, thienopyrimidinyl, chromanyl, chromanonyl, benzopyranyl, chromonyl, quinoloyl, isoquinoloyl, dihydroquinolyl, oxodihydroquinolinyl, tetrahydroquinolyl, oxotetrahydroquinolinyl, benzodioxanyl, quinoxalinyl, quinazolinyl, naphthyridinyl, carbazolyl, tetrahydrocarbazolyl, acridinyl, oxodihydroacridinyl, phenanthridinyl, dihydrophenanthridinyl, oxodihyrophenanthridinyl, dibenzoisoquinolinyl, dihydrodibenzoisoquinolinyl, oxodihydrodibenzoisoquinolinyl, phenothiazinyl, dihydrodibenzooxepinyl, oxodihydrodibenzooxepinyl, benzocycloheptathienyl, oxobenzocycloheptathienyl, dihydrothienobenzothiepinyl, oxodihydrothienobenzothiepinyl, dihydrothienobenzothiepinyl, oxodihydrodibenzothiepinyl, octahydrodibenzothiepinyl, dibenzoazepinyl, dihydrodibenzoazepinyl, oxodihydrodibenzoazepinyl, ocathydrodibenzoazepinyl, benzocycloheptapyridyl, oxobenzocycloheptapyridyl, pyridobenzoazepinyl, dihydropyridobenzoazepinyl, oxodihydropyridobenzoazepinyl, dihydropyridobenzodiazepinyl, dihydrodibenzooxazepinyl, dihydropyridobenzooxepinyl, dihydropyridobenzooxazepinyl, oxodihydropyridobenzooxazepinyl, dihydropyridobenzothiazepinyl and oxodihydropyridobenzothiazepinyl bound directly or over a methylene group;

$R^{14}$ has the same meaning as $R^{13}$, but is selected independently thereof;

$R^{15}$ is selected from the group consisting of hydroxy, methyl, benzyl, phenyl, indanyl, indenyl, naphthyl, dihydronaphthyl, tetrahydronaphthyl, furyl, thienyl, pyrrolyl, oxazolyl, isoxazolyl, thiazolyl, isothiazolyl, pyrazolyl, imidazolyl, imidazolyl, oxadiazolyl, thiadiazolyl, triazolyl, pyridyl, pyrazinyl, pyridazinyl, pyrimidinyl, triazinyl, benzofuryl, benzothienyl, indolyl, indolinyl, benzooxazolyl, benzothiazolyl, benzoimidazolyl, chromanyl, quinolyl, and tetrahydroquinolyl bound directly or over a methylene group.

4. The compounds according to claim 3, wherein $R^1$ is selected from the group consisting of hydrogen, fluorine, chlorine, bormine, methyl, ethyl, trifluoromethyl, hydroxy, $C_1$–$C_4$-alkoxy, methylthio, ethylthio, carboxy and phenoxy;

$R^2$ is selected from the group consisting of hydrogen, chlorine and methyl;

$R^3$ is selected from hydrogen;

$R^4$ is selected from the group consisting of hydrogen, $C_1$–$C_3$-alkyl and hydroxy;

k is 0;

A is selected from the group consisting of $C_2$–$C_6$-alkylene;

a substituted $C_2$–$C_6$-alkylene which is substituted once or twice by hydroxy or fluorine;

$C_2$–$C_6$-alkylene, wherein a methylene unit is isosterically replaced by O, S or CO, wherein, with the exception of CO, the isosteric substitution cannot be adjacent to the amide group;

$C_2$–$C_6$-alkenylene;

a $C_2$–$C_6$-alkenylene which is substituted once or twice by $C_1$–$C_3$-alkyl or fluorine; and $C_4$–$C_6$-alkadienylene;

D is selected from the group consisting of $C_2$–$C_8$-alkylene;

a substituted $C_2$–$C_6$-alkylene which is substituted by methyl or hydroxy;

$C_4$–$C_8$-alkenylene;

a substituted $C_4$–$C_8$-alkenylene which is substituted by hydroxy;

$C_4$–$C_8$-alkinylene;

a susbtituted $C_4$–$C_8$-alkinylene which is substituted by hydroxy; and $C_2$–$C_8$-alkylene, $C_4$–$C_8$-alkenylene or $C_4$–$C_8$-alkinylene, wherein a methylene unit is isosterically replaced by O, S, NH, N($CH_3$), CO, or $SO_2$, or an ethylene group is isosterically replace by a group NH—CO or CO—NH, or a propylene group is isosterically replaced by a group NH—CO—O or O—CO—NH;

E is selected from the group consisting of piperazine, hexahydro-1,4-diazepine, and substituted piperazine and hexahydro-1,4-diazepine wherein the ring is substituted by one or two methylene groups or by an oxo group adjacent to a nitrogen atom;

G is selected from the group consisting of hydrogen, $C_3$–$C_8$-cycloalkyl, methoxycarbonyl, tert-butoxycarbonyl, benxyloxycarbonyl, trifluoroacetyl, diphenyl phosphinoyl, and —$(CH_2)_r$—$(CR^{14}R^{15})_s$—$R^{13}$;

r is 0 or 1;

s is 0 or 1;

$R^{13}$ is selected from the group consisting of hydrogen, methyl, benzyl, phenyl, indanyl, indenyl, oxoindanyl, naphthyl, tetrahydronaphthyl, fluorenyl, oxofluorenyl, anthryl, dihydroanthryl, oxodihydroanthryl, dioxodihydroanthryl, phenanthryl, dihydrophenanthryl, oxodihydrophenanthryl, dibenzocycloheptenyl, dihydrodibenzocycloheptenyl, oxodihydrodibenzocycloheptenyl, bound directly over a methylene group, furyl, thienyl, oxazolyl, thiazolyl, imidazolyl, oxadiazolyl, pyridyl, pyrazinyl, pyrimidinyl, imidazothiazolyl, benzofuryl, benzothienyl, indolyl, indolinyl, oxoindolinyl, dioxoindolinyl, benzoxazolyl, oxobenzooxaolinyl, benzooisoxazolyl, oxobenzoisoxazolinyl, benzothiazolyl, oxobenzthiazolinyl, benzimidazolyl, oxobenzimidazolinyl, indazolyl, benzofurazanyl, benzothiadiazolyl, oxazolopridyl, oxodihydrooxazolopyridyl, imidazopyridyl, oxodihydroimidazopyridyl, chromanyl, chromanonyl, benzopyranyl, chromonyl, quinoloyl, isoquinoloyl, oxodihydroquinolinyl, tetrahydroquinolyl, oxotetrahydroquinolinyl, benzodioxanyl, quinazolinyl, carbazolyl, acridinyl, dihydroacridinyl, oxodihyroscridinyl, dibenzoisoquinolinyl, dihydrodibenzoisoquinolinyl, oxodihydrodibenzoisoquinolinyl, phenothiazinyl, dihydrodibenzooxepinyl, oxodihydrodibenzooxepinyl, benzocycloheptathienyl, oxobenzocycloheptathienyl, dihydrothienobenzothiepinyl, oxodihydrothienobenzothiepinyl, dihydrothienobenzothiepinyl, oxodihydrodibenzothiepinyl, octahydrodibenzothiepinyl, dibenzoazepinyl, dihydrodibenzoazepinyl, oxodihydrodibenzoazepinyl, ocathydrodibenzoazepinyl, benzocycloheptapyridyl, oxobenzocycloheptapyridyl, pyridobenzoazepinyl, dihydropyridobenzoazepinyl, oxodihydropyridobenzoazepinyl, dihydropyridobenzodiazepinyl, dihydrodibenzooxazepinyl, dihydropyridobenzooxepinyl, dihydropyridobenzooxazepinyl, oxodihydropyridobenzooxazepinyl, dihydropyridobenzothiazepinyl, and oxodihydropyridobenzothiazepinyl bound directly or over a methylene group;

$R^{14}$ is selected from the group consisting of hydrogen, methyl, benzyl, and phenyl;

$R^{15}$ is selected from the group consisting of hydroxy, methyl, benzyl, phenyl, naphthyl, tetrahydronaphthyl, furyl, thienyl, oxazolyl, thiazolyl, imidazolyl, benzofuryl, benzothienyl, indolyl, indolinyl, benzoxazolyl, benzothiazolyl, benzoimidazolyl, chromanyl, quinolyl, and tetrahydroquinolyl bound directly or over a methylene group;

wherein the group —$NR^{13}R^{15}$ represents a ring bound over the nitrogen of a residue from the series pyrrolidine, piperidine, hexahydroazepine, piperazine, hexahydrodiazepine, thiomorpholine, 7-aza-bicycloheptane, 2,5-diaza-bicyclo heptane, indoline, isoindoline, (1H)-dihydroquinoline, (1H)-tetrahydroquinolin, (2H)-tetrahydroisoquinoline, (4H)-dihydrobenzooxazine, (4H)-dihydrobenzothiazine, (1H)-tetrahydrobenzoazepine, (1H)-tetrahydrobenzoazepine, (5H)-tetrahydrobenzooxazepine, (5H)-tetrahydrobenzothiazepine, (10H)-dihydroacridine, 1,2,3,4-tetrahydroacridanone, (10H)-dihydrophenanthridine, (1H)-dihyrdobenzoisoquinoline, (10H)-phenothiazine, (5H)-dibenzoazepine, (5H)-dihydrodibenzoazepine, (5H)-octahydrodibenzoazepine, dihydrobenzoisoquinoline, (5H)-dihydrodibenzoazepine, (5H)-dihydrodibenzodiazepine, (5H)-dihydrobenzoazepine, (11H)-dihydrodibenzooxazepine, (11H)-dihydrodibenzothiazepine, (10H)-dihydrodibenzooxazepine, (5H)-dihydrobenzopyridoazepine and (1H)-oxodihydrobenzopyridodiazepine, wherein aromatic ring systems in the substitutents may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_{17}$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide in the case of two adjacent residues on the aromatic ring; and wherein alkyl-alkenyl- and cycloalkyl residues in the groups G can be substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

5. The compounds according to claim 4, wherein
$R^1$ is selected from the group consisting of hydrogen, fluorine, methyl, trifluoromethyl, and ethylthio;
$R^2$, $R^3$ and $R^1$ are each hydrogen;

k is 0;

A is selected from the group consisting of ethylene, propylene and butylene;

a substituted ethylene, propylene and butylene which are each substituted by hydroxy, one or two fluorine atoms;

$OCH_2$;

$SCH_2$;

ethenylene; and 1,3-butadienylene;

D is selected from the group consisting of $C_2$–$C_6$-alkylene;

a substituted $C_2$–$C_6$-alkylene which is substituted by hydroxy;

$C_4$–$C_6$-alkenylene;

$C_1$–$C_6$-alkinylene; and $C_2$–$C_6$-alkylene, $C_4$–$C_6$-alkenylene or $C_4$–$C_6$-alkinylene, wherein one or two methylene units are isosterically replaced by O, NH, CO, or $SO_2$;

E is piperazine or hexahydro-1,4-diazeazepine.

6. The compound according to claim 2, which is selected from the group consisting of N-[4-(4-diphenylmethylpiperazin-1-yl)-3-hydroxybutyl]-3-pyridin-3-yl-acrylamide; N-[3-(4-diphenylmethylpiperazin-1-yl)-propoxy]-3-pyridin-3-yl-acrylamide; N-[4-(4-diphenylmethylpiperazin-1-yl)-4-oxo-butyl]-3-pyridin-3-yl-acrylamide; N-[3-(4-diphenylmethylpiperazin-1-sulfonyl)-3-propyl]-3-pyridin-3-yl-acrylamide; N-{2-[2-(4-diphenylmethylpiperazin-1-yl)-ethoxy]-ethyl}-3-pyridin-3-yl-acrylamide; N-(4-{4-[bis-(4-fluorophenyl)-methyl]-piperazin-1-yl}-but-2-in-yl)-3-pyridin-3-yl-acrylamide; N-{4-[4-(4-carboxyphenyl-phenylmethyl)-piperazin-1-yl]-butyl}-3-pyridin-3-yl-acrylamide; N-(4-{4-[(4-aminophenyl)-phenylmethyl]-piperazin-1-yl}-butyl)-3-pyridin-3-yl-acrylamide; N-{4-[4-(9H-fluoren-9-yl)-piperazin-1-yl]-butyl}-2-(pyridin-3-yloxy)-acetamide; N-{5-[4-(9H-fluoren-9-yl)-piperazin-1-yl]-penyl}-3-pyridin-3-yl-acrylamide; N-{6-[4-(9H-fluoren-9-yl)-piperazin-1-yl]-hexyl}-3-pyridin-3-yl-acrylamide; 3-pyridin-3-yl-N-{4-[4-(1,2,3,4-tetrahydronaphthalin-1-yl)-piperazin-1-yl]-butyl)-acrylamide; 3-pyridin-3-yl-N-(4-[4-(5,6,7,8-tetrahydronaphthalin-1-yl)-piperazin-1-yl]-butyl)-acrylamide; N-{4-[4-(naphthalin-1-yl)-piperazin-1-yl]-butyl}-3-pyridin-3-yl-acrylamide; N-[4-(4-biphenyl-2-yl)-butyl]-3-pyridin-3-yl-propionamide; N-[5-(4-biphenyl-2-yl-piperazin-1-yl)-pentyl]-3-pyridin-3-yl-acrylamide; N-[6-(4-biphenyl-2-yl-piperazin-1-yl)-hexyl]-3-pyridin-3-yl-acrylamide; N-[4-(4-biphenyl-2-yl-piperazin-1-yl)-butyl]-2-(pyridin-3-yloxy-acetamide; N-[4-(4-biphenyl-2-yl-piperazin-1-yl)-butyl]-5-(pyridin-3-yl)-penta-2,4-dienoic acid amide; N-{4-[4-(10,11-dihydro-5H-dibenzo[a,d]cyclohepten-5-yl)-piperazin-1-yl]-butyl}-3-pyridin-3-yl-propionamide; N-{5-[4-(10,11-dihydro-5H-dibenzo[a,d]cyclohepten-5-yl)-piperazin-1-yl]-pentyl}-3-pyridin-3-yl-acrylamide; N-{6-[4-(10,11-dihydro-5H-dibenzo[a,d]cyclohepten-5-yl)-piperazin-1-yl]-hexyl}-3-pyridin-3-yl-propionamide; N-{4-[4-(10,11-dihydro-5H-dibenzo[a,d]cyclohepten-5-yl)-piperazin-1-yl]-butyl}-5-(pyridin-3-yl)-penta-2,4-dienoic acid amide; N-{4-[4-(6,11-dihydrodibenzo[b,e]oxepin-11-yl)-piperazin-1-yl]-butyl-3-pyridin-3-yl-propionamide; N-{2-[4-(6,11-dihydrodibenzo[b,e]thiepin-11-yl)-piperazin-1-yl]-ethyl}-3-pyridin-3-yl-acrylamide; N-[4-(4-diphenylacetyl-piperazin-1-yl)-butyl]-3-pyridin-3-yl-acrylamide; N-[4-(4-benzoylpiperazin-1-yl)-butyl]-3-pyridin-3-yl-acrylamide; N-(4-[4-(2-aminobenzoyl)-piperazin-1-yl]-butyl}-3-pyridin-3-ylacrylamide; N-{4-[4-(4-carboxybenzoyl)-piperazin-1-yl]-butyl}-3-pyridin-3-yl-acrylamide; N-{4-[4-(biphenyl-2-carbonyl)-piperazin-1-yl]-butyl}-3-pyridin-3-yl-acrylamide; N-(4-[4-(9-oxo-9H-fluoren-4-carbonyl)-piperazin-1-yl]-butyl}-3-pyridin-3-yl-acrylamide; N-{4-[4-(furan-2-carbonyl)-piperazin-1-yl]-butyl}-3-pyridin-3-yl-acrylamide; N-{4-(4-(naphthalin-1-yl-aminocarbonyl)-piperazin-1-yl]-butyl}-3-pyridin-3-yl-propionamide; N-{4-[4-(diphenylaminocarbonyl)-piperazin-1-yl]-butyl}-3-pyridin-3-yl-acrylamide; N-{4-[4-(naphthalin-2-sulfonyl)-piperazin-1-yl]-butyl}-3-pyridin-3-yl-acrylamide; N-[4-(4-diphenylphosphinoyl-piperazin-1-yl)-butyl]-3-pyridin-3-yl-acrylamide; N-[4-(4-bipheny-2-yl-piperazin-1-yl)-butyl]-3-pyridin-3-yl-acrylamide; N-{4-[4-(9H-fluoren-9-yl)-piperazin-1-yl]-butyl}-3-pyridin-3-yl-acrylamide; and N-{4-[4-(10,11-dihydro-5H-dibenzo[a,d]cyclohepten-5-yl)-piperazin-1-yl]-butyl}-3-pyridin-3-yl-acrylamide.

7. A method for the production of compounds according to formula (I)

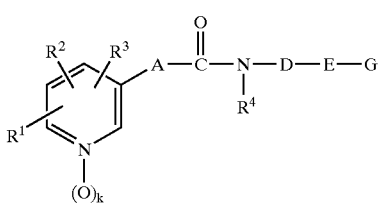

wherein carboxylic acids of formula (II)

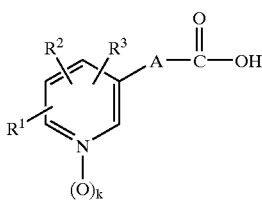

in which $R^1$, $R^2$, $R^3$, A and k have the meaning given below or their respective derivatives are reacted with compounds of formula (III)

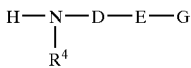

wherein D, E, and G and R4 are defined below in a form of the respective free base or the respective free acid addition salt at a temperature between about −40° C. and about 180° C.
wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_{1-C_7}$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^1$ and $R^2$, if adjacent, may form a bridge selected from —$(CH_2)_4$— and —$(CH=CH)_2$— or $CH_2O$—$CR^7R^8$—O—, wherein $R^7$ and $R^8$ are selected independently from each other from hydrogen and $C_1$–$C_6$-alkyl;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a substituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

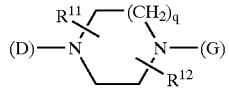

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

and wherein $R^{11}$ and $R^{12}$ may together form a $C_1$–$C_3$-alkylene bridge under formation of a bicyclic ring system;

G is G1, wherein $G^1$ is —$(CH_2)_r$—$(CR^{14}R^{15})_s$—$R^{13}$ r is 0, 1, 2 or 3;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles;

saturated or unsaturated four to eight-membered heterocycles which contain one or two hetero-atoms selected from the group consisting of N, S and O;

benzyl, phenyl;

monocyclic aromatic five or six-membered heterocycles which contain one to three hetero-atoms selected from the group consisting of N, S and O where the heterocycles are either bound directly or over a methylene group;

anellated bi- and tricyclic aromatic or partially hydrogenated carbocyclic ring systems with 8 to 16 ring atoms and at least one aromatic ring, wherein the linkage may occur either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage may occur either over an aromatic ring or a hydrogenated ring and either directly or over a methylene group;

$R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the heterocycles are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrogenated ring and either directly or over a methylene group.

8. A pharmaceutical composition comprising the compound of formula (I)

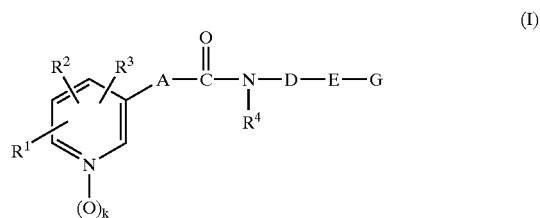

wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a susbstituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene, a substituted $C_2$–$C_6$-alkenylene which is substituted once to three-fold by $C_1$–$C_3$-alkyl, hydroxy, $C_1$–$C_3$-alkoxy, or fluorine, cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

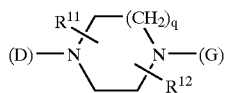

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

G is G1, wherein $G^1$ is —$(CH_2)_r$—$(CR^{14}R^{15})_s$—$R^{13}$ r is 0 to 3;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;

$R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group;

wherein G is not —$(CH_2)_r$—$(CR^{14}R^{15})_s$—$R^{13}$ when $R^{13}$ represents pyridyl or phenyl, substituted by halogen, alkyl, alkoxy or trifluoromethyl;

$R^{14}$ represents hydrogen or phenyl, substituted by halogen, alkyl, alkoxy or trifluoromethyl;

$R^{15}$ represents hydrogen;

A represents alkylene, substituted ethenylene or butadienylene;

D represents alkylene or alkenylene;

E represents piperazine or homopiperazine; and

S is 1;

wherein $G^1$ is not phenyl, N-containing heteroaryl, —$(CH_2)_{0-2}$—$CH_2$—$C_6H_5$, —$(CH_2)_{0-2}$—$CH_2$—$C_5H_5N$,

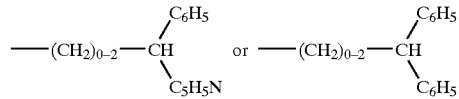

wherein the phenyl group or moiety may be substituted by one or two members selected from the group consisting of halogen, a $C_1$–$C_6$ alkyl, trifluoromethyl and a $C_1$–$C_6$-alkoxy, when $R^1$ is hydrogen, a halogen, a $C_1$–$C_6$-alkyl, a $C_1$–$C_6$-alkoxy, a $C_1$–$C_6$-alkylthio, a $C_3$–$C_8$-cycloalkyloxy, a $C_3$–$C_8$-cycloalkylthio, a $C_2$–$C_7$-alkoxycarbonyl, carboxy, a phenyl, a phenoxy, a phenylthio, 3-pyridyloxy or 3-pyridylthio;

$R^2$ is hydrogen, a hydroxy, a $C_1$–$C_7$-alkanoyloxy or a $C_2$–$C_7$-alkoxycarbonyloxy, or when $R^1$ and $R_2$ are adjacent to each other, they may combine to form tetramethylene or —$CH_2OCR^{8a}R^{9a}O$—, wherein $R^{8a}$ and $R^{9a}$ are the same or different and are each a $C_1$–$C_6$-alkyl;

$R^3$ is hydrogen, a $C_1$–$C_6$-alkyl or a hydroxy-$C_1$–$C_6$-alkyl;

A is a $C_1$–$C_6$-alkylene or —$(CR^{6a}=CR^{7a})ra$-, wherein $R^{6a}$ is hydrogen, a $C_1$–$C_6$-alkyl or a phenyl, $R^{7a}$ is hydrogen, a $C_1$–$C_6$-alkyl, cyano or a phenyl, and ra is 1 or 2;

$R^4$ is hydrogen;

D is a $C_1$–$C_{10}$-alkylene or a $C_4$–$C_{10}$-alkylene interrupted by at least one double bond; and E is selected from the group consisting of piperazine, piperazine, which is substituted by $C_1$–$C_6$-alkyl, homopiperazine, and homopiperazine, which is substituted by $C_1$–$C_6$-alkyl.

9. The pharmaceutical composition according to claim 8, wherein the pharmaceutical composition is present in a solid, peroral administrable form as a tablet, capsule, coated tablet, or as a liquid, peroral administration solution, suspension, effervescent tablet, in the form of tabs or sachets, which may be in the form of a suitable injection or infusion preparation together with suitable pharmaceutically acceptable carriers and adjuvants, in the form of a concentrate, powder or lyophilisate, in the form of a transdermal therapeutic system for systemic treatment, in the form of a gastrointestinal therapeutic system (GITS) for systemic treatment, in the form of a salve, suspension, emulsion, a balm or plaster or in the form of an externally applicable solution, in the form of a rectal, genital, or transurethral administration emulsion, a solution, a liposomal solution, an implant, suppository or a capsule, in the form of a composition capable of being applied nasally, otologically or ophthalmologically, or in a buccally applicable form.

10. The pharmaceutical composition according to claim 8, wherein a dosage unit for single administration contains about 0.001 to about 5000 mg active ingredient.

11. A pharmaceutical composition comprising the compound of formula (I)

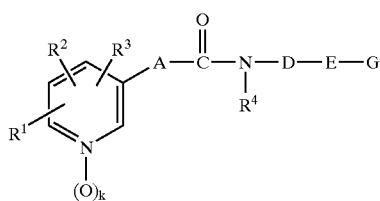

(I)

wherein $R^1$ is selected from the group consisting of hydrogen, halogen, cyano, $C_1$–$C_6$-alkyl, trifluoromethyl, $C_3$–$C^8$-cycloalkyl, $C_1$–$C_6$-hydroxyalkyl, hydroxy, $C_1$–$C_4$-alkoxy, benzyloxy, $C_1$–$C_4$-alkylthio, $C_1$–$C_5$-alkanoyloxy, $C_1$–$C_4$-alkylthio, $C_2$–$C_5$-alkoxycarbonyl, aminocarbonyl, $C_2$–$C_5$-alkylaminocarbonyl, $C_3$–$C_9$-dialkylaminocarbonyl, carboxy, phenyl, phenoxy, phenylthio, pyridyloxy, and $NR^5R^6$, wherein $R^5$ and $R^6$ are selected independently of each other from hydrogen and $C_1$–$C_6$-alkyl;

$R^2$ is selected from the group consisting of hydrogen, halogen, cyano, $C_1$–$C_6$-alkyl, trifluoromethyl, hydroxy, and $C_1$–$C_4$-alkoxy;

$R^3$ is selected from the group consisting of hydrogen, halogen and $C_1$–$C_6$-alkyl;

$R^4$ is selected from the group consisting of hydrogen, $C_1$–$C_6$-alkyl, $C_3$–$C_6$-alkenyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a substituted $C_1$–$C_6$-alkylene which is substituted one to three-fold by $C_1$–$C_3$-alkyl, hydroxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and, the residue $R^9$, is selected from the group consisting of hydrogen, $C_1$–$C_6$-alkyl, $C_1$–$C_6$-acyl and methane sulfonyl;

$C_2$–$C_6$-alkenylene;

a substituted $C_2$–$C_6$-alkenylene which is substituted once to three-fold by $C_1$–$C_3$-alkyl, hydroxy, fluorine, or cyano;

$C_1$–$C_6$-alkadienylene;

a substituted $C_4$–$C_6$-alkadienylene which is substituted once to twice by $C_1$–$C_3$-alkyl, fluorine, or cyano;

1,3,5-hexatrienylene;

a substituted 1,3,5-hexatrienylene which is substituted by $C_1$–$C_3$-alkyl, fluorine, cyano, and ethinylene;

D is selected from the group consisting of $C_2$–$C_{10}$-alkylene;

a substituted $C_2$–$C_{10}$-alkylene which is substituted once or twice by $C_1$–$C_3$-alkyl or hydroxy;

$C_4$–$C_{10}$-alkenylene;

a substituted $C_4$–$C_{10}$-alkenylene which is substituted once or twice by $C_1$–$C_3$-alkyl or hydroxy;

$C_1$–$C_{10}$-alkinylene;

a substituted $C_4$–$C_{10}$-alkinylene which is substituted once or twice by $C_1$–$C_3$-alkyl or hydroxy; and $C_2$–$C_{10}$-alkylene, $C_4$–$C_{10}$-alkenylene or $C_4$–$C_{10}$-alkinylene, wherein one to three methylene units are isosterically replaced by O, S, $NR^{10}$, CO, SO, or $SO_2$, wherein $R^{10}$ has the same meaning as $R^9$, but is selected independently thereof;

E is

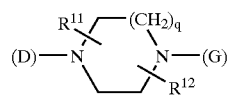

wherein q is 1;

$R^{11}$ is selected from the group consisting of hydrogen $C_1$–$C_3$-alkyl, hydroxy, hydroxymethyl, carboxy, and $C_2$–$C_7$-alkoxycarbonyl; and $R^{12}$ is selected from the group consisting of hydrogen, and an oxo group adjacent to a nitrogen atom;

and wherein $R^{11}$ and $R^{12}$ may together form a $C_1$–$C_3$-alkylene bridge under formation of a bicyclic ring system;

G is G1, wherein $G^1$ is —$(CH_2)_r$—$(CR^{14}R^{15})_s$—$R^{13}$;

r is 0, 1 or 2;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl, benzyl, phenyl;

monocyclic aromatic five or six-membered heterocycles, which contain one to three hetero-atoms selected from the group consisting of N, S and O, wherein the heterocycles are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O, wherein the linkage occurs either over an aromatic ring or a hydrogenated ring and either directly or over a methylene group;

$R^{14}$ has the same meaning as $R^{13}$, but is selected independently thereof;

$R^{15}$ is selected from the group consisting of hydrogen, hydroxy, methyl, benzyl, phenyl;

monocyclic aromatic five or six-membered heterocycles, which contain one to three hetero-atoms selected from the group consisting of N, S and O, wherein the heterocycles are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogented ring and either directly or over a methylene group; and anellated bi- and tricyclic aromatic or partially hydrogenated heterocyclic ring systems with 8 to 16 ring atoms and at least one aromatic ring, wherein one to three ring atoms can be selected from N, S and O and the linkage may occur either over an aromatic ring or a hydrogenated ring and either directly or over a methylene group, wherein G is not phenyl, N-containing heteroaryl, —(CH$_2$)$_{0-2}$—CH$_2$—C$_6$H$_5$, —(CH$_2$)$_{0-2}$—CH$_2$—C$_5$H$_5$N,

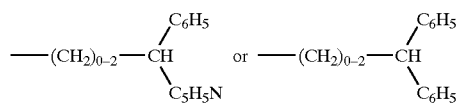

wherein the phenyl group or moiety may be substituted by one or two members selected from the group consisting of halogen, a C$_1$–C$_6$ alkyl, trifluoromethyl and a C$_1$–C$_6$ alkoxy, when $R^1$ is hydrogen, a halogen, a C$_1$–C$_6$-alkyl, a C$_1$–C$_6$-alkoxy, a C$_1$–C$_6$-alkylthio, a C$_3$–C$_8$-cycloalkyloxy, a C$_3$–C$_8$-cycloalkylthio, a C$_2$–C$_7$-alkoxycarbonyl, carboxy, a phenyl, a phenoxy, a phenylthio, 3-pyridyloxy or 3-pyridylthio;

$R^2$ is hydrogen, a hydroxy, a C$_1$–C$_7$-alkanoyloxy or a C$_2$–C$_7$-alkoxycarbonyloxy, or when $R^1$ and $R_2$ are adjacent to each other, they may combine to form tetramethylene or —CH$_2$OCR$^{8a}$R$^{9a}$O—, wherein R$^{8a}$ and R$^{9a}$ are the same or different and are each a C$_1$–C$_6$-alkyl;

$R^3$ is hydrogen, a C$_1$–C$_6$-alkyl or a hydroxy-C$_1$–C$_6$-alkyl;

A is a C$_1$–C$_6$-alkylene or —(CR$^{6a}$=CR$^{7a}$)ra-, wherein R$^{6a}$ is hydrogen, a C$_1$–C$_6$-alkyl or a phenyl, R$^{7a}$ is hydrogen, a C$_1$–C$_6$-alkyl, cyano or a phenyl, and ra is 1 or 2;

$R^4$ is hydrogen;

D is a C$_1$–C$_{10}$-alkylene or a C$_4$–C$_{10}$-alkylene interrupted by at least one double bond; and E is selected from the group consisting of piperazine, piperazine, which is substituted by C$_1$–C$_6$-alkyl, homopiperazine, and homopiperazine, which is substituted by C$_1$–C$_6$-alkyl.

12. A method of inhibiting tumor cell growth in a human or animal body comprising administering to the human or animal body in need thereof an amount of a pharmaceutical composition effective for inhibiting tumor cell growth, wherein the pharmaceutical composition includes a compound of general formula (I)

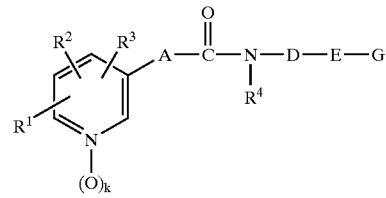

wherein:

$R^1$ is selected from the group consisting of hydrogen, halogen, cyano, C$_1$–C$_6$-alkyl, C$_3$–C$_6$-alkenyl, C$_2$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_3$–C$_8$-cycloalkylthio, C$_2$–C$_7$-alkoxycarbonyl, aminocarbonyl, C$_2$–C$_7$-alkylaminocarbonyl, C$_3$–C$_{13}$-dialkylaminocarbonyl, carboxy, phenyl, phenoxy, phenylthio, pyridyloxy, pyridylthio, and NR$^5$R$^6$, wherein $R^5$ and $R^6$ are selected independently of each other from the group consisting of hydrogen, C$_1$–C$_6$-alkyl, C$_3$–C$_6$-alkenyl, C$_3$–C$_6$-alkinyl, benzyl and phenyl;

$R^2$ is selected from the group consisting of hydrogen, halogen, cyano, C$_1$–C$_6$-alkyl, trifluoromethyl, hydroxy, C$_1$–C$_6$-alkoxy, benzyloxy and C$_1$–C$_7$-alkanoyloxy;

$R^3$ is selected from the group consisting of hydrogen, halogen, C$_1$–C$_6$-alkyl, trifluoromethyl and C$_1$–C$_6$-hydroxyalkyl;

$R^4$ is selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1;

A is selected from the group consisting of C$_1$–C$_6$-alkylene;

a susbstituted C$_1$–C$_6$-alkylene which is substituted one to three-fold by C$_1$–C$_3$-alkyl, hydroxy, C$_1$–C$_3$-alkoxy, or fluorine;

C$_2$–C$_6$-alkylene, in which a methylene unit is isosterically replaced by O, S, NR$^9$, CO, SO or SO$_2$, wherein, with the exception of CO, the isosteric substitution is not adjacent to the amide group and R$^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkanesulfonyl;

C$_2$–C$_6$-alkenylene;

a substituted C$_2$–C$_6$-alkenylene which is substituted once to three-fold by C$_1$–C$_3$-alkyl, hydroxy, C$_1$–C$_3$-alkoxy, fluorine;

C$_4$–C$_6$-alkadienylene;

a substituted C$_4$–C$_6$-alkadienylene which is substituted once or twice by C$_1$–C$_3$-alkyl, fluorine, or cyano;

1,3,5-hexatrienylene;

a 1,3,5-hexatrienylene which is substituted by C$_1$–C$_3$-alkyl, fluorine, or cyano; and ethinylene;

D is selected from the group consisting of C$_2$–C$_{10}$-alkylene;

a substituted C$_2$–C$_{10}$-alkylene which is substituted once or twice by C$_1$–C$_6$-alkyl, hydroxy, or C$_1$–C$_6$-alkoxy;

$C_4$–$C_{10}$-alkenylene;
a substituted $C_4$–$C_{10}$-alkenylene which is substituted once or twice by $C_1$–$C_6$-alkyl, hydroxy, or $C_1$–$C_6$-alkoxy;
$C_4$–$C_{10}$-alkinylene;
a substituted $C_4$–$C_{10}$-alkinylene which is substituted once or twice by $C_1$–$C_6$-alkyl, hydroxy, or $C_1$–$C_6$-alkoxy; and
$C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;
E is

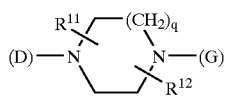

wherein
q is 1;
$R^{11}$ is selected from the group consisting of hydrogen $C_1$–$C_6$-alkyl, hydroxy, hydroxymethyl, carboxy, or $C_2$–$C_7$-alkoxycarbonyl;
$R^{12}$ is selected from the group consisting of hydrogen, $C_1$–$C_6$-alkyl and an oxo group adjacent to a nitrogen atom;
$G^1$ is G1, wherein
$G^1$ is —$(CH_2)_r$—$(CR^{14}R^{15})_s$—$R^{13}$
r is 0 to 3;
s is 0 or 1;
$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;
saturated or unsaturated four to eight-membered heterocycles which contain one or two hetero-atoms selected from the group consisting of N, S and O;
benzyl, phenyl;
monocyclic aromatic five or six-membered heterocycles;
monocyclic aromatic five or six-membered heterocycles which contain one to three hetero-atoms selected from the group consisting of N, S and O where the heteratoms and are either bound directly or over a methylene group;
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;
anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;
$R^{14}$ has the same meaning as $R^{13}$, but is selected independently thereof;
$R^{15}$ is selected from the group consisting of hydrogen, hydroxy, methyl, benzyl, and phenyl;
monocyclic aromatic five or six-member heterocycles, which contain one to three hetero-atoms selected from the group consisting of N, S and O and wherein the hetero-atoms are either bound directly or over a methylene group;
anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;
anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

13. A method of suppressing autoimmune diseases in a human or animal body comprising administering to the human or animal body in need thereof an amount of a pharmaceutical composition effective for suppressing autoimmune reactions, wherein the pharmaceutical composition includes a compound of general formula (I)

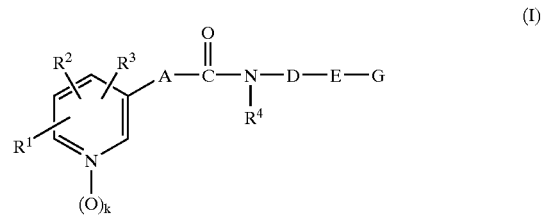

(I)

wherein:
$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein
$R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;
$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;
$R^3$ is selected from the group consisting of hydrogen, halogen, $C_1$–$C_6$-alkyl, trifluoromethyl and $C_1$–$C_6$-hydroxyalkyl;
$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;
k is 0 or 1;
A is selected from the group consisting of $C_1$–$C_6$-alkylene;
a susbstituted $C_1$–$C_6$-alkylene which is substituted one to three-fold by $C_1$–$C_3$-alkyl, hydroxy, $C_1$–$C_3$-alkoxy, or fluorine;
$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_2$–$C_3$-alkyl, fluorine, cyano or phenyl; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

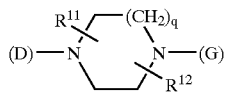

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

G is G1, wherein $G^1$ is —$(CH_2)_r$—$(CR^{14}R^{15})_s$—$R^{13}$ r is 0 to 3;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;

$R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

14. A method for production of compounds according to formula (I)

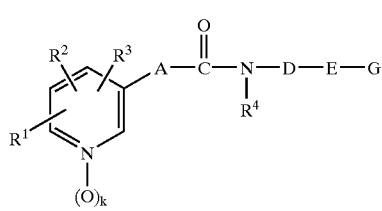

wherein compounds of a formula

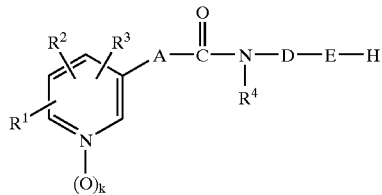

are reacted with a compound of formula (IV)

wherein G is not hydrogen and is defined below, and L is a leaving group selected from the group consisting of alcohol, chlorine, bromine, iodine, sulfonic acid ester, methanesulfonyloxy, trifluoromethanesulfonyloxy, ethanesulfonyloxy, benzensulfonyloxy, p-toluenesulfonyloxy, p-bromobenzenesuflonyloxy, m-nitrobenzenesulfonyloxy, and a terminal epoxide group;

wherein the reaction occurs in an inert solvent at a temperature between about 0° C. and about 180° C., wherein:

$R^1$ is selected from the group consisting of hydrogen, halogen, cyano, $C_1-C_6$-alkyl, $C_3-C_6$-alkenyl, $C_2-C_6$-alkinyl, trifluoromethyl, $C_3-C_8$-cycloalkyl, $C_1-C_6$-hydroxyalkyl, hydroxy, $C_1-C_6$-alkoxy, $C_3-C_6$-alkenyloxy, $C_3-C_6$-alkinyloxy, benzyloxy, $C_1-C_7$-alkanoyloxy, $C_2-C_7$-alkoxycarbonyloxy, $C_1-C_6$-alkylthio, $C_3-C_6$-alkenylthio, $C_3-C_6$-alkinylthio, $C_3-C_8$-cycloalkyloxy, $C_3-C_8$-cycloalkylthio, $C_2-C_7$-alkoxycarbonyl, aminocarbonyl, $C_2-C_7$-alkylaminocarbonyl, $C_3-C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1-C_6$-alkyl, $C_3-C_6$-alkenyl, $C_3-C_6$-alkinyl, benzyl and phenyl;

$R^2$ is selected from the group consisting of hydrogen, halogen, cyano, $C_1-C_6$-alkyl, trifluoromethyl, hydroxy, $C_1-C_6$-alkoxy, benzyloxy and $C_1-C_7$-alkanoyloxy;

$R^3$ is selected from the group consisting of hydrogen, halogen, $C_1-C_6$-alkyl, trifluoromethyl and $C_1-C_6$-hydroxyalkyl;

$R^4$ is selected from the group consisting of hydrogen, $C_1-C_6$-alkyl, $C_3-C_6$-alkenyl, $C_3-C_6$-alkinyl, $C_3-C_6$-cycloalkyl, hydroxy, $C_1-C_6$-alkoxy and benzyloxy;

k is 0 or 1;

A is selected from the group consisting of $C_1-C_6$-alkylene;

a susbstituted $C_1-C_6$-alkylene which is substituted one to three-fold by $C_1-C_3$-alkyl, hydroxy, $C_1-C_3$-alkoxy, or fluorine;

$C_2-C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1-C_6$-alkyl, $C_3-C_6$-alkenyl, $C_3-C_6$-alkinyl, $C_1-C_6$-acyl and $C_1-C_6$-alkanesulfonyl;

$C_2-C_6$-alkenylene, a substituted $C_2-C_6$-alkenylene which is substituted once to three-fold by $C_1-C_3$-alkyl, hydroxy, $C_1-C_3$-alkoxy, fluorine, or cyano;

$C_4-C_6$-alkadienylene;

a substituted $C_4-C_6$-alkadienylene which is substituted once or twice by $C_1-C_3$-alkyl, fluorine, or cyano;

1,3,5-hexatrienylene;

a 1,3,5-hexatrienylene which is substituted by $C_1-C_3$-alkyl, fluorine, or cyano; and ethinylene;

D is selected from the group consisting of $C_2-C_{10}$-alkylene;

a substituted $C_2-C_{10}$-alkylene which is substituted once or twice by $C_1-C_6$-alkyl, hydroxy, or $C_1-C_6$-alkoxy;

$C_4-C_{10}$-alkenylene;

a substituted $C_4-C_{10}$-alkenylene which is substituted once or twice by $C_1-C_6$-alkyl, hydroxy, or C, —$C_6$-alkoxy;

$C_4-C_{10}$-alkinylene;

a substituted $C_4-C_{10}$-alkinylene which is substituted once or twice by $C_1-C_6$-alkyl, hydroxy, or C, —$C_6$-alkoxy; and $C_2-C_{10}$-alkylene, $C_4-C_{10}$-alkenylene or $C_4-C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

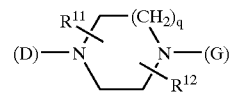

wherein q is 1;

$R^{11}$ is selected from the group consisting of hydrogen $C_1-C_6$-alkyl, hydroxy, hydroxymethyl, carboxy, or $C_2-C_7$-alkoxycarbonyl;

$R^{12}$ is selected from the group consisting of hydrogen, $C_1-C_6$-alkyl and an oxo group adjacent to a nitrogen atom;

G is G1, wherein $G^1$ is —$(CH_2)_r$—$(CR^{14}R^{15})_s$—$R^{13}$ r is 0 to 3;

s is 0 or 1;

$R^{13}$ is selected from the group consisting of hydrogen, $C_1-C_6$-alkyl, $C_3-C_6$-alkenyl, $C_3-C_6$-alkinyl, $C_3-C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;

$R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

15. A method for production of compound according to formula (I)

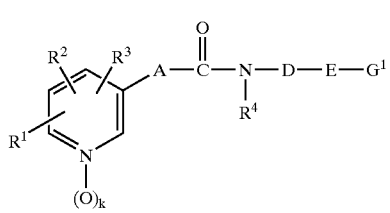

wherein compounds of a formula

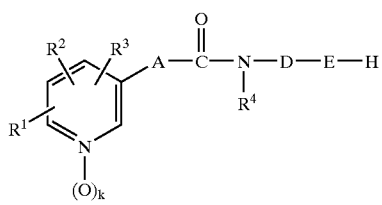

are reacted with a compound of formula (IV)

L—G  (IV)

wherein G is selected from the group consisting of alkyl, alkenyl, alkinyl, cycloalkyl, aryl, aralkyl, heteroaryl and heteroaralkyl;

wherein L is a leaving group selected from the group consisting of alcohol, chlorine, bromine, iodine, sulfonic acid ester, methanesulfonyloxy, trifluoromethanesulfonyloxy, ethanesulfonyloxy, benzensulfonyloxy, p-toluenesulfonyloxy, p-bromobenzenesuflonyloxy, m-nitrobenzenesulfonyloxy, and a terminal epoxide group;

wherein the reaction occurs in an inert solvent at a temperature between about OC and about 180° C., wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_2$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a susbstituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_1$-alkylene;

a substituted $C_2$–$C_{11}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

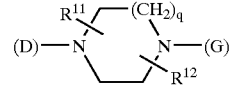

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

$G^1$ is —$(CH_2)_r$—$(CR^{14}R^{15})_s$—$R^{13}$ r is 0 to 3;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group, $R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

16. A method for production of compounds according to formula (I)

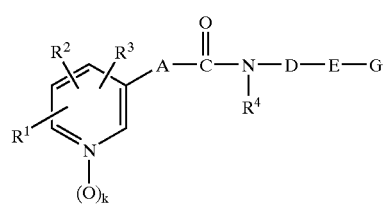
(I)

wherein G is selected from the group consisting of an acyl residue, a carbamoyl residue, a sulfonyl residue and a phosphinoyl residue, wherein compounds of a formula

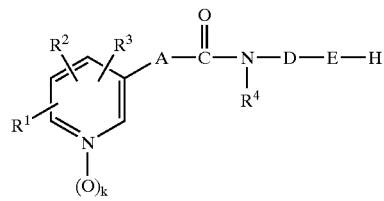

are reacted with a compound of formula (V)

HO—G (V)

wherein G is selected from the group consisting of acyl residues, carbamoyl residues, sulfonyl residues, and phosphinoyl residues, wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a susbstituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

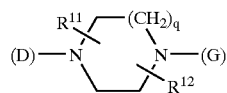

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom.

17. A method for production of compounds according to formula (I)

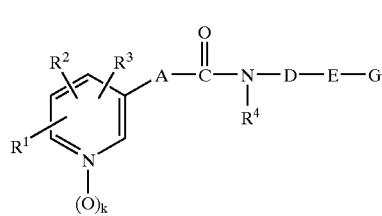

(I)

wherein compounds of a formula

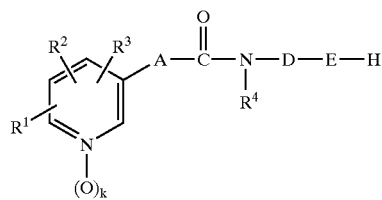

are reacted with a carbonyl group transmitter to an intermediate product which is reacted with a primary or secondary amine having the formula (VI)

H—$NR^{13}R^{15}$ (VI)

wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_8$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a susbstituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$-alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_1$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{11}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

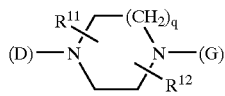

wherein q is 1;

R$^{11}$ is selected from the group consisting of hydrogen C$_1$–C$_6$-alkyl, hydroxy, hydroxymethyl, carboxy, or C$_2$–C$_7$-alkoxycarbonyl;

R$^{12}$ is selected from the group consisting of hydrogen, C$_1$–C$_6$-alkyl and an oxo group adjacent to a nitrogen atom;

wherein G is

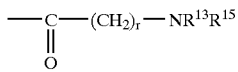

wherein r=0;

R$^{13}$ is selected from the group consisting of hydrogen, C$_1$–C$_6$-alkyl, C$_3$–C$_6$-alkenyl, C$_3$–C$_6$-alkinyl, C$_3$–C$_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the hetero-atoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;

R$^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

18. A method for production of compounds according to formula (I)

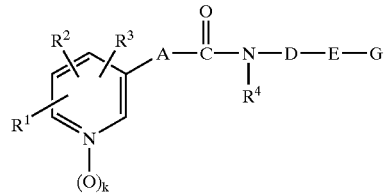

wherein compounds of a formula

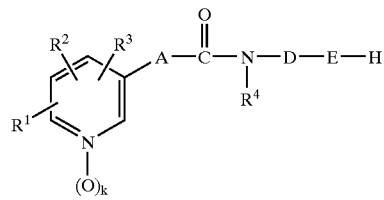

are reacted with a compound of formula (VII)

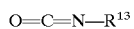

wherein:

R$^1$ is selected from the group consisting of hydrogen, halogen, cyano, C$_1$–C$_6$-alkyl, C$_3$–C$_6$-alkenyl, C$_2$–C$_6$-alkinyl, trifluoromethyl, C$_3$–C$_8$-cycloalkyl, C$_1$–C$_6$-hydroxyalkyl, hydroxy, C$_1$–C$_6$-alkoxy, C$_3$–C$_6$-alkenyloxy, C$_3$–C$_6$-alkinyloxy, benzyloxy, C$_1$–C$_7$-alkanoyloxy, C$_2$–C$_7$-alkoxycarbonyloxy, C$_1$–C$_6$-alkylthio, C$_3$–C$_6$-alkenylthio, C$_3$–C$_6$-alkinylthio, C$_3$–C$_8$-cycloalkyloxy, C$_1$–C$_8$-cycloalkylthio, C$_2$–C$_7$-alkoxycarbonyl, aminocarbonyl, C$_2$–C$_7$-alkylaminocarbonyl, C$_3$–C$_{13}$-dialkylaminocarbonyl, carboxy, phenyl, phenoxy, phenylthio, pyridyloxy, pyridylthio, and NR$^5$R$^6$, wherein R$^5$ and R$^6$ are selected independently of each other from the group consisting of hydrogen, C$_1$–C$_6$-alkyl, C$_3$–C$_6$-alkenyl, C$_3$–C$_6$-alkinyl, benzyl and phenyl;

R$^2$ is selected from the group consisting of hydrogen, halogen, cyano, C$_1$–C$_6$-alkyl, trifluoromethyl, hydroxy, C$_1$–C$_6$-alkoxy, benzyloxy and C$_1$–C$_7$-alkanoyloxy;

R$^3$ is selected from the group consisting of hydrogen, halogen, C$_1$–C$_6$-alkyl, trifluoromethyl and C$_1$–C$_6$-hydroxyalkyl;

R$^4$ is selected from the group consisting of hydrogen, C$_1$–C$_6$-alkyl, C$_3$–C$_6$-alkenyl, C$_3$–C$_6$-alkinyl, C$_3$–C$_6$-cycloalkyl, hydroxy, C$_1$–C$_6$-alkoxy and benzyloxy;

k is 0 or 1;

A is selected from the group consisting of C$_1$–C$_6$-alkylene;

a susbstituted C$_1$–C$_6$-alkylene which is substituted one to three-fold by C$_1$–C$_3$-alkyl, hydroxy, C$_1$–C$_3$-alkoxy, or fluorine;

C$_2$–C$_6$-alkylene, in which a methylene unit is isosterically replaced by O, S, NR$^9$, CO, SO or SO$_2$, wherein, with the exception of CO, the isosteric substitution is not adjacent to the amide group and R$^9$ is selected from the group consisting of hydrogen, C$_1$–C$_6$-alkyl, C$_3$–C$_6$-alkenyl, C$_3$–C$_6$-alkinyl, C$_1$–C$_6$-acyl and C$_1$–C$_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_1$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

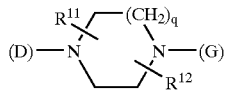

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

wherein G is

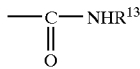

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycle which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group.

19. The pyridylalkane, pyridylalkene and pyridylalkine carboxamindes of formula (I) of claim 1 wherein aromatic ring systems in the substituents $R^1$, $R^2$, $R^4$, $R^5$, $R^6$, $R^{13}$, $R^{14}$, $R^{15}$, and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_2$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in the groups $G^1$, are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino), their cis- and transisomers E- and Z-isomers, diastereomers and other isomers as well as their racemic or non-racemic mixtures and the corresponding endo- and exo-isomers when the ring system E is bicyclic, their tautomers; their acid addition salts and their hydrates and solvates.

20. The compound of formula (I) of claim 2 wherein aromatic ring systems in the substituents $R^1$, $R^2$, $R^4$, $R^5$, $R^6$, $R^{13}$, $R^{14}$, $R^{15}$, and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in $G^1$, are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

21. The pharmaceutical composition of claim 8 aromatic ring systems in the substituents $R^1$, $R^2$, $R^4$, $R^5$, $R^6$, $R^{13}$, $R^{14}$, $R^{15}$, and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in G1, are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

22. The pharmaceutical composition of claim 11 aromatic ring systems in the substituents $R^1$, $R^2$, $R^4$, $R^5$, $R^6$, $R^{13}$, $R^{14}$, $R^{15}$ and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in the groups $G^1$, $G^2$, and $G^3$ are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

23. The method of claim 12 wherein aromatic ring systems in the substituents $R^1$, $R^2$, $R^4$, $R^5$, $R^6$, $R^{13}$, $R^{14}$, $R^{15}$, and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in $G^1$, are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

24. The method of claim 13 wherein aromatic ring systems in the substituents $R^1$, $R^2$, $R^4$, $R^5$, $R^6$, $R^{13}$, $R^{14}$, $R^{15}$, and $R^{16}$, and/or in the ring system —$NR^{13}R^{15}$ may be substituted independently from each other by one to three of the same or different groups selected from the group consisting of halogen, cyano, $C_1$–$C_6$-alkyl, trifluoromethyl, $C_3$–$C_8$-cycloalkyl, phenyl, benzyl, hydroxy, $C_1$–$C_6$-hydroxyalkyl, $C_1$–$C_6$-alkoxy, $C_1$–$C_6$-alkoxy entirely or partially substituted by fluorine, benzyloxy, phenoxy, mercapto, $C_1$–$C_6$-alkylthio, carboxy, $C_2$–$C_7$-carboxyalkyl, $C_2$–$C_7$-carboxyalkenyl, $C_2$–$C_7$-alkoxycarbonyl, benzyloxycarbonyl, nitro, amino, mono-$C_1$–$C_6$-alkylamino, di-($C_1$–$C_6$-alkyl)-amino and, methylene dioxide for two adjacent residues on the aromatic ring, and wherein alkyl-alkenyl- and cycloalkyl residues in $G^1$, are substituted by one or two of the same or different groups which are selected from the group consisting of hydroxy, carboxy, $C_2$–$C_7$-alkoxycarbonyl, benzyloxycarbonyl, amino, mono-$C_1$–$C_6$-alkylamino and di-($C_1$–$C_6$-alkyl-amino).

25. The pharmaceutical composition of claim 10 wherein a dosage unit for a single administration contains about 0.001 to about 2.0 mg active ingredient.

26. The pharmaceutical composition of claim 10 wherein a dosage unit for a single administration contains about 0.01 to about 2.0 mg active ingredient.

27. The pharmaceutical composition of claim 10 wherein a dosage unit for a single administration contains about 0.1, 1, 2, 5, 10, 20, 25, 30, 50, 100, 200, 300, 500, 600, 800, 1000, 2000, 3000, 4000 to about 5000 mg active ingredient.

28. A method of inhibiting colon, lung, liver and leukemia tumor cell growth in a human or animal body comprising administering to the human or animal body in need thereof an amount of a pharmaceutical composition effective for inhibiting colon, lung, liver and leukemia tumor cell growth, wherein the pharmaceutical composition includes a compound of general formula (I)

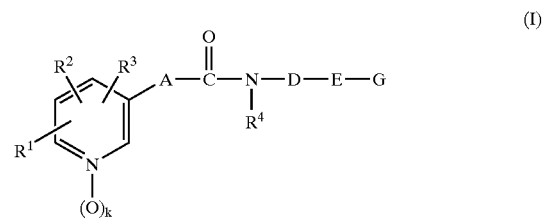

wherein:

$R^1$ is selected from the group consisting of hydrogen, halogen, cyano, $C_1$–$C_6$-alkyl, $C_3$–$C_6$-alkenyl, $C_2$–$C_6$-alkinyl, trifluoromethyl, $C_3$–$C_8$-cycloalkyl, $C_1$–$C_6$-hydroxyalkyl, hydroxy, $C_1$–$C_6$-alkoxy, $C_3$–$C_6$-alkenyloxy, $C_3$–$C_6$-alkinyloxy, benzyloxy, $C_1$–$C_7$-alkanoyloxy, $C_2$–$C_7$-alkoxycarbonyloxy, $C_1$–$C_6$-alkylthio, $C_3$–$C_6$-alkenylthio, $C_3$–$C_6$-alkinylthio, $C_3$–$C_8$-cycloalkyloxy, $C_3$–$C_6$-cycloalkylthio, $C_2$–$C_7$-alkoxycarbonyl, aminocarbonyl, $C_2$–$C_7$-alkylaminocarbonyl, $C_3$–$C_{13}$-dialkylaminocarbonyl, carboxy, phenyl, phenoxy, phenylthio, pyridyloxy, pyridylthio, and $NR^5R^6$, wherein $R^5$ and $R^6$ are selected independently of each other from the group consisting of hydrogen, $C_1$–$C_6$-alkyl, $C_3$–$C_6$-alkenyl, $C_3$–$C_6$-alkinyl, benzyl and phenyl;

$R^2$ is selected from the group consisting of hydrogen, halogen, cyano, $C_1$–$C_6$-alkyl, trifluoromethyl, hydroxy, $C_1$–$C_6$-alkoxy, benzyloxy and $C_1$–$C_7$-alkanoyloxy;

$R^3$ is selected from the group consisting of hydrogen, halogen, $C_1$–$C_6$-alkyl, trifluoromethyl and $C_1$–$C_6$-hydroxyalkyl;

$R^4$ is selected from the group consisting of hydrogen, $C_1$–$C_6$-alkyl, $C_3$–$C_6$-alkenyl, $C_3$–$C_6$-alkinyl, $C_3$–$C_6$-cycloalkyl, hydroxy, $C_1$–$C_6$-alkoxy and benzyloxy;

k is 0 or 1;

A is selected from the group consisting of $C_1$–$C_6$-alkylene;

a susbstituted $C_1$–$C_6$-alkylene which is substituted one to three-fold by $C_1$–$C_3$-alkyl, hydroxy, $C_1$–$C_3$-alkoxy, or fluorine;

$C_2$–$C_6$-alkylene, in which a methylene unit is isosterically replaced by O, S, $NR^9$, CO, SO or $SO_2$, wherein, with the exception of CO, the isosteric substitution is not adjacent to the amide group and $R^9$ is selected from the group consisting of hydrogen, $C_1$–$C_6$-alkyl, $C_3$–$C_6$- alkenyl, $C_3$–$C_6$-alkinyl, $C_1$–$C_6$-acyl and $C_1$–$C_6$-alkanesulfonyl;

$C_2$–$C_6$-alkenylene;

a substituted $C_2$–$C_6$-alkenylene which is substituted once to three-fold by $C_1$–$C_3$-alkyl, hydroxy, $C_1$–$C_3$-alkoxy, fluorine, or cyano;

$C_4$–$C_6$-alkadienylene;

a substituted $C_4$–$C_6$-alkadienylene which is substituted once or twice by $C_1$–$C_3$-alkyl, fluorine, or cyano;

1,3,5-hexatrienylene;

a 1,3,5-hexatrienylene which is substituted by $C_1$–$C_3$-alkyl, fluorine, or cyano; and ethinylene;

D is selected from the group consisting of $C_2$–$C_{10}$-alkylene;

a substituted $C_2$–$C_{10}$-alkylene which is substituted once or twice by $C_1$–$C_6$-alkyl, hydroxy, or $C_1$–$C_6$-alkoxy;

$C_4$–$C_{10}$-alkenylene;

a substituted $C_4$–$C_{10}$-alkenylene which is substituted once or twice by $C_1$–$C_6$-alkyl, hydroxy, or $C_1$–$C_6$-alkoxy;

$C_4$–$C_{10}$-alkinylene;

a substituted $C_4$–$C_{10}$-alkinylene which is substituted once or twice by $C_1$–$C_6$-alkyl, hydroxy, or $C_1$–$C_6$-alkoxy; and $C_2$–$C_{10}$-alkylene, $C_4$–$C_{10}$-alkenylene or $C_4$–$C_{10}$-alkinylene, in which one to three methylene units are isosterically replaced by O, S, $NR^{10}$, CO, SO, or $SO_2$, wherein $R^{10}$ has the same meaning as $R^9$, but is selected independently thereof;

E is

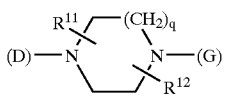

wherein q is 1;

$R^{11}$ is selected from the group consisting of hydrogen $C_1$–$C_6$-alkyl, hydroxy, hydroxymethyl, carboxy, or $C_2$–$C_7$-alkoxycarbonyl;

$R^{12}$ is selected from the group consisting of hydrogen, $C_1$–$C_6$-alkyl and an oxo group adjacent to a nitrogen atom;

G is G1, wherein $G^1$ is —$(CH_2)_r$—$(CR^{14}R^{15})_s$—$R^{13}$ r is 0 to 3;

s is 0 or 1;

$R^{13}$ is selected from the group consisting of hydrogen, $C_1$–$C_6$-alkyl, $C_3$–$C_6$-alkenyl, $C_3$–$C_6$-alkinyl, $C_3$–$C_8$-cycloalkyl;

saturated or unsaturated four to eight-membered heterocycles which contain one or two hetero-atoms selected from the group consisting of N, S and O;

benzyl, phenyl;

monocyclic aromatic five or six-membered heterocycles;

monocyclic aromatic five or six-membered heterocycles which contain one to three hetero-atoms selected from the group consisting of N, S and O where the heteratoms and are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage can occur either over an aromatic ring or a hydrated ring and either directly or over a methylene group;

$R^{14}$ has the same meaning as $R^{13}$, but is selected independently thereof;

$R^{15}$ is selected from the group consisting of hydrogen, hydroxy, methyl, benzyl, and phenyl;

monocyclic aromatic five or six-member heterocycles, which contain one to three hetero-atoms selected from the group consisting of N, S and O and wherein the hetero-atoms are either bound directly or over a methylene group;

anellated bi- and tricyclic aromatic or partially hydrogenated carbocyclic ring systems with 8 to 16 ring atoms and at least one aromatic ring, wherein the linkage occurs either over an aromatic or a hydrogenated ring and either directly or over a methylene group;

anellated bi- and tricyclic aromatic or partially hydrogenated heterocyclic ring systems with 8 to 16 ring atoms and at least one aromatic ring, wherein one to three ring atoms are selected from the group consisting of N, S and O and the linkage occurs either over an aromatic ring or a hydrated ring and either directly or over a methylene group.

29. The pharmaceutical composition according to claim 8, wherein the pharmaceutical composition is present in a solid, peroral administrable form as a tablet, capsule, coated tablet, or as a liquid, peroral administration solution, suspension, effervescent tablet, in the form of tabs or sachets, which may be in the form of a suitable injection or infusion preparation together with suitable pharmaceutically acceptable carriers and adjuvants, in the form of a concentrate, powder or lyophilisate, in the form of a gastrointestinal therapeutic system (GITS) for systemic treatment, in the form of a salve, suspension, emulsion, a balm or plaster or in the form of an externally applicable solution, in the form of a rectal, genital, or transurethral administration emulsion, a solution, a liposomal solution, an implant, suppository or a capsule, or in the form of a composition capable of being applied nasally.

* * * * *